(12) United States Patent
Liu et al.

(10) Patent No.: US 8,153,399 B2
(45) Date of Patent: Apr. 10, 2012

(54) METHODS AND COMPOSITIONS FOR INACTIVATING GLUTAMINE SYNTHETASE GENE EXPRESSION

(75) Inventors: Pei-Qi Liu, Richmond, CA (US); Jeffrey C. Miller, San Leandro, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 301 days.

(21) Appl. No.: 12/589,884

(22) Filed: Oct. 29, 2009

(65) Prior Publication Data

US 2010/0129869 A1 May 27, 2010

Related U.S. Application Data

(60) Provisional application No. 61/197,600, filed on Oct. 29, 2008.

(51) Int. Cl.
*C12P 21/06* (2006.01)
*C12N 1/20* (2006.01)
*C12Q 1/68* (2006.01)
*C12Q 1/48* (2006.01)

(52) U.S. Cl. ............... 435/69.1; 435/252.3; 435/6.1; 435/15

(58) Field of Classification Search ............... 435/69.1, 435/252.3; 530/350
See application file for complete search history.

(56) References Cited

U.S. PATENT DOCUMENTS

| | | | |
|---|---|---|---|
| 5,356,802 A | 10/1994 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,607,882 B1 | 8/2003 | Cox et al. | |
| 6,824,978 B1 | 11/2004 | Cox et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,153,949 B2 | 12/2006 | Kim et al. | |
| 7,163,824 B2 | 1/2007 | Cox et al. | |
| 2003/0232410 A1 | 12/2003 | Liljedahl et al. | |
| 2004/0096452 A1 | 5/2004 | Denney | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0277132 A1 | 12/2005 | Kloek et al. | |
| 2006/0063231 A1 | 3/2006 | Li et al. | |
| 2006/0188987 A1 | 8/2006 | Guschan et al. | |
| 2007/0134796 A1 | 6/2007 | Holmes et al. | |
| 2007/0218528 A1 | 9/2007 | Miller et al. | |
| 2008/0015164 A1 | 1/2008 | Collingwood | |
| 2008/0131962 A1 | 6/2008 | Miller | |
| 2008/0159996 A1 | 7/2008 | Ando et al. | |
| 2008/0188000 A1 | 8/2008 | Reik et al. | |
| 2008/0299580 A1 | 12/2008 | DeKelver et al. | |
| 2009/0042250 A1 | 2/2009 | Collingwood et al. | |
| 2009/0305419 A1 | 12/2009 | Miller et al. | |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 1/2007 |

OTHER PUBLICATIONS

Almassy, et al., "Novel Subunit—Subunit Interactions in the Structure of Glutamine Synthetase," *Nature* 323:304-309 (1986).
Ashworth, et al., "Computational Redesign of Endonuclease DNA Binding and Cleavage Specificity," *Nature* 441:656-659 (2006).
Beerli, et al., "Engineering Polydactyl Zinc-Finger Transcription Factors," *Nature Biotechnology* 20:135-141 (2002).
Bibikova, et al., "Stimulation of Homologous Recombination Through Targeted Cleavage by Chimeric Nucleases," *Mol Cell Biol* 21:289-297 (2001).
Bibikova, et al., "Targeted Chromosomal Cleavage and Mutagenesis in *Drosophila* Using Zinc-Finger Nucleases," *Genetics* 161:1169-1175 (2002).
Bibikova, et al., "Enhancing Gene Targeting With Designed Zinc Finger Nucleases," *Science* 300:764 (2003).
Bitinate, et al., "FokI Dimerization Is Required for DNA Cleavage," *PNAS USA* 95:10570-10575 (1998).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).

(Continued)

*Primary Examiner* — Maryam Monshipouri
(74) *Attorney, Agent, or Firm* — Dahna S. Pasternak; Robins & Pasternak LLP

(57) ABSTRACT

Disclosed herein are methods and compositions for inactivating a glutamine synthetase (GS) gene, using fusion proteins comprising a zinc finger protein and a cleavage domain or cleavage half-domain. Polynucleotides encoding said fusion proteins are also provided, as are cells comprising said polynucleotides and fusion proteins.

18 Claims, 26 Drawing Sheets

OTHER PUBLICATIONS

Epinat, et al., "A Novel Engineered Meganuclease Induces Homologous Recombination in Yeast and Mammalian Cells," *Nucleic Acids Research* 31:2952-2962 (2003).

Gill, et al., "Multicopy Crystallographic Refinement of a Relaxed Glutamine Synthetase From *Mycobacterium tuberculosis* Highlights Flexible Loops in the Enzymatic Mechanism and Its Regulation," *Biochem* 41:9863-9872 (2002).

Isalan et al., "A Rapid, Generally Applicable Method to Engineer Zinc Fingers Illustrated by Targeting the HIV-1 Promoter," *Nat Biotechnol* 19:656-660 (2001).

Kim, et al., "Chimeric Restriction Endonuclease," *PNAS USA* 91:883-887 (1994).

Kim, et al., "Insertion and Deletion Mutants of FOKI Restriction Endonuclease," *J. Biol. Chem.* 269:31978-31981 (1994).

Kohli, et al., "Facile Methods for Generating Human Somatic Cell Gene Knockouts Using Recombinant Adeno-Associated Viruses," *Nucleic Acids Research* 32:E3 (2004).

Li, et al., "Functional Domains in FOK I Restriction Endonuclease," *PNAS USA* 89:4275-4279 (1992).

Li, et al., "Alteration of the Cleavage Distance of FOK I Restriction Endonuclease by Insertion Mutagenesis," *PNAS USA* 90:2764-2768 (1993).

Liaw, et al., "Structural Model for the Reaction Mechanism of Glutamine Synthetase, Based on Five Crystal Structures of Enzyme-Substrate Complexes," *Biochem* 33:675-681 (1994).

Lloyd, et al., "Targeted Mutagenesis Using Zinc-Finger Nucleases in Arabidopsis" *PNAS USA* 102:2232-2237 (2005).

Lombardo, et al., "Gene Editing in Human Stem Cells Using Zinc Finger Nucleases and Integrase-Defective Lentiviral Vector Delivery," *Nature Biotechnology* 25:1298-1306 (2007).

Mansour, et al., "Disruption of the Proto-Oncogene Int-2 in Mouse Embryo-Derived Stem Cells: A General Strategy for Targeting Mutations to Non-Selectable Genes," *Nature* 336:348-352 (1988).

Miller, et al., "An Improved Zinc-Finger Nuclease Architecture for Highly Specific Genome Editing," *Nature Biotech* 25:778-785 (2007).

Moehle, et al., "Targeted Gene Addition Into a Specified Location in the Human Genome Using Designed Zinc Finger Nucleases," *PNAS USA* 104:3055-3060 (2007).

Morton, et al., "Induction and Repair of Zinc-Finger Nuclease-Targeted Double-Strand Breaks in Caenorhabditis Elegans Somatic Cells," *PNAS USA* 103:16370-16375 (2006).

Pabo, et al., "Design and Selection of Novel CYS2-HIS2 Zinc Finger Proteins," *Ann. Rev. Biochem.* 70:313-340 (2001).

Paques, et al., "Meganucleases and DNA Double-Strand Break-Induced Recombination: Perspectives for Gene Therapy," *Current Gene Therapy* 7:49-66 (2007).

Perez, et al., "Establishment of HIV-1 Resistance in CD4+ T Cells by Genome Editing Using Zinc-Finger Nucleases," *Nature Biotechnology* 26:808-816 (2008).

Porteus, et al., "Gene Targeting Using Zinc Finger Nucleases," *Nature Biotechnology* 23:967-973 (2005).

Rago, et al., "Genetic Knockouts and Knockins in Human Somatic Cells," *Nature Protocols* 2:2734-2746 (2007).

Santiago, et al., "Targeted Gene Knockout in Mammalian Cells by Using Engineered Zinc Finger Nucleases," *PNAS USA* 105:5809-5814 (2008).

Segal, et al., "Custom DNA-Binding Proteins Come of Age: Polydactyl Zinc-Finger Proteins," *Curr. Opin. Biotechnol.* 12:632-637 (2001).

Urnov, et al., "Highly Efficient Endogenous Human Gene Correction Using Designed Zinc-Finger Nucleases,," *Nature* 435:646-651 (2005).

Vasquez, et al., "Manipulating the Mammalian Genome by Homologous Recombination," *PNAS USA* 98:8403-8410 (2001).

Wurm, et al., "Production of Recombinant Protein Therapeutics in Cultivated Mammalian Cells," *Nature Biotechnology* 22:1393-1398 (2004).

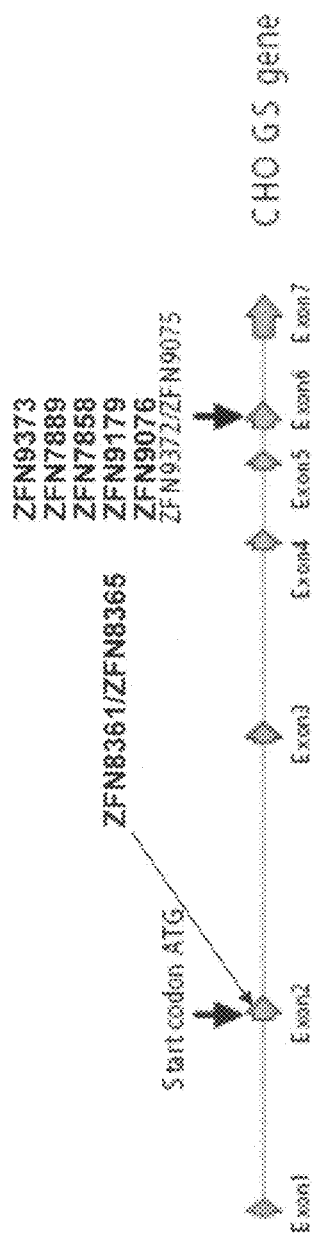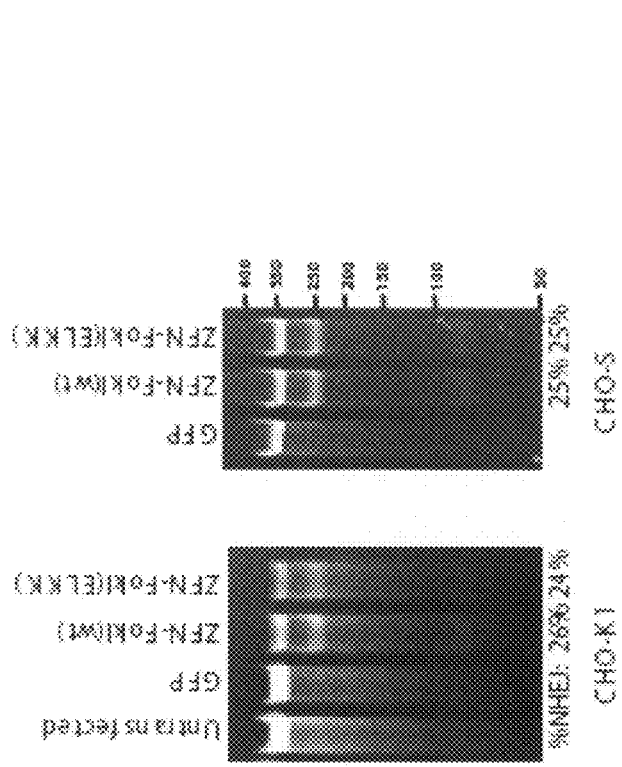
Fig. 1A
Fig. 1B

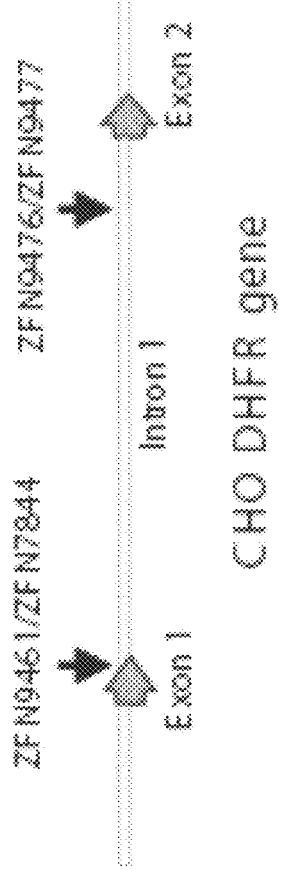
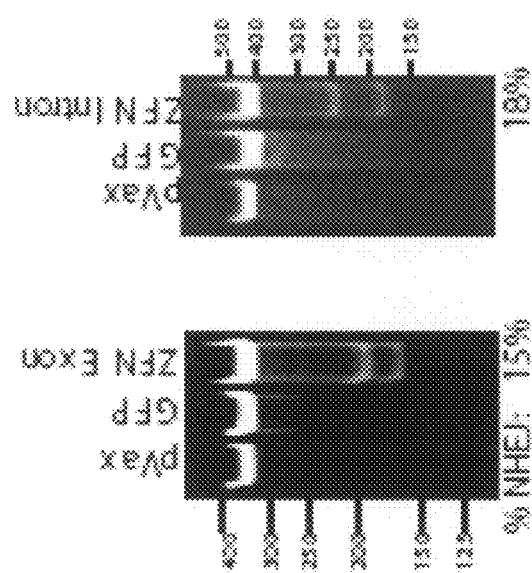
Fig. 2A
Fig. 2B
Fig. 2C

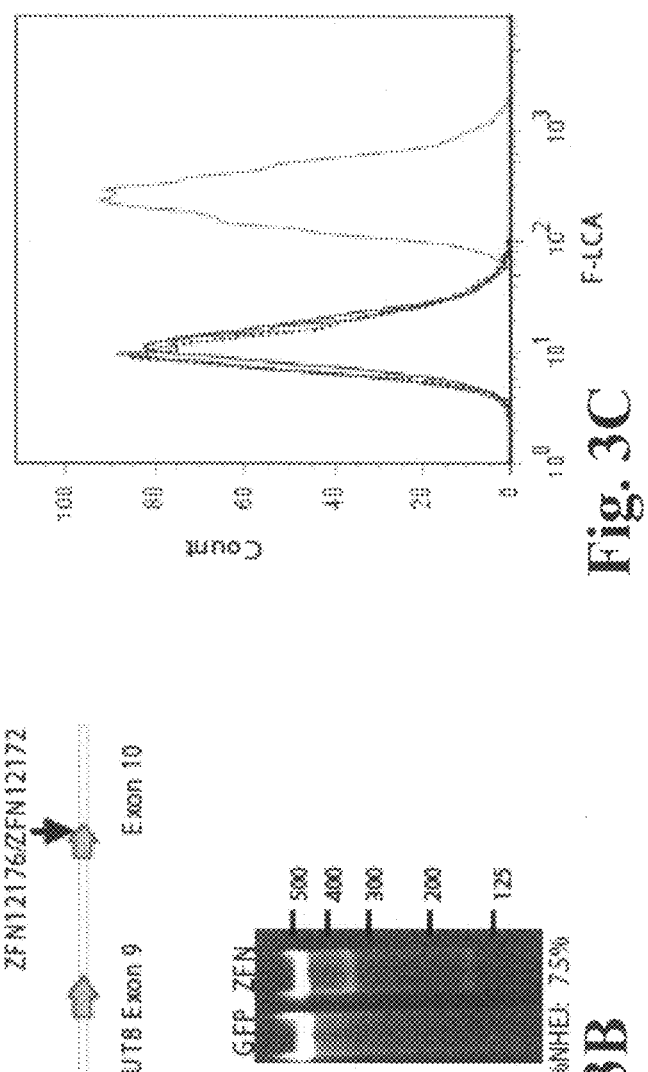

5'...GGTAATAACACCTTTGAGCCCAAGCCATTCCTGGGAACTGGAAGTTGGTGCAGGTGCCATACCAACTTT...3'
3'...CCATTATTGTGGAAACTCGGGTTCGGTAAGGACCCTTGACCTTCAACCACGTCCACGGTATGGTTGAAA...5'

ZFN9075
ZFN9372

Fig. 4B

| ZFP Name | Target Sequence (5'-3') | Triplet Subsites (5'-3') | Finger Designs 123456 | |
|---|---|---|---|---|
| 9075 | gaATGGTGCAGGCTtgc | ATG | RKDVRIT | F4 |
| | | GTG | RSDHLSN | F3 |
| | | CAG | RSDNLRE | F2 |
| | | GCT | QSSDLSR | F1 |
| 9372 | gtTCCCAGGAATGGGCTTGGcgg | TCC | ASNDRKK | F6 |
| | | CAG | RSDNLSQ | F5 |
| | | GAA | QSANRTT | F4 |
| | | TGG | RSDHLSQ | F3 |
| | | GCT | QSSDLRR | F2 |
| | | TGG | RSDHLST | F1 |

```
5'- gggaagcagcgccggcgactgcaatttcgcgccaattcgcctagtgatcgtcgctgccg
     CCATGGTCGAACGCTGAACGTGTCCGAGAATATGGCATCCAAGAACTTCCTGCCAATGCTTAG
     tactggctgaattgggttaggaaccgaggcggttcgctgaatcggtcgagcactggcggga
     cagtcatgaggggtagccggaccgccgcgcagcccttgcccatgctgtgccagcggcgtc
     tagcggaagcaaagtccggtcactggggacttggtagctgatggtagccggcagcgtgaca
     gggtccctgctaacgcagtgtttctcctaactttcagGAACGAATTCAAGTACTTCCAAGT
     attcggggttaagatgaggattctaggggtttgtatgaagcaa -3'
```

Fig. 7A

| ZFP Name | Target Sequence (5'-3') | Triplet Subsites (5'-3') | Finger Designs -1 1 2 3 4 5 6 | |
|---|---|---|---|---|
| 9461 | agGGAAGGTCTCCGtt | GGA<br>AGG<br>TCT<br>CCG | QSGHLSR<br>RSDHLSA<br>NNRDRTK<br>RSDTLSE | F4<br>F3<br>F2<br>F1 |
| 7844 | ccAATGCTCAGGTAct | AAT<br>GCT<br>CAG<br>GTA | TSSNRKT<br>QSSDLSR<br>RSDNLRE<br>QSGALAR | F4<br>F3<br>F2<br>F1 |
| 9476 | caTGGGTAGCCGCTga | TGG<br>GTA<br>GCC<br>GCT | RSDHLTT<br>QSGALAR<br>DRSDLSR<br>QSSDLSR | F4<br>F3<br>F2<br>F1 |
| 9477 | agTCCGGGGGGTGGtg | TCC<br>GGG<br>GGG<br>TGG | DSSDRKK<br>RSDHLSR<br>RSAHLSR<br>RSDHLST | F4<br>F3<br>F2<br>F1 |

| ZFP Name | Target Sequence (5'-3') | Triplet Subsites (5'-3') | Finger Designs -1 1 2 3 4 5 6 | |
|---|---|---|---|---|
| 12176 | caAAGAAGGGTCATCAGtg | AAG<br>AAG<br>GGT<br>CAT<br>CAG | RKDTRIT<br>RSDNLSA<br>TSSILSR<br>NNTQLIE<br>RSDNLRE | F5<br>F4<br>F3<br>F2<br>F1 |
| 12172 | taAAGGAGGCAAAGACAAAGta | AAG<br>GAG<br>GCA<br>AAG<br>ACA<br>AAG | RNDNRKT<br>RSDNLSR<br>QSATRTK<br>RSDHLSQ<br>QNATRIN<br>RSDNLSV | F6<br>F5<br>F4<br>F3<br>F2<br>F1 |

Fig. 9C

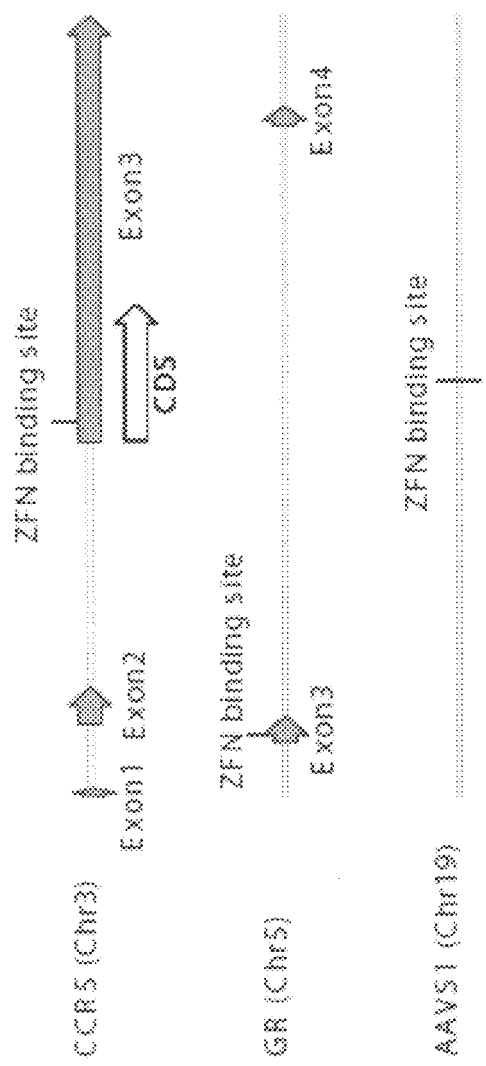
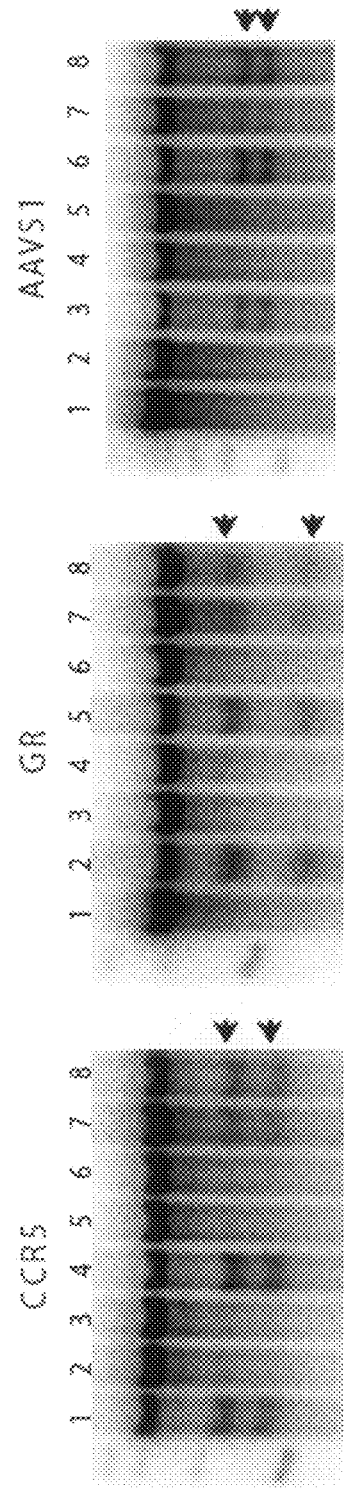
Fig. 10A
Fig. 10B

| Loci | Cells | Genotype | Sequences at target loci (5' - 3') |
|---|---|---|---|
| CCR5 | K562 | wt | 5'-CTTGGTTTTGTGGGCAACATGCTGGTCATCCTCATCCTGATAAACTGCAAAAGGCTGAAGAGCATGACTGACATCTACC-3' |
| | B17 | Δ3bp | 5'-CTTGGTTTTGTGGGCAACATGCTGGTCATCCTCATCCTC---CTGATAAACTGCAAAAGGCTGAAGAGCATGACTGACATCTACC-3' |
| | | Δ12bp | 5'-CTTGGTTTTGTGGGCAACATGCTGGTCATCCTCATC------------AAAAGGCTGAAGACATGACTGACATCTACC-3' |
| | | +5bp | 5'-CTTGGTTTTGTGGGCAACATGCTGGTCATCCTCATCCTGATCCTGATAAACTGCAAAAGGCTGAAGAGCATGACTGACAT-3' |
| GR | K562 | wt | 5'-GACCAGATGTAAGCTCTCCTCCATCCAGTCCTCCAACAGCAACAGGACCAACAGGACCAACTCTGCCTGGTGTGCTCT-3' |
| | B17 | Δ2bp | 5'-GACCAGATGTAAGCTCTCCTCCATCCTCCATCCAGTCCTCCTCAA--GCAACAACAGGACCAACTCTGCCTGGTGTGCTCT-3' |
| | | Δ9bp | 5'-GACCAGATGTAAGCTCTCCTCCATCCTCCATCCAGTCCTCCAACAG---------GACCACCTCCCAAACTCTGCCTGGTGTGCTCT-3' |
| | | Δ12bp | 5'-GACCAGATGTAAGCTCTCCTCCATCCTCCATCCAGTCCTCCTCA------------GGACCACCTCCCAAACTCTGCCTGGTGTGCTCT-3' |
| AAVS1 | K562 | wt | 5'-CTGGGTACTTTTATCTGTCCCCTCCACCCCACAGTGGGGGCCACTAGGGACAGGATTGGTGACAGAAAAGCCCATCCTTA-3' |
| | B17 | Δ19bp | 5'-CTGGGTACTTTTATCTGTCCCCTCCACCCCACAG-------------------ATTGGTGACAGAGAAAAGCCCATCCTTA-3' |

Fig. 10C

|                | ZFN8361                                   | ZFN8365                                   |
|----------------|-------------------------------------------|-------------------------------------------|
| CHO            | TTTGCAGCGCCAGTCCTTCTCCAGTACCATCAACCCAGATATACATCAACATGGCTTGGACTTTCTCACCCTGGGGC |
| Human          | CTTGCAGCGCCAGTCCTTCTCCAGTACCATCGATCAGATCAACCCAGATATACATGGCTTGGACTTTCTCACCCTGAGGC |
| Mouse          | CTTGCAGCGCCAGTCCTTCTCCGGTACCATCAACCCAGATATACATCAACATGGCTTGGACTTTCTCACCCTGGGGC |
| Rat            | ATTGCAGCAGCATAGTCCTTCTCCAGCACCATTGACCTAGATACATCAACATGGCTTGGA-TTTCTCACCCTAAGCC |
| Dog            | CTTGCAACGTAATCCTTCTCCAGTCCGTCAATCAATCAAATATACATAGCTTGCACTTTCTCGCCCTGAGGC |
| Opossum        | TTTACAGCGCAGACCCTCATCAGTGCCATCAATCAGATATACAGATATACATAGCCTGGACTTTGTTGCCTTGAGGC |
| Chicken        | TTTGCAGCGGAGGTGCTCCCAGTCCCGTCCATCAACCCAGATGTACATGGCTTGGACCTTTCTCCCCTGCGGC |
| X. tropicalis  | CTTGCAGCGAAGACCCCTCCCGGTCCCATCAACCCAGTACATAGCCTGCACCTTATCTCCCTGTGGC |
| Tetraodon      | TTTGCAGCGTAGTCCTTCTCCTGTTCCATCAATCAAATATACATGGCCTGAACTTATCCCCCTGTGGG |

Fig. 11A

|                | ZFN9075                                   | ZFN9372                                   |
|----------------|-------------------------------------------|-------------------------------------------|
| CHO            | GCTAAAGTTGGTATGCCAGCCTGCAGCCTTCCAGTTCCCAGGAATGGGCTTGGGCTCAAAGGTTGCTATT |
| Human          | GCTGAAGTTGGTATGGCAGCCTGCAGCCTGCACCATTCCAGTTCCCAGGAATGGGCTTAGGATCAAAGGTTGCTATC |
| Mouse          | GCTGAAGTTGGTATGGCAGCCTGCAGCCTGCACCATTCCAGTTCCCTGGAATGGGCTTGGGCTCAAAGGTTGCTATC |
| Rat            | GCTGAAGTTGGTATGGCAGCCTGCAGCCTGCACTATCAGCCTGCACTATCCAGACTCAGTCTTGGATCAAAGGTCACTATT |
| Dog            | GCTAAAATTGATTATCAGCCTGCACCATTCTCAAGACTCAGTTCCCAGGAATGGGCTTAGGATCAAAGGTTGCTATC |
| Opossum        | GCTGAAGTTGGTGTGGCCAACAGCAGTCCCATTCCAGTTTCCGGGAGGATTGGCTTGGACATTGGCTTGGGATCAAATGATACAATC |
| Chicken        | ACTGAAGTTAGTGTGGCTGTGACAGCCAGACACCGTTCCAGTTCCCAGGAGGATGGGTTTGGGATCGAAGGACACAATG |
| X. tropicalis  | ACTGTAGTTGGTATGGCAACCAGCAGCCGCCGTTCCAGCACCGTTCCGGTCATGGGCTTGGGTCCAGCGTGGCCACC |
| Tetraodon      | GCTGAAGTTGTATGGCAGCCAGCAGCCGGCCAGCACCGTTCCAGTTCCCAGGATTGGCTTGGGGTCAAATGAGGCAATG |
| Fugu           | GCTGAAGTTGGTATGGCAGCCGGCCAGCACCGTTCCAGTTCCCGAGATCGGTTTGGGGTCGAAGGAGGCGACG |
| Zebrafish.chr2 | GTTGAAGTTAGTGTGGCAACCAGCACCAGCACCATTCCAGTTGCCTGGGATCGGCTTAGGATCAAATGAAGCTACC |

Fig. 11B

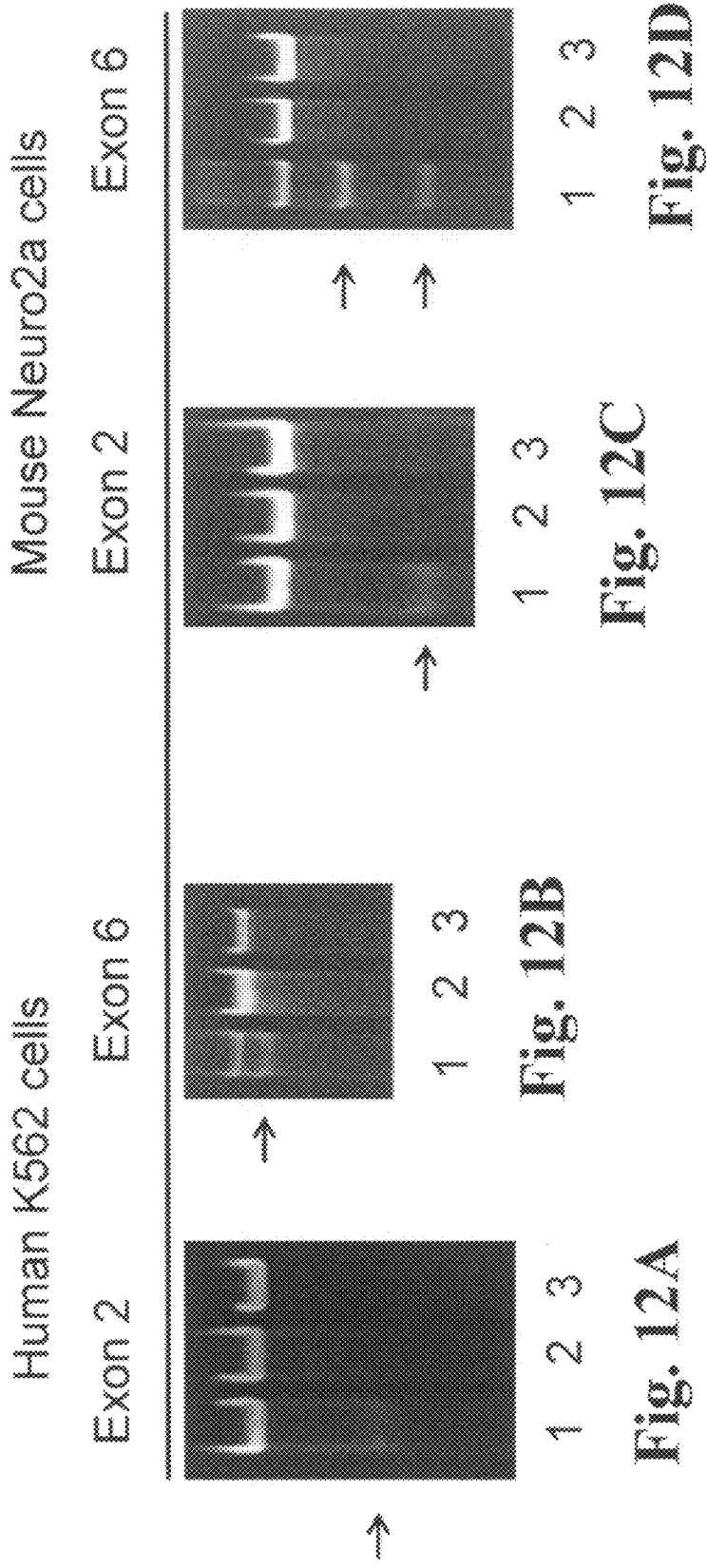

(SEQ ID NO:55)
```
LOCUS       GS\CHO\GS\    6882 bp    DNA                3-MAY-2007
FEATURES             Location/Qualifiers
     exon            1..126
                     /label=Exon1
     exon            1484..1665
                     /label=Exon2
     exon            3491..3652
                     /label=Exon3
     exon            4959..5105
                     /label=Exon4
     exon            5567..5694
                     /label=Exon5
     exon            5876..6075
                     /label=Exon6
     exon            6564..6882
                     /label=Exon7
     misc_feature    1500..1502
                     /label=Start\ATG
     misc_feature    127..155
                     /label=sequencing\gap
BASE COUNT     1825 a     1510 c     1630 g     1888 t     29 others
ORIGIN
        1 cgactggagc acgaggacac tgacatggac tgaaggagta gccaatctcc tcgccgctct
       61 cacttcgcct cgttctcgtg gctcgtggcc ctgtccaccc cgtccatcat cccgccggcc
      121 accgctnnnn nnnnnnnnnn nnnnnnnnnn nnnnntgggc aaacatggac agttgcccgt
      181 agaaactttg ccactgtact tcagagagtt gcccaagtca ttggaggaga acaatatgtt
      241 ccctttccag ccatcctggg cgattaggga gggggggaca tttcctcttg tgttgaagct
      301 ggttttgtag cttcggattc ttaggatttc cacccccccct acccccccctg tggcttgtta
      361 gtcttgcccc acatctttat tagaagtggg agttttctac ttaccagaaa atattatcta
      421 atgaaatctt caaatattgc catgtttaca ttgaagtcag agtttgtctg tggagtaatg
      481 acttttcatc gcaccagtga aaagtcagct caaacctggc ctggaggaac acacactttt
      541 attcccagca ctggggaggc aggtgcaggt ggatctttgt gatagatgcc tggtctacat
      601 ggtaccatga tagggctatg tagagacccc catctccaaa aataaataaa taaataaata
      661 aataaataaa taaataaatc agcaatgtgc tccttggctt tacccttttac caccttggtg
      721 atagcaaata gtacggatct ttttttaaaat ttgttcccag gaatatgtta gccttttaaa
      781 ccttagtccc cttgtctcac ctttaaatcc aactatggag ccaaggagta gtggcagcat
      841 acctttaatc ctagcattca ggaagttgag gctggcagat ctccgagttc gaggctgacc
      901 tggtctgaat agcaaggaaa ttaaggggtg aggcgtatgt ctgttaaagc aagaataaaa
      961 ggcaaaggaa cactccacag tcaattattc aagtcttgat ggcagtaatg tagttgtatt
     1021 gggtggatta agacattcta ataatgaatt tttttgtctt tttgttccct cttttcagct
     1081 ttctcaaaat taatggatat taaaatccc cttagccggg cgttggtggc acacactttt
     1141 aatcccagca ctcgggaggc agaggcaggc agatctctgt gagttcgagg ccagcctggt
     1201 ctccagattg agtgccagga taggctccaa agctacacag aaaccgtgtc tcgaaaaaca
     1261 aaacaaaaaa ataaaaaaaa aaatcccctta actagcccaa cctacaaggg atgatctttg
     1321 tctaactatg aactttaaac ctcttgaaag cagagtgaat aatgcacttc aataatgttg
     1381 acttccaaag gagagaccac cacaccgttc cctgtgcctc ttacgcaatt cctgcagggg
```

Fig. 13A

```
1441 accccctcca gagtagatgt taatgaaatg acttttgtct ctccagagca ccttccacca
1501 tggccacctc agcaagttcc cacttgaaca aaaacatcaa gcaaatgtac ttgtgcctgc
1561 cccagggtga aaagtccaa gccatgtata tctgggttga tggtactgga gaaggactgc
1621 gctgcaaaac ccgcaccctg gactgtgagc ccaagtgtgt agaaggtgag catgggcagg
1681 agcaggacat gtgcctggaa gtgggcaagc agcctgagat ttgaccttcc ttctgttttg
1741 tttgcaaagt ctttcaaaag caggtctctt caggcctcag tcagtcaccc gtaagctgcc
1801 gagtagtctg gaggcataga aaacaatgga ggcctttatt tagatggaat cttgtgtgtg
1861 ctggtacact gaagaaaaat attgggtcat atttgtaggg ggtgggaggt tggagtattg
1921 ctaacctagc caaccccagg aacctagttt gaaagacctg taactagaat atgctatcaa
1981 gtttatagag cagtggttct caaccttttca aatgctttac acttgaatac aactcctcat
2041 gttctggtga ttaccccccat cccaaccatt gctaacttct taactgaaat ttcactactg
2101 ctacgaatca taatgtatct gtgttttggg atggtcttag gtgaccccctg tgaaagggtt
2161 gtgagaccat cctcaaaggg gttgtgacct acaggttgag acccttttga gtgctgtgtt
2221 tattagtatt tatacagtgg aattctgggt gcaaagcaca tgctccaaag tagtttctct
2281 gggactggcc atttgttttc gatggggatc ttttaaaact tgcaaaggaa ccaaaaaaaa
2341 aaaaatgcag aaaaaggag gtgggggagt gcacgccttt aatcccagta cttgggaggc
2401 agaggcaggc ggatctctgt gagtttgaga ccagcctggt ctacaagagc tagttccagg
2461 acagcctcca aagccacaga gaaaccctgt ctcaaaacaa acaaacaaac aaaaaaatta
2521 aaaaaaaaaa aaactttcaa aggagacctg ttttattta gttgtggcct ttgttttggt
2581 aggaagggca gctagtttag gatgagtttt tattattcta agatgttgcc gtttgagtga
2641 atgaatgacc agatgacagc atataacatg tacttgttac ttggcagaag taggtaggtc
2701 gttctgtttc tgccttcagc tcataggtaa ctggggagac aaactggccc caaaacaagg
2761 aaaaggaaca agtggtagga gagcaactgt ttcctcatct acaagagcac agcctgagct
2821 acaacagtca ggccccggaga gggatgagag aagggagggg atgaggtggc ctagtgaggg
2881 agtcagtttt gctctgtgcc atgagtgtct cactcactgg aagtggtgtc agaatgactg
2941 gtgcacagta gacttacaga gaggactcat ctgtttgttg cttgggtggt tcttgtgatg
3001 cagtgctctt gggaacctca aaggaggaa cataggggata ggtgggcata gacatcaggt
3061 tgtccctaat taatgatgat acatttacat acatgccact cagaagacac agtagatttt
3121 cagtgatgga aatatgatga gaggctagct gtcttgtgtg tatatttta ataaattttt
3181 aataaatttc atgtgtgtga gtcagtgcgt gtgtgcgttt gctcgcccag tgctgtgcca
3241 gcagaggtct gaggagggtg tgagaatccc aggaactgaa gttaacagtt gtggttaaga
3301 gtacttatca ctcagttacc agcacctaca tggtggctca aaccatctg taactccaat
3361 ttcaggggct ccaaccccct cttctgcagg catacacttg cacagatata catgcaagta
3421 aaacacccct acacacataa aataaatac gtcttcttaa aagttaattt tccatctta
3481 tttggcccag agttacctga gtggaatttt gatggctcta gtacctttca gtctgagggc
3541 tccaacagtg acatgtatct cagccctgtt gccatgtttc gggacccctt ccgcagagat
3601 cccaacaagc tggtgttctg tgaagttttc aagtacaacc ggaagcctgc aggtgtgtat
3661 ggggtgggcg tgaatgtctt aagaatctag ggatggatga tcagatgtcc atccttctac
3721 cctgaacttg cctgctgaaa aacagtgtgg tccgcccctc catggtccct tttattggtt
3781 gtataaacag tgttgaatct tccatctgtt tgctgatagg ggtccccagt gacagtcttg
3841 atctgcttct acatttaaaa agctgtaatt cgtacttaag cgttttgggg tttaactact
3901 agatctgcca tttattgcca gtgaccttgg catactttgc cccatgcttc tattttgctg
3961 aattatgtgt agagagagac gagacagagc atgcttgaac tgagggcgta ctgtgctctg
4021 tgtggaagtc aaccgacaac ctgtggaatc agttctctcc tgctgtattt gtagattctg
4081 gaggtggaac tcaggttgcc atgagcatta tgattcctgg ctaagctgtt tgcccatgaa
4141 gccttctgta cctgctcata gaattttgtt tatgccgtgc tatccatact cagttttcag
4201 atagcttctt aaacccaggg aactctaatt tacataaact ctcttccagt actgccagta
4261 aggcttggtg gccctatacc ttcagtacct ctgttttgaa aaggaagtat tgttggtcaa
```

Fig. 13B

```
4321  gggtatgtac ctcagcatgg cagccatggg gttcctggct gtgccgcttg ccctataacc
4381  tgggcacgtc accaaacacc ctctctcagg gcttcatttt ctcatttgtg aaagtgaaga
4441  ttgctaacac tcatctcaaa ctcagttaaa tgataaattg cttttctagc ttgggaattg
4501  ttttcagtta cactcacctc tccctcgctt tctctctctt ttttgtacca gccaatactg
4561  tgtaatttag cactcagact cacctggaat gtaaacctaa tggacaaatt attctcagta
4621  aaatgacagc tctggcctta agtgcctacg aaactaggga atacgtttga caagcaggag
4681  cagctgtctt gtgaatagag ggtggaagtg tctggcatgt ggtacttgga aagtggccag
4741  cgtgcagata ggatgaacac ttgttttgct ctcactccat tcccatgaga tttcatagct
4801  gactttaatt ataaaaagtc tctcagcctt ttcctgcaaa tgtactatca ttgcttcttc
4861  acagtggttg ggcctgagta ggtccagcct atgatgactt cagctgtgta agagttgagg
4921  acactactcc ttacagcatg ttgatgcttt attcctagag accaatttaa ggcactcgtg
4981  taaacggata atggacatgg tgagcaacca gcaccctgg tttggaatgg aacaggagta
5041  tactctgatg ggaacagatg ggcacccttt tggttggcct tccaatggct ttcctgggcc
5101  ccaaggtaag ttccccaggt gaaataaaag cttcctcccc ataagttctt actgtccaga
5161  gacaggagca gctcccaaat cagcaaacag actggcagct gaaaataaca gactgtcctt
5221  gcatccctca aatccagatg tgctttgaat ttaaagtgac aggatggtga tgagatggct
5281  cagtgggtaa aggtgcttgc caccaggctt gacagcccga gtttatccct gagacccata
5341  taagttattc tctgaccatc tgcacatgca tgcatataca aaaagtgaaa agctattcag
5401  agtgggcagt agttctacca aggctacagc aaagaggaaa gacctagcct cctacctgca
5461  ggtgaagaca ggatgtgcga aagcaagtct taggaccttg tcatttctg gctttggggg
5521  gttatggact ctgattcttc actgattgct cttgattctc cttcaggtcc gtattactgt
5581  ggtgtgggcg cagacaaagc ctatggcagg gatatcgtgg aggctcacta ccgcgcctgc
5641  ttgtatgctg ggtcaagat tacaggaaca aatgctgagg tcatgcctgc ccaggtaaat
5701  ggcactattc tgttcctttt cctcccctct gaagacttgg cacatgggga ctttggttaa
5761  caagggtgat gacttaaaag tggttcaggg tagaggtaag tagaacaagc taggagcttg
5821  agttggcctg aacagttagt tggccttatt ctaaaggtca acatgttctt tctagtggga
5881  attccaaata ggaccctgtg aaggaatccg catgggagat catctctggg tggcccgttt
5941  catcttgcat cgagtatgtg aagactttgg ggtaatagca acctttgacc ccaagcccat
6001  tcctgggaac tggaatggtg caggctgcca taccaacttt agcaccaagg ccatgcggga
6061  ggagaatggt ctgaagtaag tagcttcctc tggagccatc tttattctca tggggtggaa
6121  gggctttgtg ttaggggttgg gaaagttgga cttctcacaa actacatgcc atgctcttcg
6181  tgtttgtcat aagcctatcg ttttgtaccc gttggagaag tgacagtact ctaggaatag
6241  aattacagct gtgatatggg aaagttgtca cgtaggttca agcatttaaa ggtctttagt
6301  aagaactaaa tacacataca agcaagtggg tgacttaatt cttactgatg ggaagaggcc
6361  agtgatgggg gtcttcccat ccaaaagata attggtatta catgttgagg actggtctga
6421  agcacttgag acataggtca caaggcagac acagcctgca tcaagtattt attggtttct
6481  tatggaactc atgcctgctc ctgcccttga aggacaggtt tctagtgaca aggtcagacc
6541  ctcacctttta ctgcttccac caggcacatc gaggaggcca tcgagaaact aagcaagcgg
6601  caccggtacc acattcgagc ctacgatccc aagggggggcc tggacaatgc ccgtcgtctg
6661  actgggttcc acgaaacgtc caacatcaac gacttttctg ctggtgtcgc caatcgcagt
6721  gccagcatcc gcattccccg gactgtcggc caggagaaga aaggttactt tgaagaccgc
6781  cgcccctctg ccaattgtga ccccttttgca gtgacagaag ccatcgtccg acatgccctt
6841  ctcaatgaga ctggcgacca gcccttccaa tacaaaaact aa
```

Fig. 13C

SEQUENCE LISTING

```
<160> NUMBER OF SEQ ID NOS: 185

<210> SEQ ID NO 1
<211> LENGTH: 16
<212> TYPE: DNA
<213> ORGANISM: Artificial Sequence
<220> FEATURE:
<223> OTHER INFORMATION: Synthetic zinc finger target sequence: ZFN
      9075/ZFN 7858

<400> SEQUENCE: 1
gaatggtgca ggctgc                                                    16

<210> SEQ ID NO 2
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 2

Gln Ser Ser Asp Leu Ser Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 3

Arg Ser Asp Asn Leu Arg Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 4

Arg Ser Asp Thr Leu Ser Asn
```

```
<210> SEQ ID NO 5
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 5

Arg Lys Asp Val Arg Ile Thr
1               5

<210> SEQ ID NO 6
<211> LENGTH: 22
<212> TYPE: DNA
<213> ORGANISM: Artificial Sequence
<220> FEATURE:
<223> OTHER INFORMATION: Synthetic zinc finger target sequence: ZFN 9372

<400> SEQUENCE: 6
gttcccagga atgggcttgg gg                                              22

<210> SEQ ID NO 7
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 7

Arg Ser Asp His Leu Ser Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 8

Gln Ser Ser Asp Leu Arg Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 9

Arg Ser Asp His Leu Ser Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 10
```

```
Gln Ser Ala Asn Arg Thr Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 11

Arg Ser Asp Asn Leu Ser Gln
1               5

<210> SEQ ID NO 12
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 12

Ala Ser Asn Asp Arg Lys Lys
1               5

<210> SEQ ID NO 13
<211> LENGTH: 28
<212> TYPE: DNA
<213> ORGANISM: Artificial Sequence
<220> FEATURE:
<223> OTHER INFORMATION: Synthetic zinc finger target sequence: ZFN 8361

<400> SEQUENCE: 13
ctgggttgat ggtactggag aaggactg                                         28

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 14

Gln Ser Gly Ala Leu Ala Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 15

Arg Ser Asp Ala Leu Thr Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Chemically synthesized zinc finger binding
      domain
```

-continued

<400> SEQUENCE: 16

Arg Ser Asp Ser Leu Ser Ala
1               5

<210> SEQ ID NO 17
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 17

Arg Ser Ala His Leu Ser Arg
1               5

<210> SEQ ID NO 18
<211> LENGTH: 28
<212> TYPE: DNA
<213> ORGANISM: Artificial Sequence
<220> FEATURE:
<223> OTHER INFORMATION: Synthetic zinc finger target sequence: ZFN 8365

<400> SEQUENCE: 18
tatacatggc ttggactttc tcaccctg                                          28

<210> SEQ ID NO 19
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 19

Arg Ser Asp Ser Leu Ser Val
1               5

<210> SEQ ID NO 20
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 20

Asp Asn Ala Asn Arg Thr Lys
1               5

<210> SEQ ID NO 21
<211> LENGTH: 28
<212> TYPE: DNA
<213> ORGANISM: Artificial Sequence
<220> FEATURE:
<223> OTHER INFORMATION: Synthetic zinc finger target sequence: ZFN 9076

<400> SEQUENCE: 21
gaatggtgca ggctgccata ccaacttt                                          28

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized zinc finger binding
      domain

```
<400> SEQUENCE: 22

Arg Ser Ser Ala Leu Thr Arg
1               5

<210> SEQ ID NO 23
<211> LENGTH: 28
<212> TYPE: DNA
<213> ORGANISM: Artificial Sequence
<220> FEATURE:
<223> OTHER INFORMATION: Synthetic zinc finger target sequence: ZFN 9179

<400> SEQUENCE: 23
ggaatggtgc aggctgccat accaactt                                      28

<210> SEQ ID NO 24
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 24

Gln Ser Ser His Leu Thr Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 25

Thr Ser Ser Asn Arg Lys Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 26

Arg Ser Asp Ser Leu Leu Arg
1               5

<210> SEQ ID NO 27
<211> LENGTH: 16
<212> TYPE: DNA
<213> ORGANISM: Artificial Sequence
<220> FEATURE:
<223> OTHER INFORMATION: Synthetic zinc finger target sequence: ZFN 7889

<400> SEQUENCE: 27
gttcccagga atgggc                                                   16

<210> SEQ ID NO 28
<211> LENGTH: 28
<212> TYPE: DNA
<213> ORGANISM: Artificial Sequence
<220> FEATURE:
<223> OTHER INFORMATION: Synthetic zinc finger target sequence: ZFN 9373
```

```
<400> SEQUENCE: 28
gttcccagga atgggcttgg ggtcaaag                                          28

<210> SEQ ID NO 29
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 29

Arg Asn Ala Asp Arg Ile Thr
1               5

<210> SEQ ID NO 30
<211> LENGTH: 819
<212> TYPE: DNA
<213> ORGANISM: Cricetulus longicaudatus

<400> SEQUENCE: 30
atggcactat tctgttcctt ttcctcccct ctgaagactt ggcacatggg gactttggtt      60
aacaagggtg atgacttaaa agtggttcag ggtagaggta agtagaacaa gctaggagct     120
tgagttggcc tgaacagtta gttggcctta ttctaaaggt caacatgttc tttctagtgg     180
gaattccaaa taggaccctg tgaaggaatc cgcatgggag atcatctctg ggtggcccgt     240
ttcatcttgc atcgagtatg tgaagacttt ggggtaatag caaccttga ccccaagccc      300 attcctggga actggaatgg tgcaggctgc ataccaact ttagcaccaa ggccatgcgg      360
gaggagaatg gtctgaagta agtagcttcc tctggagcca tctttattct catggggtgg     420
aagggctttg tgttagggtt gggaaagttg gacttctcac aaactacatg ccatgctctt     480
cgtgtttgtc ataagcctat cgttttgtac ccgttgaga agtgacagta ctctaggaat      540
agaattacag ctgtgatatg ggaaagttgt cacgtaggtt caagcattta aaggtctta     600 gtaagaacta atacacata caagcaagtg ggtgacttaa ttcttactga tgggaagagg      660
ccagtgatgg gggtcttccc atccaaaaga taattggtat tacatgttga ggactggtct     720
gaagcacttg agacataggt cacaaggcag acacagcctg catcaagtat ttattggttt     780
cttatggaac tcatgcctgc tcctgccctt gaaggacag                             819

<210> SEQ ID NO 31
<211> LENGTH: 1766
<212> TYPE: DNA
<213> ORGANISM: Cricetulus longicaudatus

<400> SEQUENCE: 31
ggctggcaga tctccgagtt cgaggctgac ctggtctgaa tagcaaggaa attaaggggt      60
gaggcgtatg tctgttaaag caagaataaa aggcaaagga acactccaca gtcaattatt     120
caagtcttga tggcagtaat gtagttgtat tgggtggatt aagacattct aataatgaat     180 tttttgtct ttttgttccc tctttcagc tttctcaaaa ttaatggata ttaaaaatcc       240
ccttagccgg gcgttggtgg cacacacctt taatcccagc actcgggagg cagaggcagg     300
cagatctctg tgagttcgag gccagcctgg tctccagatt gagtgccagg ataggctcca     360
aagctacaca gaaaccgtgt ctcgaaaaac aaaacaaaaa aataaaaaaa aaatcccctt     420
aactagccca acctcaagg gatgatcttt gtctaactat gaactttaaa cctcttgaaa       480
gcagagtgaa taatgcactt caataatgtt gacttccaaa ggagagacca ccacaccgtt     540
```

-continued

```
ccctgtgcct cttacgcaat tcctgcaggg accccctttc agagtagatg ttaatgaaat    600
gacttttgtc tctccagagc accttccacc atggccacct cagcaagttc ccacttgaac    660
aaaaacatca agcaaatgta cttgtgcctg ccccagggtg agaaagtcca agccatgtat    720
atctggttg atggtactgg agaaggactg cgctgcaaaa cccgcaccct ggactgtgag     780
cccaagtgtg tagaaggtga gcatgggcag gagcaggaca tgtgcctgga agtgggcaag    840
cagcctgaga tttgaccttc cttctgtttt gtttgcaaag tctttcaaaa gcaggtctct    900
tcaggcctca gtcagtcacc cgtaagctgc cgagtagtct ggaggcatag aaaacaatgg    960
aggcctttat ttagatggaa tcttgtgtgt gctggtacac tgaagaaaaa tattgggtca    1020
tatttgtagg gggtgggagg ttggagtatt gctaacctag ccaacccag gaacctagtt     1080
tgaaagacct gtaactagaa tatgctatca agtttataga gcagtggttc tcaacctttc    1140
aaatgcttta cacttgaata caactcctca tgttctggtg attaccccca tcccaaccat    1200
tgctaacttc ttaactgaaa tttcactact gctacgaatc ataatgtatc tgtgttttttg   1260
gatggtctta ggtgacccct gtgaaagggt tgtgagacca tcctcaaagg ggttgtgacc    1320
tacaggttga dacccttttg agtgctgtgt ttattagtat ttatacagtg gaattctggg    1380
tgcaaagcac atgctccaaa gtagtttctc tgggactggc catttgttt cgatggggat    1440
cttttaaaac ttgcaaagga accaaaaaaa aaaaatgca gaaaaaagga ggtggggag     1500
tgcacgcctt taatcccagt acttgggagg cagaggcagg cggatctctg tgagtttgag    1560
accagcctgg tctacaagag ctagttccag gacagcctcc aaagccacag agaaaccctg    1620
tctcaaaaca aacaaacaaa caaaaaaatt aaaaaaaaaa aaactttca aaggagacct     1680
gttttatttt agttgtggcc tttgtttttgg taggaagggc agctagttta ggatgagttt    1740
ttattattct aagatgttgc cgtttg                                          1766
```

<210> SEQ ID NO 32
<211> LENGTH: 16
<212> TYPE: DNA
<213> ORGANISM: Artificial Sequence
<220> FEATURE:
<223> OTHER INFORMATION: Synthetic zinc finger target sequence: ZFN 7844

<400> SEQUENCE: 32
ccaatgctca ggtact                                                   16

<210> SEQ ID NO 33
<211> LENGTH: 16
<212> TYPE: DNA
<213> ORGANISM: Artificial Sequence
<220> FEATURE:
<223> OTHER INFORMATION: Synthetic zinc finger target sequence: ZFN 9461

<400> SEQUENCE: 33
agggaaggtc tccgtt                                                   16

<210> SEQ ID NO 34
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 34

Arg Ser Asp Thr Leu Ser Glu
1               5

```
<210> SEQ ID NO 35
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 35

Asn Asn Arg Asp Arg Thr Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 36

Arg Ser Asp His Leu Ser Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 37

Gln Ser Gly His Leu Ser Arg
1               5

<210> SEQ ID NO 38
<211> LENGTH: 16
<212> TYPE: DNA
<213> ORGANISM: Artificial Sequence
<220> FEATURE:
<223> OTHER INFORMATION: Synthetic zinc finger target sequence: ZFN 9476

<400> SEQUENCE: 38
catgggtagc cgctga                                                    16

<210> SEQ ID NO 39
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 39

Asp Arg Ser Asp Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 40

Arg Ser Asp His Leu Thr Thr
```

```
1               5
```

<210> SEQ ID NO 41
<211> LENGTH: 16
<212> TYPE: DNA
<213> ORGANISM: Artificial Sequence
<220> FEATURE:
<223> OTHER INFORMATION: Synthetic zinc finger target sequence: ZFN 9477

<400> SEQUENCE: 41
agtccggggg gtggtg                                                   16

<210> SEQ ID NO 42
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 42

Arg Ser Asp His Leu Ser Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 43

Asp Ser Ser Asp Arg Lys Lys
1               5

<210> SEQ ID NO 44
<211> LENGTH: 18
<212> TYPE: DNA
<213> ORGANISM: Artificial Sequence
<220> FEATURE:
<223> OTHER INFORMATION: Synthetic zinc finger target sequence: ZFN
      12172

<400> SEQUENCE: 44
aaggaggcaa agacaaag                                                 18

<210> SEQ ID NO 45
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 45

Arg Ser Asp Asn Leu Ser Val
1               5

<210> SEQ ID NO 46
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 46

```
Gln Asn Ala Thr Arg Ile Asn
1               5

<210> SEQ ID NO 47
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 47

Gln Ser Ala Thr Arg Thr Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 48

Arg Ser Asp Asn Leu Ser Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 49

Arg Asn Asp Asn Arg Lys Thr
1               5

<210> SEQ ID NO 50
<211> LENGTH: 15
<212> TYPE: DNA
<213> ORGANISM: Artificial Sequence
<220> FEATURE:
<223> OTHER INFORMATION: Synthetic zinc finger target sequence: ZFN
      12176

<400> SEQUENCE: 50
aagaagggtc atcag                                                    15

<210> SEQ ID NO 51
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 51

Asn Asn Thr Gln Leu Ile Glu
1               5

<210> SEQ ID NO 52
<211> LENGTH: 7
<212> TYPE: PRT
<213> ORGANISM: Artificial Sequence
<220> FEATURE:
<223> OTHER INFORMATION: Chemically synthesized zinc finger binding
      domain
```

<400> SEQUENCE: 52

Thr Ser Ser Ile Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 53

Arg Ser Asp Asn Leu Ser Ala
1               5

<210> SEQ ID NO 54
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 54

Arg Lys Asp Thr Arg Ile Thr
1               5

<210> SEQ ID NO 55
<211> LENGTH: 6882
<212> TYPE: DNA
<213> ORGANISM: Cricetulus longicaudatus
<220> FEATURE:
<221> NAME/KEY: misc_feature
<222> LOCATION: (127)..(155)
<223> OTHER INFORMATION: n is a, c, g, or t

<400> SEQUENCE: 55

```
cgactggagc acgaggacac tgacatggac tgaaggagta gccaatctcc tcgccgctct      60
cacttcgcct cgttctcgtg gctcgtggcc ctgtccaccc cgtccatcat cccgccggcc     120
accgctnnnn nnnnnnnnnn nnnnnnnnnn nnnnntgggc aaacatggac agttgcccgt     180
agaaactttg ccactgtact tcagagagtt gcccaagtca ttggaggaga acaatatgtt     240
cccttttccag ccatcctggg cgattaggga gggggggaca tttcctcttg tgttgaagct     300
ggttttgtag cttcggattc ttaggatttc cacccccccct accccccctg tggcttgtta     360
gtcttgcccc acatctttat tagaagtggg agttttctac ttaccagaaa atattatcta     420
atgaaatctt caaatattgc catgtttaca ttgaagtcag agtttgtctg tggagtaatg     480
acttttcatc gcaccagtga aaagtcagct caaacctggc ctggaggaac acacactttt     540
attcccagca ctggggaggc aggtgcaggt ggatctttgt gatagatgcc tggtctacat     600
ggtaccatga tagggctatg tagagacccc catctccaaa aataaataaa taaataaata     660
aataaataaa taaataaatc agcaatgtgc tccttggctt taccttttac caccttggtg     720
atagcaaata gtacggatct ttttttaaaat ttgttcccag gaatatgtta gccttttaaa     780
ccttagtccc cttgtctcac ctttaaatcc aactatggag ccaaggagta gtggcagcat     840
acctttaatc ctagcattca ggaagttgag gctggcagat ctccgagttc gaggctgacc     900
tggtctgaat agcaaggaaa ttaagggggtg aggcgtatgt ctgttaaagc aagaataaaa     960
ggcaaaggaa cactccacag tcaattattc aagtcttgat ggcagtaatg tagttgtatt    1020
```

```
gggtggatta agacattcta ataatgaatt tttttgtctt tttgttccct cttttcagct      1080
ttctcaaaat taatggatat taaaaatccc cttagccggg cgttggtggc acacaccttt      1140
aatcccagca ctcgggaggc agaggcaggc agatctctgt gagttcgagg ccagcctggt      1200
ctccagattg agtgccagga taggctccaa agctacacag aaaccgtgtc tcgaaaaaca      1260
aaacaaaaaa ataaaaaaaa aaatccctta actagcccaa cctacaaggg atgatctttg      1320
tctaactatg aactttaaac ctcttgaaag cagagtgaat aatgcacttc aataatgttg      1380
acttccaaag gagagaccac cacaccgttc cctgtgcctc ttacgcaatt cctgcagggg      1440 accccttca gagtagatgt taatgaaatg acttttgtct ctccagagca ccttccacca       1500
tggccacctc agcaagttcc cacttgaaca aaaacatcaa gcaaatgtac ttgtgcctgc      1560
cccagggtga gaaagtccaa gccatgtata tctgggttga tggtactgga gaaggactgc     1620
gctgcaaaac ccgcaccctg gactgtgagc ccaagtgtgt agaaggtgag catgggcagg     1680
agcaggacat gtgcctggaa gtgggcaagc agcctgagat ttgaccttcc ttctgttttg     1740
tttgcaaagt cttttcaaaag caggtctctt caggcctcag tcagtcaccc gtaagctgcc    1800
gagtagtctg gaggcataga aaacaatgga ggcctttatt tagatggaat cttgtgtgtg    1860
ctggtacact gaagaaaaat attgggtcat atttgtaggg ggtgggaggt tggagtattg    1920
ctaacctagc caaccccagg aacctagttt gaaagacctg taactagaat atgctatcaa    1980
gtttatagag cagtggttct caacctttca aatgctttac acttgaatac aactcctcat    2040
gttctggtga ttaccccccat cccaaccatt gctaacttct taactgaaat ttcactactg    2100
ctacgaatca taatgtatct gtgttttttgg atggtcttag gtgaccctg tgaaagggtt     2160 gtgagaccat cctcaagggg gttgtgacct acaggttgag accttttga gtgctgtgtt     2220 tattagtatt tatacagtgg aattctgggt gcaaagcaca tgctccaaag tagtttctct    2280
gggactggcc atttgttttc gatggggatc ttttaaaact tgcaaaggaa ccaaaaaaaa     2340
aaaaatgcag aaaaaaggag gtgggggagt gcacgccttt aatcccagta cttgggaggc    2400
agaggcaggc ggatctctgt gagtttgaga ccagcctggt ctacaagagc tagttccagg    2460
acagcctcca aagccacaga gaaaccctgt ctcaaaacaa acaaacaaac aaaaaaatta    2520
aaaaaaaaaa aaactttcaa aggagacctg ttttatttta gttgtggcct ttgttttggt    2580
aggaagggca gctagtttag gatgagtttt tattattcta agatgttgcc gtttgagtga    2640
atgaatgacc agatgacagc atataacatg tacttgttac ttggcagaag taggtaggtc     2700
gttctgtttc tgccttcagc tcataggtaa ctggggagac aaactggccc caaaacaagg    2760
aaaaggaaca agtggtagga gagcaactgt ttcctcatct acaagagcac agcctgagct     2820
acaacagtca ggcccggaga gggatgagag aaggagggg atgaggtggc ctagtgaggg    2880
agtcagtttt gctctgtgcc atgagtgtct cactcactgg aagtggtgtc agaatgactg     2940
gtgcacagta gacttacaga gaggactcat ctgtttgttg cttgggtggt tcttgtgatg    3000
cagtgctctt gggaacctca gaaggaggaa catagggata ggtgggcata gacatcaggt     3060 tgtcccctaat taatgatgat acatttacat acatgccact cagaagacac agtgatttt      3120 cagtgatgga aatatgatga gaggctagct gtcttgtgtg tatattttta ataaattttt     3180
aataaatttc atgtgtgtga gtcagtgcgt gtgtgcgttt gctcgcccag tgctgtgcca    3240
gcagaggtct gaggagggtg tgagaatccc aggaactgaa gttaacagtt gtggttaaga    3300
gtacttatca ctcagttacc agcacctaca tggtggctca caaccatctg taactccaat    3360
ttcaggggct ccaacccccct cttctgcagg catacacttg cacagatata catgcaagta   3420
```

```
aaacacccct acacacataa aaataaatac gtcttcttaa aagttaattt tccatcttta    3480
tttggcccag agttacctga gtggaatttt gatggctcta gtaccttttca gtctgagggc    3540 tccaacagtg acatgtatct cagccctgtt gccatgtttc gggacccctt ccgcagagat    3600
cccaacaagc tggtgttctg tgaagttttc aagtacaacc ggaagcctgc aggtgtgtat    3660
ggggtgggcg tgaatgtctt aagaatctag ggatggatga tcagatgtcc atccttctac    3720
cctgaacttg cctgctgaaa aacagtgtgg tccgccctc catggtccct tttattggtt    3780
gtataaacag tgttgaatct tccatctgtt tgctgatagg ggtccccagt gacagtcttg    3840
atctgcttct acatttaaaa agctgtaatt cgtacttaag cgttttgggg tttaactact    3900
agatctgcca tttattgcca gtgaccttgg catactttgc cccatgcttc tattttgctg    3960
aattatgtgt agagagagac gagacagagc atgcttgaac tgagggcgta ctgtgctctg    4020
tgtggaagtc aaccgacaac ctgtggaatc agttctctcc tgctgtattt gtagattctg    4080
gaggtggaac tcaggttgcc atgagcatta tgattcctgg ctaagctgtt tgcccatgaa    4140
gccttctgta cctgctcata gaattttgtt tatgccgtgc tatccatact cagttttcag    4200
atagcttctt aaacccaggg aactctaatt tacataaact ctcttccagt actgccagta    4260
aggcttggtg gccctatacc ttcagtacct ctgttttgaa aaggaagtat tgttggtcaa    4320
gggtatgtac ctcagcatgg cagccatggg gttcctggct gtgccgcttg ccctataacc    4380
tgggcacgtc accaaacacc ctctctcagg gcttcatttt ctcatttgtg aaagtgaaga    4440
ttgctaacac tcatctcaaa ctcagttaaa tgataaattg ctttttctagc ttgggaattg    4500 ttttcagtta cactcacctc tccctcgctt tctctctctt ttttgtacca gccaatactg    4560
tgtaatttag cactcagact cacctggaat gtaaacctaa tggacaaatt attctcagta    4620
aaatgacagc tctggcctta agtgcctacg aaactaggga atacgtttga caagcaggag    4680
cagctgtctt gtgaatagag ggtggaagtg tctggcatgt ggtacttgga aagtggccag    4740
cgtgcagata ggatgaacac ttgttttgct ctcactccat tcccatgaga tttcatagct    4800
gactttaatt ataaaaagtc tctcagcctt ttcctgcaaa tgtactatca ttgcttcttc    4860
acagtggttg ggcctgagta ggtccagcct atgatgactt cagctgtgta agagttgagg    4920
acactactcc ttacagcatg ttgatgcttt attcctagag accaatttaa ggcactcgtg    4980
taaacggata atggacatgg tgagcaacca gcacccctgg tttggaatgg aacaggagta    5040
tactctgatg ggaacagatg ggcacccttt tggttggcct tccaatggct ttcctgggcc    5100
ccaaggtaag ttccccaggt gaaataaaag cttcctcccc ataagttctt actgtccaga    5160
gacaggagca gctcccaaat cagcaaacag actggcagct gaaaataaca gactgtcctt    5220
gcatccctca aatccagatg tgctttgaat ttaaagtgac aggatggtga tgagatggct    5280
cagtgggtaa aggtgcttgc caccaggctt gacagcccga gtttatccct gagacccata    5340
taagttattc tctgaccatc tgcacatgca tgcatataca aaaagtgaaa agctattcag    5400
agtgggcagt agttctacca aggctacagc aaagaggaaa gacctagcct cctacctgca    5460
ggtgaagaca ggatgtgcga aagcaagtct taggaccttg tcattttctg gctttggggg    5520
gttatggact ctgattcttc actgattgct cttgattctc cttcaggtcc gtattactgt    5580
ggtgtgggcg cagacaaagc ctatggcagg gatatcgtgg aggctcacta ccgcgcctgc    5640
ttgtatgctg gggtcaagat tacaggaaca aatgctgagg tcatgcctgc ccaggtaaat    5700
ggcactattc tgttcctttt cctccctctc gaagacttgg cacatgggga ctttggttaa    5760
caagggtgat gacttaaaag tggttcaggg tagaggtaag tagaacaagc taggagcttg    5820
```

-continued

```
agttggcctg aacagttagt tggccttatt ctaaaggtca acatgttctt tctagtggga    5880
attccaaata ggaccctgtg aaggaatccg catgggagat catctctggg tggcccgttt    5940
catcttgcat cgagtatgtg aagactttgg ggtaatagca acctttgacc ccaagcccat    6000
tcctgggaac tggaatggtg caggctgcca taccaacttt agcaccaagg ccatgcggga    6060
ggagaatggt ctgaagtaag tagcttcctc tggagccatc tttattctca tggggtggaa    6120
gggctttgtg ttagggttgg gaaagttgga cttctcacaa actacatgcc atgctcttcg    6180
tgtttgtcat aagcctatcg ttttgtaccc gttggagaag tgacagtact ctaggaatag    6240
aattacagct gtgatatggg aaagttgtca cgtaggttca agcatttaaa ggtctttagt    6300
aagaactaaa tacacataca agcaagtggg tgacttaatt cttactgatg ggaagaggcc    6360
agtgatgggg gtcttcccat ccaaaagata attggtatta catgttgagg actggtctga    6420
agcacttgag acataggtca caaggcagac acagcctgca tcaagtattt attggtttct    6480
tatggaactc atgcctgctc ctgcccttga aggacaggtt tctagtgaca aggtcagacc    6540
ctcaccttta ctgcttccac caggcacatc gaggaggcca tcgagaaact aagcaagcgg    6600
caccggtacc acattcgagc ctacgatccc aagggggggcc tggacaatgc ccgtcgtctg    6660
actgggttcc acgaaacgtc caacatcaac gactttctg ctggtgtcgc caatcgcagt    6720
gccagcatcc gcattccccg gactgtcggc caggagaaga aaggttactt tgaagaccgc    6780 cgccccctctg ccaattgtga cccctttgca gtgacagaag ccatcgtccg cacatgcctt    6840
ctcaatgaga ctggcgacca gcccttccaa tacaaaaact aa                       6882
```

```
<210> SEQ ID NO 56
<211> LENGTH: 21
<212> TYPE: DNA
<213> ORGANISM: Artificial Sequence
<220> FEATURE:
<223> OTHER INFORMATION: Synthetic zinc finger target sequence: ZFN
      12170

<400> SEQUENCE: 56
taaaggaggc aaagacaaag t                                              21

<210> SEQ ID NO 57
<211> LENGTH: 7
<212> TYPE: PRT
<213> ORGANISM: Artificial Sequence
<220> FEATURE:
<223> OTHER INFORMATION: Chemically synthesized zinc finger binding
      domain

<400> SEQUENCE: 57

Arg Ser Asp Asn Leu Ser Thr
1               5

<210> SEQ ID NO 58
<211> LENGTH: 102
<212> TYPE: DNA
<213> ORGANISM: Cricetulus longicaudatus

<400> SEQUENCE: 58
gcaacctttg accccaagcc cattcctggg aactggaatg gtgcaggctg ccataccaac    60
tttagcacca aggccatgcg ggaggagaat ggtctgaagt aa                       102

<210> SEQ ID NO 59
<211> LENGTH: 32
<212> TYPE: PRT
<213> ORGANISM: Cricetulus longicaudatus
```

```
<400> SEQUENCE: 59

Ala Thr Phe Asp Pro Lys Pro Ile Pro Gly Asn Trp Asn Gly Ala Gly
1               5                   10                  15

Cys Leu Thr Asn Phe Ser Thr Lys Ala Met Arg Glu Glu Asn Gly Leu
            20                  25                  30

<210> SEQ ID NO 60
<211> LENGTH: 89
<212> TYPE: DNA
<213> ORGANISM: Artificial Sequence
<220> FEATURE:
<223> OTHER INFORMATION: Chemically synthesized CHO-S clone

<400> SEQUENCE: 60
gcaacctttg accccaagcc cattcctggg cttgctgcca taccaacttt agcaccaagg     60
ccatgcggga ggagaatggt ctgaagtaa                                      89

<210> SEQ ID NO 61
<211> LENGTH: 83
<212> TYPE: DNA
<213> ORGANISM: Artificial Sequence
<220> FEATURE:
<223> OTHER INFORMATION: Chemically synthesized CHO-S clone

<400> SEQUENCE: 61
gcaacctttg accccaagcc ggtgcaggct gccataccaa ctttagcacc aaggccatgc     60
gggaggagaa tggtctgaag taa                                            83

<210> SEQ ID NO 62
<211> LENGTH: 71
<212> TYPE: DNA
<213> ORGANISM: Artificial Sequence
<220> FEATURE:
<223> OTHER INFORMATION: Chemically synthesized CHO-S clone

<400> SEQUENCE: 62
gcaacctttg accccaagcc cattccaact ttagcaccaa ggccatgcgg gaggagaatg     60
gtctgaagta a                                                         71

<210> SEQ ID NO 63
<211> LENGTH: 73
<212> TYPE: DNA
<213> ORGANISM: Artificial Sequence
<220> FEATURE:
<223> OTHER INFORMATION: Chemically synthesized CHO-S clone

<400> SEQUENCE: 63
gcaacctttg accccaagct gccataccaa ctttagcacc aaggccatgc gggaggagaa     60
tggtctgaag taa                                                       73

<210> SEQ ID NO 64
<211> LENGTH: 42
<212> TYPE: DNA
<213> ORGANISM: Artificial Sequence
<220> FEATURE:
<223> OTHER INFORMATION: Chemically synthesized CHO-S clone

<400> SEQUENCE: 64
gcaacctttg accccaagcc cattcctgta cccgttggag aa                       42

<210> SEQ ID NO 65
<211> LENGTH: 55
```

```
<212> TYPE: DNA
<213> ORGANISM: Artificial Sequence
<220> FEATURE:
<223> OTHER INFORMATION: Chemically synthesized CHO-S clone

<400> SEQUENCE: 65
gcaacctttg accccaagcc cattcctggg ctttgtgtta gggttgggaa agttg          55

<210> SEQ ID NO 66
<211> LENGTH: 75
<212> TYPE: DNA
<213> ORGANISM: Artificial Sequence
<220> FEATURE:
<223> OTHER INFORMATION: Chemically synthesized CHO-S clone

<400> SEQUENCE: 66
gcaaccagga atggtgcagg ctgccatacc aactttagca ccaaggccat gcgggaggag     60
aatggtctga agtaa                                                     75

<210> SEQ ID NO 67
<211> LENGTH: 95
<212> TYPE: DNA
<213> ORGANISM: Artificial Sequence
<220> FEATURE:
<223> OTHER INFORMATION: Chemically synthesized CHO-S clone

<400> SEQUENCE: 67
gcaacctttg accccaagcc cattccagga atggtgcagg ctgccatacc aactttagca     60
ccaaggccat gcgggaggag aatggtctga agtaa                               95

<210> SEQ ID NO 68
<211> LENGTH: 102
<212> TYPE: DNA
<213> ORGANISM: Cricetulus longicaudatus

<400> SEQUENCE: 68
gcaacctttg accccaagcc cattcctggg aactggaatg gtgcaggctg ccataccaac     60
tttagcacca aggccatgcg ggaggagaat ggtctgaagt aa                       102

<210> SEQ ID NO 69
<211> LENGTH: 96
<212> TYPE: DNA
<213> ORGANISM: Artificial Sequence
<220> FEATURE:
<223> OTHER INFORMATION: Chemically synthesized CHO-K1 clone

<400> SEQUENCE: 69
gcaacctttg accccaagcc cattcctggg aatggtgcag gctgccatac caactttagc     60
accaaggcca tgcgggagga gaatggtctg aagtaa                              96

<210> SEQ ID NO 70
<211> LENGTH: 48
<212> TYPE: DNA
<213> ORGANISM: Artificial Sequence
<220> FEATURE:
<223> OTHER INFORMATION: Chemically synthesized CHO-K1 clone

<400> SEQUENCE: 70
gcaacctttg accccaaggc catgcgggag gagaatggtc tgaagtaa                 48

<210> SEQ ID NO 71
<211> LENGTH: 94
<212> TYPE: DNA
<213> ORGANISM: Artificial Sequence
```

```
<220> FEATURE:
<223> OTHER INFORMATION: Chemically synthesized CHO-K1 clone

<400> SEQUENCE: 71
gcaacctttg accccaagcc cattccagaa tggtgcaggc tgccatacca actttagcac      60
caaggccatg cggaggaga atggtctgaa gtaa                                  94

<210> SEQ ID NO 72
<211> LENGTH: 106
<212> TYPE: DNA
<213> ORGANISM: Artificial Sequence
<220> FEATURE:
<223> OTHER INFORMATION: Chemically synthesized CHO-K1 clone

<400> SEQUENCE: 72
gcaacctttg accccaagcc cattcctggg aactggctgg aatggtgcag gctgccatac      60
caactttagc accaaggcca tgcgggagga gaatggtctg aagtaa                    106

<210> SEQ ID NO 73
<211> LENGTH: 97
<212> TYPE: DNA
<213> ORGANISM: Artificial Sequence
<220> FEATURE:
<223> OTHER INFORMATION: Chemically synthesized CHO-K1 clone

<400> SEQUENCE: 73
gcaacctttg accccaagcc cattcctggg aaatggtgca ggctgccata ccaactttag      60
caccaaggcc atgcgggagg agaatggtct gaagtaa                              97

<210> SEQ ID NO 74
<211> LENGTH: 77
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 74
aacggagacc ttccctggcc aatgctcagg tactggctgc agcaccaccc cccggacttg      60
catgggtagc cgctgag                                                    77

<210> SEQ ID NO 75
<211> LENGTH: 34
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 75
aacggagacc ttccctggct gggtagccgc tgag                                 34

<210> SEQ ID NO 76
<211> LENGTH: 73
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 76
aacggagacc ttccccaatg ctcaggtact ggctgcagca ccaccccccg gacttgcatg      60
ggtagccgct gag                                                        73
```

<210> SEQ ID NO 77
<211> LENGTH: 30
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 77
aacggagacc ttccctggct ccccgctgag                                         30

<210> SEQ ID NO 78
<211> LENGTH: 38
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 78
aacggagacc ttccctggct gcatgggtag ccgctgag                                38

<210> SEQ ID NO 79
<211> LENGTH: 76
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 79
aacggagacc ttccctggct ggccaatgct caggtactgg ctagcaccac ccccggact         60 tgcggtagcc gctgag                                                        76

<210> SEQ ID NO 80
<211> LENGTH: 35
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 80
aacggagacc ttccctggca tgggtagccg ctgag                                   35

<210> SEQ ID NO 81
<211> LENGTH: 66
<212> TYPE: DNA
<213> ORGANISM: Artificial Sequence
<220> FEATURE:
<223> OTHER INFORMATION: Synthetic oligonucleotide used in DHFR
      genotyping analysis

<400> SEQUENCE: 81
aacggagacc ttccctggcc aatgctcagg tactggctgc agcaccaccc ccggacttg         60 ccctgt                                                                   66

<210> SEQ ID NO 82
<211> LENGTH: 63
<212> TYPE: DNA
<213> ORGANISM: Artificial Sequence
<220> FEATURE:
<223> OTHER INFORMATION: Synthetic oligonucleotide used in FUT8 gene
      analysis

<400> SEQUENCE: 82

```
aaaagagtgt atctggccac tgatgaccct tctttgttaa aggaggcaaa gacaaagtaa    60
gtt                                                                  63
```

<210> SEQ ID NO 83
<211> LENGTH: 18
<212> TYPE: PRT
<213> ORGANISM: Artificial sequence
<220> FEATURE:
<223> OTHER INFORMATION: Synthetic peptide used in FUT8 gene analysis

<400> SEQUENCE: 83

```
Lys Arg Val Tyr Leu Ala Thr Asp Asp Pro Ser Leu Leu Lys Glu Ala
1               5                   10                  15

Lys Thr
```

<210> SEQ ID NO 84
<211> LENGTH: 59
<212> TYPE: DNA
<213> ORGANISM: Artificial Sequence
<220> FEATURE:
<223> OTHER INFORMATION: Synthetic oligonucleotide used in FUT8 gene
      analysis

<400> SEQUENCE: 84

```
aaaagagtgt atctggccac tgatgaccct tcttaaagga ggcaaagaca aagtaagtt     59
```

<210> SEQ ID NO 85
<211> LENGTH: 58
<212> TYPE: DNA
<213> ORGANISM: Artificial Sequence
<220> FEATURE:
<223> OTHER INFORMATION: Synthetic oligonucleotide used in FUT8 gene
      analysis

<400> SEQUENCE: 85

```
aaaagagtgt atctggccac tgatgaccct tttaaggag gcaaagacaa agtaagtt       58
```

<210> SEQ ID NO 86
<211> LENGTH: 64
<212> TYPE: DNA
<213> ORGANISM: Artificial Sequence
<220> FEATURE:
<223> OTHER INFORMATION: Synthetic oligonucleotide used in FUT8 gene
      analysis

<400> SEQUENCE: 86

```
aaaagagtgt atctggccac tgatgaccct tctttggtta aggaggcaa agacaaagta     60 agtt                                                                 64
```

<210> SEQ ID NO 87
<211> LENGTH: 67
<212> TYPE: DNA
<213> ORGANISM: Artificial Sequence
<220> FEATURE:
<223> OTHER INFORMATION: Synthetic oligonucleotide used in FUT8 gene
      analysis

<400> SEQUENCE: 87

```
aaaagagtgt atctggccac tgatgaccct tctttgtttg ttaaaggagg caaagacaaa    60
gtaagtt                                                              67
```

<210> SEQ ID NO 88
<211> LENGTH: 518
<212> TYPE: DNA
<213> ORGANISM: Cricetulus longicaudatus -continued

<400> SEQUENCE: 88

```
agggtgatga cttaaaagtg gttcagggta gaggtaagta gaacaagcta ggagcttgag    60
ttggcctgaa cagttagttg gccttattct aaaggtcaac atgttctttc tagtgggaat   120
tccaaatagg accctgtgaa ggaatccgca tgggagatca tctctgggtg gcccgtttca   180
tcttgcatcg agtatgtgaa gactttgggg taatagcaac ctttgacccc aagcccattc   240
ctgggaactg gaatggtgca ggctgccata ccaactttag caccaaggcc atgcgggagg   300
agaatggtct gaagtaagta gcttcctctg gagccatctt tattctcatg ggtggaagg    360
gctttgtgtt agggttggga agttggact tctcacaaac tacatgccat gctcttcgtg    420
tttgtcataa gcctatcgtt ttgtacccgt tggagaagtg acagtactct aggaatagaa   480
ttacagctgt gatatgggaa agttgtcacg taggttca                           518
```

<210> SEQ ID NO 89
<211> LENGTH: 70
<212> TYPE: DNA
<213> ORGANISM: Artificial Sequence
<220> FEATURE:
<223> OTHER INFORMATION: Synthetic sequence containing ZFN9075

<400> SEQUENCE: 89

```
ggtaatagca acctttgacc ccaagcccat tcctgggaac tggaatggtg caggctgcca    60
taccaacttt                                                          70
```

<210> SEQ ID NO 90
<211> LENGTH: 70
<212> TYPE: DNA
<213> ORGANISM: Artificial Sequence
<220> FEATURE:
<223> OTHER INFORMATION: Synthetic sequence containing ZFN9372

<400> SEQUENCE: 90

```
aaagttggta tggcagcctg caccattcca gttcccagga tgggcttgg ggtcaaaggt     60
tgctattacc                                                          70
```

<210> SEQ ID NO 91
<211> LENGTH: 90
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 91

```
gtaatagcaa cctttgaccc caagcccatt cctgggaact ggaatggtgc aggctgccat    60
accaactttca gcaccaaggc catgcgggag                                   90
```

<210> SEQ ID NO 92
<211> LENGTH: 88
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 92

```
gtaatagcaa cctttgaccc caagcccatt cctgggaact ggtggtgcag gctgccatac    60
caactttagc accaaggcca tgcgggag                                      88
```

```
<210> SEQ ID NO 93
<211> LENGTH: 88
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 93
gtaatagcaa cctttgaccc caagcccatt cctgggatgg aatggtgcag gctgccatac    60
caactttagc accaaggcca tgcgggac                                       88

<210> SEQ ID NO 94
<211> LENGTH: 87
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 94
gtaatagcaa cctttgaccc caagcccatt cctgggaaca atggtgcagg ctgccatacc    60
aactttagca ccaaggccat gcgggag                                        87

<210> SEQ ID NO 95
<211> LENGTH: 87
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 95
gtaatagcaa cctttgaccc caagcccatt cctgggaata atggtgcagg ctgccatacc    60
aactttagca ccaaggccat gcgggag                                        87

<210> SEQ ID NO 96
<211> LENGTH: 87
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 96
gtaatagcaa cctttgaccc caagcccatt cctgggaact ggggtgcagg ctgccatacc    60
aactttagca ccaaggccat gcgggac                                        87

<210> SEQ ID NO 97
<211> LENGTH: 86
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 97
gtaatagcaa cctttgaccc caagcccatt cctgggaact gggtgcaggc tgccatacca    60
actttagcac caaggccatg cgggag                                         86

<210> SEQ ID NO 98
<211> LENGTH: 86
<212> TYPE: DNA
<213> ORGANISM: Artificial Sequence
<220> FEATURE:
```

-continued

<223> OTHER INFORMATION: Synthetic sequence resulting from sequencing of
     genomic GS locus from ZFN transfected cells

<400> SEQUENCE: 98
gtaatagcaa cctttgaccc caagcccatt cctgctggaa tggtgcaggc tgccatacca    60
actttagcac caaggccatg cgggag    86

<210> SEQ ID NO 99
<211> LENGTH: 86
<212> TYPE: DNA
<213> ORGANISM: Artificial Sequence
<220> FEATURE:
<223> OTHER INFORMATION: Synthetic sequence resulting from sequencing of
     genomic GS locus from ZFN transfected cells

<400> SEQUENCE: 99
gtaatagcaa cctttgaccc caagcccatt cctgggaatt tggtgcaggc tgccatacca    60
actttagcac caaggccatg cgggag    86

<210> SEQ ID NO 100
<211> LENGTH: 86
<212> TYPE: DNA
<213> ORGANISM: Artificial Sequence
<220> FEATURE:
<223> OTHER INFORMATION: Synthetic sequence resulting from sequencing of
     genomic GS locus from ZFN transfected cells

<400> SEQUENCE: 100
gtaatagcaa cctttgaccc caagcccatt cctgggaaaa tggtgcaggc tgccatacca    60
actttagcac caaggccatg cgggag    86

<210> SEQ ID NO 101
<211> LENGTH: 85
<212> TYPE: DNA
<213> ORGANISM: Artificial Sequence
<220> FEATURE:
<223> OTHER INFORMATION: Synthetic sequence resulting from sequencing of
     genomic GS locus from ZFN transfected cells

<400> SEQUENCE: 101
gtaatagcaa cctttgaccc caagcccatt cctgggaact ggtgcaggct gccataccaa    60
ctttagcacc aaggccatgc gggag    85

<210> SEQ ID NO 102
<211> LENGTH: 85
<212> TYPE: DNA
<213> ORGANISM: Artificial Sequence
<220> FEATURE:
<223> OTHER INFORMATION: Synthetic sequence resulting from sequencing of
     genomic GS locus from ZFN transfected cells

<400> SEQUENCE: 102
gtaatagcaa cctttgaccc caagcccatt cctgggaaat ggtgcaggct gccataccaa    60
ctttagcacc aaggccatgc gggag    85

<210> SEQ ID NO 103
<211> LENGTH: 84
<212> TYPE: DNA
<213> ORGANISM: Artificial Sequence
<220> FEATURE:
<223> OTHER INFORMATION: Synthetic sequence resulting from sequencing of
     genomic GS locus from ZFN transfected cells

<400> SEQUENCE: 103

```
gtaatagcaa cctttgaccc caagcccatt cctgggaatg gtgcaggctg ccataccaac    60
tttagcacca aggccatgcg ggag                                           84

<210> SEQ ID NO 104
<211> LENGTH: 83
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 104
gtaatagcaa cctttgaccc caagcccatt cctgggatgg tgcaggctgc cataccaact    60
ttagcaccaa ggccatgcgg gag                                            83

<210> SEQ ID NO 105
<211> LENGTH: 83
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 105
gtaatagcaa cctttgaccc caagcccatt cctggaatgg tgcaggctgc cataccaact    60
ttagcaccaa ggccatgcgg gag                                            83

<210> SEQ ID NO 106
<211> LENGTH: 82
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 106
gtaatagcaa cctttgaccc caagcccatt ctggaatggt gcaggctgcc ataccaactt    60
tagcaccaag gccatgcggg ag                                             82

<210> SEQ ID NO 107
<211> LENGTH: 82
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 107
gtaatagcaa cctttgaccc caagcccatt cctgggtggt gcaggctgcc ataccaactt    60
tagcaccaag gccatgcggg ag                                             82

<210> SEQ ID NO 108
<211> LENGTH: 81
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 108
gtaatagcaa cctttgaccc caagcccatt cctggtggtg caggctgcca taccaacttt    60
agcaccaagg ccatgcggga g                                              81
```

<210> SEQ ID NO 109
<211> LENGTH: 81
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 109
gtaatagcaa cctttgaccc caagcccatt cctgggaact ggggctgcca taccaacttt     60
agcaccaagg ccatgcggga g                                               81

<210> SEQ ID NO 110
<211> LENGTH: 80
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 110
gtaatagcaa cctttgaccc caagcccatt cctgggaacc aggctgccat accaacttta     60
gcaccaaggc catgcgggag                                                 80

<210> SEQ ID NO 111
<211> LENGTH: 78
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 111
gtaatagcaa cctttgaccc caagcccatt cctggtgcag gctgccatac caactttagc     60
accaaggcca tgcgggag                                                   78

<210> SEQ ID NO 112
<211> LENGTH: 77
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 112
gtaatagcaa cctttgaccc caagcccaaa atggtgcagg ctgccatacc aactttagca     60
ccaaggccat gcgggag                                                    77

<210> SEQ ID NO 113
<211> LENGTH: 75
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 113
gtaatagcaa cctttgaccc caagcccaat ggtgcaggct gccataccaa ctttagcacc     60
aaggccatgc gggag                                                      75

<210> SEQ ID NO 114
<211> LENGTH: 73
<212> TYPE: DNA
<213> ORGANISM: Artificial Sequence
<220> FEATURE:

<223> OTHER INFORMATION: Synthetic sequence resulting from sequencing of
      genomic GS locus from ZFN transfected cells

<400> SEQUENCE: 114
gtaatagcaa cctttgaccc caagcccatt cctgggctgc cataccaact ttagcaccaa    60
ggccatgcgg gag    73

<210> SEQ ID NO 115
<211> LENGTH: 72
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 115
gtaatagcaa cctttgaccc ctggaatggt gcaggctgcc ataccaactt tagcaccaag    60
gccatgcggg ag    72

<210> SEQ ID NO 116
<211> LENGTH: 70
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 116
gtaatagcaa cctttgaccc caagcccatt aggctgccat accaactttta gcaccaaggc    60 catgcgggag    70

<210> SEQ ID NO 117
<211> LENGTH: 69
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 117
gtaatagcaa cctttgaccc caagcccgca ggctgccata ccaactttag caccaaggcc    60
atgcgggag    69

<210> SEQ ID NO 118
<211> LENGTH: 69
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 118
gtaatagcaa cctttgaccc caagcccatt cctggccata ccaactttag caccaaggcc    60
atgcgggag    69

<210> SEQ ID NO 119
<211> LENGTH: 59
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 119

```
gtaatagcaa cctttgaccc caagcccatt ccaactttag caccaaggcc atgcgggag      59

<210> SEQ ID NO 120
<211> LENGTH: 59
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 120
gtaatagcaa cctttgaccc caagcccatt cctgctttag caccaaggcc atgcgggag      59

<210> SEQ ID NO 121
<211> LENGTH: 58
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 121
gtaatagcaa cctttgaccc caagccatac caactttagc accaaggcca tgcgggag       58

<210> SEQ ID NO 122
<211> LENGTH: 41
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 122
gtaatagcaa cctttgaccc caagccaagg ccatgcggga g                         41

<210> SEQ ID NO 123
<211> LENGTH: 90
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 123
gtaatagcaa cctttgaccc caagcccatt cctgggaacg tggaatggtg caggctgcca     60
taccaacttt agcaccaagg ccatgcggga                                      90

<210> SEQ ID NO 124
<211> LENGTH: 90
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 124
gtaatagcaa cctttgaccc caagcccatt cctgggaact gggaatggtg caggctgcca     60
taccaacttt agcaccaagg ccatgcggga                                      90

<210> SEQ ID NO 125
<211> LENGTH: 90
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells
```

-continued

```
<400> SEQUENCE: 125
gtaatagcaa cctttgaccc caagcccatt cctgggaact ggtaatggtg caggctgcca    60
taccaacttt agcaccaagg ccatgcggga                                     90

<210> SEQ ID NO 126
<211> LENGTH: 90
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 126
gtaatagcaa cctttgaccc caagcccatt cctgggaact ggaaatggtg caggctgcca    60
taccaacttt agcaccaagg ccatgcggga                                     90

<210> SEQ ID NO 127
<211> LENGTH: 93
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 127
gtaatagcaa cctttgaccc caagcccatt cctgggaact ggtggaatgg tgcaggctgc    60
cataccaact ttagcaccaa ggccatgcgg gag                                 93

<210> SEQ ID NO 128
<211> LENGTH: 94
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 128
gtaatagcaa cctttgaccc caagcccatt cctgggaact ggctggaatg gtgcaggctg    60
ccataccaac tttagcacca aggccatgcg ggag                                94

<210> SEQ ID NO 129
<211> LENGTH: 94
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 129
gtaatagcaa cctttgaccc caagcccatt cctgggaact ggactggaat ggtgcaggct    60
gccataccaa ctttagcacc aaggccatgc ggga                                94

<210> SEQ ID NO 130
<211> LENGTH: 94
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 130
gtaatagcaa cctttgaccc caagcccatt cctgggaatg ggatgggaat ggtgcaggct    60
gccataccaa ctttagcacc aaggccatgc ggga                                94
```

<210> SEQ ID NO 131
<211> LENGTH: 94
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 131

```
gtaatagcaa cctttgaccc caagcccatt cctgggcttt cactggtgag ccatggtgca    60
ggctgccata ccaactttag caccaaggcc atgc                                94
```

<210> SEQ ID NO 132
<211> LENGTH: 94
<212> TYPE: DNA
<213> ORGANISM: Artificial Sequence
<220> FEATURE:
<223> OTHER INFORMATION: Synthetic sequence resulting from sequencing of
      genomic GS locus from ZFN transfected cells

<400> SEQUENCE: 132

```
gtaatagcaa cctttgaccc caagcccatt cctgggaact gggggcccca taagccctgt    60
ctcatggtgc aggctgccat accaacttta gcac                                94
```

<210> SEQ ID NO 133
<211> LENGTH: 572
<212> TYPE: DNA
<213> ORGANISM: Cricetulus longicaudatus

<400> SEQUENCE: 133

```
gggaagcagc gccgggcgac tgcaatttcg cgccaaactt gggggaagca cagcgtacag    60
gctgcctagg tgatcgctgc tgctgccatg gttcgaccgc tgaactgcat cgtcgccgtg   120
tcccagaata tgggcatcgg caagaacgga gaccttccct ggccaatgct caggtactgg   180
ctggattggg ttagggaaac cgaggcggtt cgctgaatcg ggtcgagcac ttggcggaga   240
cgcgcgggcc aactacttag ggacagtcat gaggggtagg cccgccggct gcagcccttg   300
cccatgcccg cggtgatccc catgctgtgc cagccttttgc ccagaggcgc tctagctggg   360
agcaaagtcc ggtcactggg cagcaccacc ccccggactt gcatgggtag ccgctgagat   420
ggagcctgag cacacgtgac agggtccctg ttaacgcagt gtttctctaa ctttcaggaa   480
cgaattcaag tacttccaaa gaatgaccac cacctcctca gtggaaggta atttgggtt    540 aagatgagga ttctagggtt tgtatgaagc aa                                 572
```

<210> SEQ ID NO 134
<211> LENGTH: 82
<212> TYPE: DNA
<213> ORGANISM: Artificial Sequence
<220> FEATURE:
<223> OTHER INFORMATION: Synthetic sequence containing ZFN7844

<400> SEQUENCE: 134

```
gtcgccgtgt cccagaatat gggcatcggc aagaacggag accttccctg gccaatgctc    60
aggtactggc tggattgggt ta                                             82
```

<210> SEQ ID NO 135
<211> LENGTH: 82
<212> TYPE: DNA
<213> ORGANISM: Artificial Sequence
<220> FEATURE:
<223> OTHER INFORMATION: Synthetic sequence containing ZFN9461

<400> SEQUENCE: 135

```
taacccaatc cagccagtac ctgagcattg ccagggaag gtctccgttc ttgccgatgc    60
ccatattctg ggacacggcg ac                                            82
```

<210> SEQ ID NO 136
<211> LENGTH: 81
<212> TYPE: DNA
<213> ORGANISM: Artificial Sequence
<220> FEATURE:
<223> OTHER INFORMATION: Synthetic sequence containing ZFN9476

<400> SEQUENCE: 136

```
gcaaagtccg gtcactgggc agcaccaccc cccggacttg catgggtagc cgctgagatg    60
gagcctgagc acgtgaca g                                                81
```

<210> SEQ ID NO 137
<211> LENGTH: 81
<212> TYPE: DNA
<213> ORGANISM: Artificial Sequence
<220> FEATURE:
<223> OTHER INFORMATION: Synthetic sequence containing ZFN9477

<400> SEQUENCE: 137

```
ctgtcacgtg tgctcaggct ccatctgagc ggctacccat gcaagtccgg ggggtggtgc    60
tgcccagtga ccggactttg c                                              81
```

<210> SEQ ID NO 138
<211> LENGTH: 114
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 138

```
atcggcaaga acggagacct tccctggcca atgctcaggt actggctgga ttgggcactg    60
ggcagcacca ccccccggac ttgcatgggt agccgctgag atggagcctg agca         114
```

<210> SEQ ID NO 139
<211> LENGTH: 63
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 139

```
atcggcaaga acggagacct tccctggcct tgcatgggta gccgctgaga tggagcctga    60
gca                                                                  63
```

<210> SEQ ID NO 140
<211> LENGTH: 62
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 140

```
atcggcaaga acggagacct tccctggctt gcatgggtag ccgctgagat ggagcctgag    60
ca                                                                   62
```

<210> SEQ ID NO 141
<211> LENGTH: 62
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 141
atcggcaaga acggagacct tccctggctt gcatgggtag ccgctgagat ggagcctgag      60
ca                                                                    62

<210> SEQ ID NO 142
<211> LENGTH: 58
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 142
atcggcaaga acggagacct tccctggcat gggtagccgc tgagatggag cctgagca        58

<210> SEQ ID NO 143
<211> LENGTH: 56
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 143
atcggcaaga acggagacct tccctggcgg gtagccgctg agatggagcc tgagca          56

<210> SEQ ID NO 144
<211> LENGTH: 56
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 144
atcggcaaga acggagacct tcccttgcgg gtagccgctg agatggagcc tgagca          56

<210> SEQ ID NO 145
<211> LENGTH: 54
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 145
atcggcaaga acggagacct tccctggcgt agccgctgag atggagcctg agca            54

<210> SEQ ID NO 146
<211> LENGTH: 50
<212> TYPE: DNA
<213> ORGANISM: Artificial Sequence
<220> FEATURE:
<223> OTHER INFORMATION: Synthetic sequence resulting from sequencing of
      genomic DHFR locus from ZFN transfected cells

<400> SEQUENCE: 146
atcggcaaga acggagacct tccctgagcc gctgagatgg agcctgagca                 50

<210> SEQ ID NO 147
<211> LENGTH: 45
<212> TYPE: DNA
<213> ORGANISM: Artificial Sequence
<220> FEATURE:
<223> OTHER INFORMATION: Synthetic sequence resulting from sequencing of
genomic DHFR locus from ZFN transfected cells

<400> SEQUENCE: 147
atcggcaaga acggagacct tccccgctga gatggagcct gagca                    45

<210> SEQ ID NO 148
<211> LENGTH: 56
<212> TYPE: DNA
<213> ORGANISM: Artificial Sequence
<220> FEATURE:
<223> OTHER INFORMATION: Synthetic sequence resulting from sequencing of
genomic DHFR locus from ZFN transfected cells

<400> SEQUENCE: 148
atcggcaaga acggagacct tcttgcatgg gtagccgctg agatggagcc tgagca        56

<210> SEQ ID NO 149
<211> LENGTH: 53
<212> TYPE: DNA
<213> ORGANISM: Artificial Sequence
<220> FEATURE:
<223> OTHER INFORMATION: Synthetic sequence resulting from sequencing of
genomic DHFR locus from ZFN transfected cells

<400> SEQUENCE: 149
atcggcaaga acggagacct tgcatgggta gccgctgaga tggagcctga gca           53

<210> SEQ ID NO 150
<211> LENGTH: 35
<212> TYPE: DNA
<213> ORGANISM: Artificial Sequence
<220> FEATURE:
<223> OTHER INFORMATION: Synthetic sequence resulting from sequencing of
genomic DHFR locus from ZFN transfected cells

<400> SEQUENCE: 150
atcggcaaga acggagacct tatggggcct gagca                               35

<210> SEQ ID NO 151
<211> LENGTH: 484
<212> TYPE: DNA
<213> ORGANISM: Cricetulus longicaudatus

<400> SEQUENCE: 151
aacattcagc tatgttaaag tatttgtgaa gtgttttgaa atgatttat atttctaag      60 gtgagaataa atgagaaaat gttttaatat gtctccagtg cccccatgac tagggatact   120
aattgagtac cagtacatta tcagtgtgct ctccacttct ccccagagtc catgtcagac   180
gcactgacaa agtgggaaca gaagcagcct tccatcccat tgaggaatac atggtacacg   240
ttgaagaaca ttttcagctt ctcgaacgca gaatgaaagt ggataaaaaa agagtgtatc   300
tggccactga tgacccttct ttgttaaagg aggcaaagac aaagtaagtt agaccaacaa   360
gtggttctgt atgggattat ctcttagttg aagaaaatcc ttaattctgg gaacttgtgg   420
ttcttgttgc taactaatag gttccaaaat caaagactac atgtgcaaat attaatctaa   480
tcaa                                                                484

<210> SEQ ID NO 152

```
<211> LENGTH: 68
<212> TYPE: DNA
<213> ORGANISM: Artificial Sequence
<220> FEATURE:
<223> OTHER INFORMATION: Synthetic sequence containing ZFN12172

<400> SEQUENCE: 152
ataaaaaaag agtgtatctg gccactgatg acccttcttt gttaaaggag gcaaagacaa      60
agtaagtt                                                              68

<210> SEQ ID NO 153
<211> LENGTH: 68
<212> TYPE: DNA
<213> ORGANISM: Artificial Sequence
<220> FEATURE:
<223> OTHER INFORMATION: Synthetic sequence containing ZFN12176

<400> SEQUENCE: 153
aacttacttt gtctttgcct cctttaacaa agaagggtca tcagtggcca gatacactct      60
tttttat                                                               68

<210> SEQ ID NO 154
<211> LENGTH: 19
<212> TYPE: DNA
<213> ORGANISM: Artificial Sequence
<220> FEATURE:
<223> OTHER INFORMATION: Synthetic zinc finger target sequence: ZFN
      12176

<400> SEQUENCE: 154
caaagaaggg tcatcagtg                                                  19

<210> SEQ ID NO 155
<211> LENGTH: 22
<212> TYPE: DNA
<213> ORGANISM: Artificial Sequence
<220> FEATURE:
<223> OTHER INFORMATION: Synthetic zinc finger target sequence: ZFN
      12172

<400> SEQUENCE: 155
taaaggaggc aaagacaaag ta                                              22

<210> SEQ ID NO 156
<211> LENGTH: 80
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 156
ctttggtttt gtgggcaaca tgctggtcat cctcatcctg ataaactgca aaaggctgaa      60
gagcatgact gacatctacc                                                 80

<210> SEQ ID NO 157
<211> LENGTH: 77
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 157
ctttggtttt gtgggcaaca tgctggtcat cctcctgata aactgcaaaa ggctgaagag      60
```

```
catgactgac atctacc                                             77

<210> SEQ ID NO 158
<211> LENGTH: 68
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 158
ctttggtttt gtgggcaaca tgctggtcat cctcatcaaa aggctgaaga gcatgactga   60
catctacc                                                           68

<210> SEQ ID NO 159
<211> LENGTH: 80
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 159
ctttggtttt gtgggcaaca tgctggtcat cctcatcctg atctgataaa ctgcaaaagg   60
ctgaagagca tgactgacat                                              80

<210> SEQ ID NO 160
<211> LENGTH: 80
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 160
gaccagatgt aagctctcct ccatccagct cctcaacagc aacaacagga ccacctccca   60
aactctgcct ggtgtgctct                                              80

<210> SEQ ID NO 161
<211> LENGTH: 78
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 161
gaccagatgt aagctctcct ccatccagct cctcaagcaa caacaggacc acctcccaaa   60
ctctgcctgg tgtgctct                                                78

<210> SEQ ID NO 162
<211> LENGTH: 71
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 162
gaccagatgt aagctctcct ccatccagct cctcaacagg accacctccc aaactctgcc   60
tggtgtgctc t                                                       71

<210> SEQ ID NO 163
<211> LENGTH: 68
```

```
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 163
gaccagatgt aagctctcct ccatccagct cctcaggacc acctcccaaa ctctgcctgg    60
tgtgctct                                                             68

<210> SEQ ID NO 164
<211> LENGTH: 80
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 164
ctgggtactt ttatctgtcc cctccacccc acagtggggc cactagggac aggattggtg    60
acagaaaagc cccatcctta                                                80

<210> SEQ ID NO 165
<211> LENGTH: 61
<212> TYPE: DNA
<213> ORGANISM: Artificial Sequence
<220> FEATURE:
<223> OTHER INFORMATION: Synthetic sequence resulting from knockout
      clone analysis

<400> SEQUENCE: 165
ctgggtactt ttatctgtcc cctccacccc acagattggt gacagaaaag cccatcctt     60 a                                                                    61

<210> SEQ ID NO 166
<211> LENGTH: 70
<212> TYPE: DNA
<213> ORGANISM: Cricetulus longicaudatus

<400> SEQUENCE: 166
tttgcagcgc agtccttctc cagtaccatc aacccagata tacatggctt ggactttctc    60
accctggggc                                                           70

<210> SEQ ID NO 167
<211> LENGTH: 70
<212> TYPE: DNA
<213> ORGANISM: Homo sapiens

<400> SEQUENCE: 167
cttgcagcgc agtccttctc cagtaccatc gatccagata tacatggcct ggactttctc    60
accctgaggc                                                           70

<210> SEQ ID NO 168
<211> LENGTH: 70
<212> TYPE: DNA
<213> ORGANISM: Mus musculus

<400> SEQUENCE: 168
cttgcagcgc agtccttctc cggtaccatc aacccagata tacatggctt ggactttctc    60
accctggggc                                                           70

<210> SEQ ID NO 169
```

-continued

<211> LENGTH: 69
<212> TYPE: DNA
<213> ORGANISM: Rattus sp.

<400> SEQUENCE: 169
attgcagcat agtccttctc cagcaccatt gacctagata tacatggctt ggatttctca    60
ccctaagcc    69

<210> SEQ ID NO 170
<211> LENGTH: 70
<212> TYPE: DNA
<213> ORGANISM: Canine sp.

<400> SEQUENCE: 170
cttgcaacgt aatccttctc cagtcccgtc aatccaaata tacatagctt gcactttctc    60
gccctgaggc    70

<210> SEQ ID NO 171
<211> LENGTH: 70
<212> TYPE: DNA
<213> ORGANISM: Didelphis sp.

<400> SEQUENCE: 171
tttacagcgc agaccctcat cagtgccatc aatccagata tacatagcct ggactttgtt    60
gccttgaggc    70

<210> SEQ ID NO 172
<211> LENGTH: 70
<212> TYPE: DNA
<213> ORGANISM: Gallus sp.

<400> SEQUENCE: 172
tttgcagcgg aggtgctccc cagtcccgtc gatccagatg tacatggctt ggaccttctc    60
ccctgcggc    70

<210> SEQ ID NO 173
<211> LENGTH: 70
<212> TYPE: DNA
<213> ORGANISM: X. tropicalis

<400> SEQUENCE: 173
cttgcagcga agaccctccc cggtcccatc aacccagatg tacatagcct gcaccttatc    60
tccctgtggc    70

<210> SEQ ID NO 174
<211> LENGTH: 70
<212> TYPE: DNA
<213> ORGANISM: Tetraodon sp.

<400> SEQUENCE: 174
tttgcagcgt agtccttctc ctgttccatc aatccaaata tacatggcct gaactttatc    60
ccctgtggg    70

<210> SEQ ID NO 175
<211> LENGTH: 70
<212> TYPE: DNA
<213> ORGANISM: Cricetulus longicaudatus

<400> SEQUENCE: 175
gctaaagttg gtatggcagc ctgcaccatt ccagttccca ggaatgggct tggggtcaaa    60

-continued

```
ggttgctatt                                                            70

<210> SEQ ID NO 176
<211> LENGTH: 70
<212> TYPE: DNA
<213> ORGANISM: Homo sapiens

<400> SEQUENCE: 176
gctgaagttg gtatggcagc ctgcaccatt ccagttccca ggaatgggct taggatcaaa     60
ggttgctatc                                                            70

<210> SEQ ID NO 177
<211> LENGTH: 70
<212> TYPE: DNA
<213> ORGANISM: Mus musculus

<400> SEQUENCE: 177
gctgaagttg gtatggcagc ctgcaccatt ccagttccct ggaatgggct tggggtcaaa     60
ggttgctatc                                                            70

<210> SEQ ID NO 178
<211> LENGTH: 70
<212> TYPE: DNA
<213> ORGANISM: Rattus sp.

<400> SEQUENCE: 178
gctaaaattg atttatcagc ctgcactatc accattctca agactcagtc ttggatcaaa     60
ggtcactatt                                                            70

<210> SEQ ID NO 179
<211> LENGTH: 70
<212> TYPE: DNA
<213> ORGANISM: Canine sp.

<400> SEQUENCE: 179
gctgaagttg gtgtggcagc ctgcaccatt ccagtttccg ggaatgggct taggatcaaa     60
ggttgctatc                                                            70

<210> SEQ ID NO 180
<211> LENGTH: 70
<212> TYPE: DNA
<213> ORGANISM: Didelphis sp.

<400> SEQUENCE: 180
actgaagtta gtgtggcaac cagctccatt ccagttccca gggattggct tgggatcaaa     60
tgatacaatc                                                            70

<210> SEQ ID NO 181
<211> LENGTH: 70
<212> TYPE: DNA
<213> ORGANISM: Gallus sp.

<400> SEQUENCE: 181
gctgaagttg gtgtgacagc cagcaccgtt ccagttccca gggatgggtt tgggatcgaa     60
ggacacaatg                                                            70

<210> SEQ ID NO 182
<211> LENGTH: 70
<212> TYPE: DNA
<213> ORGANISM: X. tropicalis
```

```
<400> SEQUENCE: 182
actgtagttg gtatggcaac cagcgccgtt ccagtttccg gtcatgggct tggggtccag    60
cgtggccacc                                                          70

<210> SEQ ID NO 183
<211> LENGTH: 70
<212> TYPE: DNA
<213> ORGANISM: Tetraodon sp.

<400> SEQUENCE: 183
gctgaagttt gtatggcagc cagcaccgtt ccagttccct gggattggct tggggtcaaa    60
tgaggcaatg                                                          70

<210> SEQ ID NO 184
<211> LENGTH: 70
<212> TYPE: DNA
<213> ORGANISM: Fugu rubripes

<400> SEQUENCE: 184
gctgaagttg gtatggcagc cggcgccgtt ccagttcccg gagatcggtt tggggtcgaa    60
ggaggcgacg                                                          70

<210> SEQ ID NO 185
<211> LENGTH: 70
<212> TYPE: DNA
<213> ORGANISM: Danio rerio

<400> SEQUENCE: 185
gttgaagtta gtgtggcaac cagcaccatt ccagttgcct gggatcggct taggatcaaa    60
tgaagctacc                                                          70
```

METHODS AND COMPOSITIONS FOR INACTIVATING GLUTAMINE SYNTHETASE GENE EXPRESSION

CROSS-REFERENCE TO RELATED APPLICATIONS

The present application claims the benefit of U.S. Provisional Application No. 61/197,600, filed Oct. 29, 2008, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of genome engineering, cell culture, generation of cell lines and protein production.

BACKGROUND

Glutamine synthetase (GS) is a critical enzyme in the synthesis of the amino acid L-glutamine. See, Meister, A. in *Glutamine Metabolism, Enzymology and Regulation* (eds. J. Mora & R. Palacios) 1-40 (Academic Press, N.Y.; 1980). A GS-negative cell line is therefore auxotrophic for L-glutamine. GS is frequently used as a selection marker gene in CHO cell based recombinant protein expression systems (Wurm et al. (2004)*Nature Biotechnology* 22: 1393-1398), though the absence of a GS-negative CHO line requires the use of the GS inhibitor methionine sulfoximine to achieve selection.

In addition, dihydrofolate reductase (DHFR, 5,6,7,8-tetrahydrofolate:NADP+oxidoreductase) is an essential enzyme in both eukaryotes and prokaryotes and catalyzes the NADPH-dependent reduction of dihydrofolate to tetrahydrofolate, an essential carrier of one-carbon units in the biosynthesis of thymidylate, purine nucleotides, glycine and methyl compounds.

DHFR-deficient cells have long been used for production of recombinant proteins. DHFR-deficient cells will only grow in medium supplemented by certain factors involved in folate metabolism or if DHFR is provided to the cell, for example as a transgene. Cells into which a DHFR transgene has been stably integrated can be selected for by growing the cells in unsupplemented medium. Moreover, exogenous sequences are typically co-integrated when introduced into a cell using a single polynucleotide. Accordingly, when the DHFR transgene also includes a sequence encoding a protein of interest, selected cells will express both DHFR and the protein of interest. Furthermore, in response to inhibitors such as methotrexate (MTX), the DHFR gene copy number can be amplified. Accordingly, sequences encoding a protein of interest that are co-integrated with exogenous DHFR can be amplified by gradually exposing the cells to increasing concentrations of methotrexate, resulting in overexpression of the recombinant protein of interest. However, despite the wide use of DHFR-deficient cell systems for recombinant protein expression, currently available DHFR-deficient cell lines do not grow as well as the parental DHFR-competent cells from which they are derived.

Thus, mammalian cells with single and multi-gene knockouts have enormous utility in research, drug discovery, and cell-based therapeutics. However, conventional methods for the targeted elimination of an investigator-specified gene rely upon the process of homologous recombination or gene targeting. Mansour et al. (1988) *Nature* 336:348-352; Vasquez et al. (2001) *Proc Natl Acad Sci USA* 98:8403-8410; Rago et al. (2007) *Nature Protocols* 2:2734-2746; Kohli et al. (2004) *Nucleic Acids Research* 32, e3. While capable of generating a defined biallelic knockout, for many cell types this technique has proven too inefficient and thus too laborious for routine application. See, e.g, Yamane-Ohnuki et al. (2004) *Biotechnol Bioeng* 87:614-622. These methods for targeted gene deletion require sequential rounds of homologous recombination and drug selection to isolate rare desired events—a process sufficiently laborious to limit application to individual loci. Consequently, the generation of mammalian cell lines modified at multiple target loci has been largely unexplored.

Zinc-finger nucleases (ZFNs) have been used for targeted cleavage and gene inactivation. See, for example, United States Patent Publications 20030232410; 20050208489; 20050026157; 20050064474; 20060188987; 20060063231; 2008/0015164 and U.S. Ser. No. 12/218,035 and International Publication WO 07/014,275, the disclosures of which are incorporated by reference in their entireties for all purposes. Formed via the fusion of an engineered zinc-finger DNA binding domain specific for a designated target sequence and the catalytic domain of Fok I (a restriction endonuclease from *Flavobacterium okeanokoites*), ZFNs provide the ability to place a double-strand DNA break (DSB) at a chosen genomic address. The removal of this site-specific DSB is carried out by the cell's own DNA repair machinery either via a homology-directed repair process when donor DNA is provided, or via non-homologous end joining (NHEJ). See, e.g., Urnov et al. (2005) *Nature* 435:646-651 (2005); Moehle et al. (2007) *Proc Natl Acad Sci USA* 104: 3055-3060 (2007); Bibikova, et al. (2001) *Mol Cell Biol* 21:289-297; Bibikova et al. (2003) *Science* 300:764; Porteus et al. (2005) *Nature Biotechnology* 23:967-973; Lombardo et al. (2007) *Nature Biotechnology* 25:1298-1306; Perez et al. (2008) *Nature Biotechnology* 26:808-816; Bibikova et al. (2002) *Genetics* 161:1169-1175; Lloyd et al. (2005) *Proc Natl Acad Sci USA* 102:2232-2237; Morton et al. (2006) *Proc Natl Acad Sci USA* 103:16370-16375.

While both homology-directed repair and NHEJ processes result in the modification of the target locus, the NHEJ-driven approach obviates the need for donor DNA design and synthesis yet results in a high frequency of disrupted alleles and the error-prone nature of the NHEJ-mediated DSB repair can be exploited to achieve the knockout of a targeted gene in mammalian cells following simple transient transfection of a DNA construct encoding the ZFNs. See, e.g., Santiago et al. (2008) *Proc Natl Acad Sci USA* 105:5809-5814. ZFN technology has allowed the isolation of several independent knockout cell lines from a screening effort of less than one 96-well plate of single-cell derived clones. As no donor DNA or selection strategy was employed, the resultant single-gene knock out line is a suitable starting cell line for subsequent genetic modification.

SUMMARY

Disclosed herein are compositions for the partial or complete inactivation of a GS gene. Also disclosed herein are methods of making and using these compositions (reagents), for example to inactivate GS in a cell to produce cell lines in which a GS gene is inactivated. GS disrupted cell lines are useful, for example, in production of recombinant proteins.

In one aspect, zinc finger proteins, engineered to bind in a GS gene, are provided. Any of the zinc finger proteins described herein may include 1, 2, 3, 4, 5, 6 or more zinc fingers, each zinc finger having a recognition helix that binds to a target subsite in a GS gene. In certain embodiments, the zinc finger proteins comprise 4, 5 or 6 fingers (wherein the individual zinc fingers are designated F1, F2, F3, F4, F5 and F6) and comprise the amino acid sequence of the recognition helices shown in Table 1.

In another aspect, zinc finger proteins, engineered to bind in a DHFR gene, are provided. Any of the zinc finger proteins described herein may include 1, 2, 3, 4, 5, 6 or more zinc fingers, each zinc finger having a recognition helix that binds to a target subsite in a DHFR gene. In certain embodiments, the zinc finger proteins comprise 4, 5 or 6 fingers (wherein the individual zinc fingers are designated F1, F2, F3, F4, F5 and F6) and comprise the amino acid sequence of the recognition helices shown in Table 2.

In another aspect, fusion proteins comprising any of the zinc finger proteins described herein and at least one cleavage domain or at least one cleavage half-domain, are also provided. In certain embodiments; the cleavage half-domain is a wild-type FokI cleavage half-domain. In other embodiments, the cleavage half-domain is an engineered FokI cleavage half-domain.

In yet another aspect, a polynucleotide encoding any of the proteins described herein is provided.

In yet another aspect, also provided is an isolated cell comprising any of the proteins and/or polynucleotides as described herein. In certain embodiments, GS is inactivated (partially or fully) in the cell. Any of the cells described herein may include additional genes that have been inactivated, for example, using zinc finger nucleases designed to bind to a target site in the selected gene. In certain embodiments, provided herein are cells or cell lines in which FUT8, dihydrofolate reductase (DHFR) and glutamine synthetase (GS) have been inactivated.

In addition, methods of using the zinc finger proteins and fusions thereof in methods of inactivating GS in a cell or cell line are provided.

Thus, in another aspect, provided herein is a method for inactivating a cellular GS gene (e.g., an endogenous GS gene) in a cell, the method comprising: (a) introducing, into a cell, a first nucleic acid encoding a first polypeptide, wherein the first polypeptide comprises: (i) a zinc finger DNA-binding domain that is engineered to bind to a first target site in an endogenous GS gene; and (ii) a cleavage domain; such that the polypeptide is expressed in the cell, whereby the polypeptide binds to the target site and cleaves the GS gene. In certain embodiments, the methods further comprise introducing a nucleic acid encoding a second polypeptide, wherein the second polypeptide comprises: (i) a zinc finger DNA-binding domain that is engineered to bind to a second target site in the GS gene; and (ii) a cleavage domain; such that the second polypeptide is expressed in the cell, whereby the first and second polypeptides bind to their respective target sites and cleave the GS gene. The first and second polypeptides may be encoded by the first nucleic acid or by different nucleic acids. In certain embodiments, one or more additional polynucleotides or polypeptides are introduced into the cells, for example polynucleotides encoding additional zinc finger proteins.

In yet another aspect, the disclosure provides a method of producing a recombinant protein of interest in a host cell, the method comprising the steps of: (a) providing a host cell comprising an endogenous GS gene; (b) inactivating the endogenous GS gene of the host cell by any of the methods described herein; and (c) introducing an expression vector comprising a transgene, the transgene comprising a sequence encoding a protein of interest, into the host cell, thereby producing the recombinant protein. In certain embodiments, the protein of interest comprises an antibody, e.g., a monoclonal antibody.

In any of the cells and methods described herein, the cell or cell line can be for example, but not limited to a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), NIH3T3, perC6, insect cell such as *Spodoptera fugiperda* (Sf), or fungal cell such as *Saccharomyces, Pichia* and *Schizosaccharomyces*.

BRIEF DESCRIPTION OF THE DRAWINGS

Figures 1C, 1D:
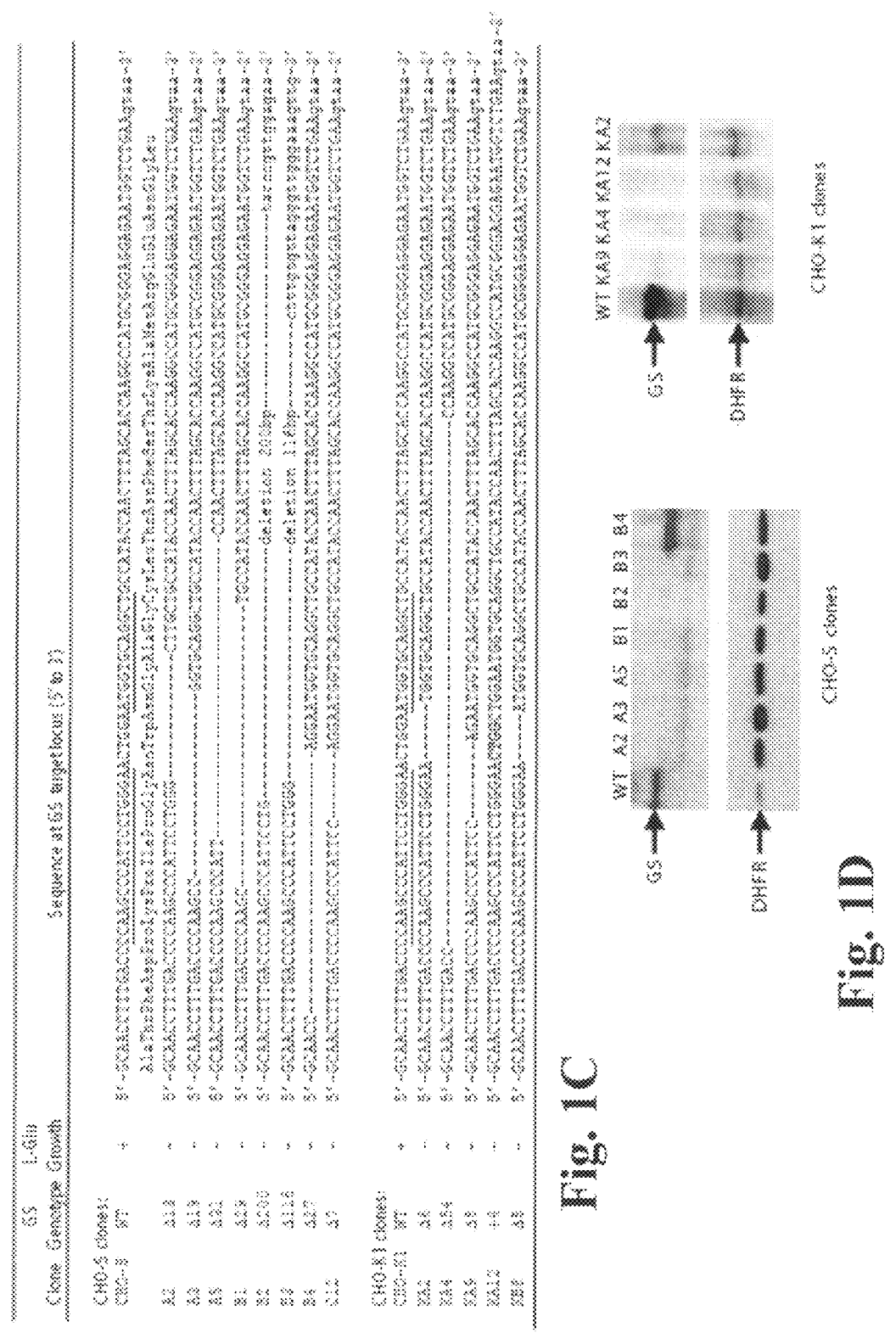

FIG. 1, panels A to E, show ZFN-mediated disruption of the glutamine synthetase gene in CHO cells and generation of single knockout GS−/− cell lines. FIG. 1A is a schematic depicting the actively-transcribed GS gene, which contains 7 exons. The start codon ATG located in exon 2. FIG. 1A also shows that the target sequence for ZFN pair ZFN9372/ZFN9075 is located in exon 6 as indicated and that the target sequence of ZFN pair 8361/8365 is located in exon 2. Additional ZFNs (9076, 9179, 7858, 7889, 9373) targeted to exon 6 are also shown. FIG. 1B are gels showing ZFN-mediated disruption of the endogenous CHO GS gene using ZFN pair 9372/9075 linked to either the wild-type or an obligate heterodimer EL/KK variant of the catalytic domain of Fok I in CHO-K1 cells (left panel) or CHO-S cells (right panel), as determined by the Surveyor™ Nuclease Assay. FIG. 1C (SEQ ID NOS: 58-73, respectively) depicts exemplary DNA sequences of the target GS locus for the indicated cell lines along with their growth properties in the absence of exogenously added L-glutamine ("L-Glu Growth"; '+': growth in the absence of L-glutamine indistinguishable from wild-type CHO; '−': no growth in the absence of L-glutamine). The ZFN target sequences are underlined. The protein translation is shown under the wild-type sequence. Capital letters indicate exonic sequences, small letters indicate intronic sequences, '–' indicate deletions, bold letters indicate insertions. FIG. 1D depicts Western blot analysis of selected CHO-S (left panel) and CHO-K1 (right panel) cell lines using an anti-GS monoclonal antibody (top panels). As a loading control, blots were re-probed with an anti-DHFR antibody (bottom panels).

FIG. 2, panels A to F, depict ZFN-mediated disruption of the DHFR gene in CHO cells and generation of double knockout DHFR−/−GS−/− cell lines. FIG. 2A shows the genomic organization of the DHFR gene in CHO cells and the location of the target sites for ZFN pairs 9461/7844 (in exon 1, see, U.S. Patent Application No. 20080015164) and 9476/9477 (in intron 1 located 240-bp 3' of the exon 1 ZFN 9461/7844 cleavage site). FIG. 2B depicts the level of gene modification using ZFN pair 9461/7844 (left panel) and ZFN pair 9476/

9477 (right panel), as measured using the Surveyor™ Nuclease Assay. FIG. 2C depicts PCR analysis of GS−/− clone B3 genomic DNA 2 days after concurrent transfection of plasmids encoding both ZFN pairs, which resulted in a deletion of approximately 240 bp in the DHFR locus (small arrow in lane 7). Serving as controls were cells transfected with empty vector (Lane 1), a GFP control vector (Lane 2), the exonic ZFN pair only (ZFN9461/ZFN7844, Lane 3), the intronic ZFN pair only (ZFN9476/ZFN9477, Lane 4), the "inner" ZFNs relative to the deletion (ZFN7844 and ZFN9477, LaneS), and the "outer" ZFNs relative to the deletion (ZFN9461 and ZFN9476, Lane 6).

FIG. 3, panels A to D, show ZFN-mediated disruption of the FUT8 gene in CHO cells and generation of triple knockout FUT8−/−DHFR−/−GS−/− cell lines. FIG. 3A is a schematic depicting ZFNs targeted to the critical and highly conserved region encoding the FUT8 Fut motif II located in exon 10. See, also, U.S. patent application Ser. No. 12/218,0135. FIG. 3B depicts the level of gene modification 2 days after transient transfection of the ZFN pair 12176/12172 into the DHFR−/−GS−/− clone 1F1.6, as measured using the Surveyor™ Nuclease Assay. FIG. 3C depicts. fluorescent-LCA binding activity of the triple-KO clones 35F2 and 14C1 (lines on left side of panel) by FACS analysis. F-LCA stained wild-type CHO-S cells (line on right side of panel) served as positive controls, and unstained cells (dotted line) served as negative controls. FIG. 3D (SEQ ID NOS: 82-87, respectively) shows the genotype (for both alleles) of the triple-knockout cell lines 35F2 and 14C1 at the FUT8 locus where the sequence shown is for both alleles. Capital letters indicate exon 10 sequences, small letters indicates intron sequences, italic letters indicate Fut motif II sequences, bold letters indicate sequence insertions, '−' indicates deletions. The protein translation is also shown under the wild-type sequence. Underline indicates the ZFN binding sites.

FIG. 4, panels A to C, depict an exemplary ZFN design and its target site in the CHO GS gene. FIG. 4B (SEQ ID NOS: 89 and 90 is a schematic representation of ZFN9372 and ZFN9075 binding to their double-stranded target sequence (underlined). FIG. 4C depicts the target sequences and zinc-finger designs of ZFN9372 (SEQ ID NOS: 6-12) and ZFN9075 (SEQ ID NOS: 1-5). The core DNA target sequences (capital letters) and 2 flanking bases (small letters) are shown. ZFN9075 contains 4 zinc-finger DNA-binding domains, and ZFN9372 contains 6 zinc-finger domains. The amino acid residues at positions '−1' to '+6' of the recognition a-helix of each of the zinc-finger DNA-binding domains for the indicated target DNA triplets are shown.

FIG. 5 (SEQ ID NOS: 91-132, respectively) shows exemplary results of sequencing of the genomic GS locus from ZFN transfected cells. "C" refers to the count (number of times the indicated sequence was observed) and "G" refers to the genotype. The ZFN target sequences are underlined. Bold letters indicate sequence insertions, '−' indicates deletions.

FIG. 7, panels A to C, depict exemplary ZFN designs and their target sites in the CHO DHFR gene. FIG. 7A (SEQ ID NO: 133) shows the nucleotide sequence of the DHFR region targeted by the indicated ZFN pairs in CHO cells. Capital letters indicate exon sequences, small letters indicate intron sequences. FIG. 7C shows the target sequences (SEQ ID NOS: 33, 32, 38, and 41, respectively) and zinc-finger designs (SEQ ID NOS: 37, 36, 35, 34, 25, 2, 3, 14, 40, 14, 39, 2, 43, 42, 17, and 7, respectively) of exemplary ZFNs targeting the CHO DHFR gene. The core DNA target sequences (capital letters) and 2 flanking bases (small letters) are shown. All ZFNs contain 4 zinc-finger DNA-binding domains. The amino acid residues at positions '−1' to '−6' of the recognition α-helix for each of the zinc-finger DNA-binding domains for the indicated target DNA triplet are shown.

FIG. 8 (SEQ ID NOS: 138-150, respectively) shows exemplary results of sequencing of the genomic DHFR locus from ZFN transfected cells. "C" refers to the count (number of times the indicated sequence was observed) and "G" refers to the genotype. The ZFN target sequences are underlined. Bold letters indicate sequence insertions, '−' indicates deletions. Bold letters indicate sequence insertions. Italics indicate sequence changes. Capital letters indicate exonic sequence, small letters indicate intronic sequence.

FIG. 9, panels A to C, depict ZFN target sites and finger designs targeted to the CHO FUT8 gene. FIG. 9C depicts the target sequences (SEQ ID NOS: 154 and 155) and zinc-finger designs (SEQ ID NOS: 54, 53, 52, 51, 3, 49, 48, 47, 9, 46, and 45, respectively) of ZFN12176 and ZFN12172. The core DNA target sequences (capital letters) and 2 flanking bases (small letters) are shown. ZFN12176 contains 5 zinc-finger DNA-binding domains, and ZFN12172 contains 6 zinc-finger domains. The amino acid residues at positions '−1' to '+6' of the recognition α-helix for each of the zinc-finger DNA-binding domains for the indicated target DNA triplet are shown.

FIG. 10, panels A to C, show ZFN targeting of CCR5, GR and AAVS1 loci. FIG. 10A is a schematic showing the location of ZFN targeting sites in C-C chemokine receptor 5 (CCR5), glucocorticoid receptor (GR), and adeno-associated virus integration site (AAVS1) loci, respectively. FIG. 10B depicts ZFN-mediated simultaneous disruption, as measured by Surveyor™ Nuclease Assay, of CCR5 (left panel), GR (middle panel), and AAVS1 (right panel) loci as measured 20 days after transient co-transfection of pairs of ZFNs linked to either the wild-type, ZFN-Fok I (wt) or an obligate heterodimer EL/KK variant, ZFN-Fok I(EL/KK), of the catalytic domain of Fok into K562 cells. Treatments for each lane are as following: lane1, CCR5 ZFN-FokI (wt); lane 2, GR ZFN-Fok I(wt); lane 3, AAVS1 ZFN-Fok I(wt); lane 4, CCR5 ZFN-Fok I(EL/KK); lane 5, GR ZFN-Fok I(EL/KK); lane 6, AAVS1 ZFN-Fok I(EL/KK); lane 7, CCR5 ZFN-FokI(wt)+GR ZFN-FokI(wt)+AAVS1 ZFN-FokI(wt); lane 8, CCR5 ZFN-FokI(EL/KK)+GR ZFN-FokI(EL/KK)+AAVS1 ZFN-FokI(EL/KK). FIG. 10C (SEQ ID NOS: 156-165, respectively) depicts the genotype of a single triple knockout clone wherein the target CCR5, GR, AAVS1 loci for the indicated cell lines are shown. The ZFN target sequences are underlined. '–' indicate deletions, bold letters indicate insertions.

FIG. 11, panels A and B, show sequence alignments of CHO GS genomic sequences as determined herein with the indicated species. FIG. 11A (SEQ ID NOS: 166-174, respectively) shows alignment of exon 2 sequence. The target sites for ZFN8361 and ZFN8365 are underlined. FIG. 11B (SEQ ID NOS: 175-185, respectively) shows alignment of exon 6 sequence. The target sites for ZFN9075 and ZFN9372 are underlined.

FIG. 12, panels A to D, show ZFN-mediated disruption in human and mouse cells. FIGS. 12A and B show disruption of GS in human K562 mediated by ZFNs targeted to exon 2 of CHO GS (FIG. 12A) and exon 6 of CHO GS (FIG. 12B). FIGS. 12C and D show disruption of GS in mouse Neuro2a cells mediated by ZFNs targeted to exon 2 of CHO GS (FIG. 12C) and exon 6 of CHO GS (FIG. 12D).

FIG. 13, panels A to C, show the complete genomic sequence of CHO GS locus (SEQ ID NO:55). Introns and exons are designated as shown.

FIG. 14, panels A to C, show the results of GS-specific gene targeting in HEK293 cells.

DETAILED DESCRIPTION

Figure 1E:
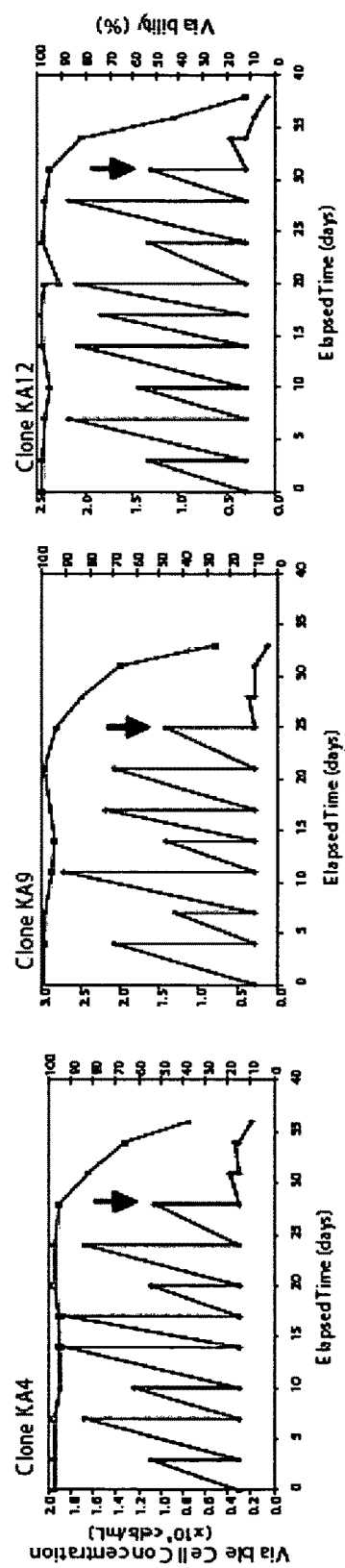
FIG. 1E shows graphs depicting growth and viability of selected CHO-K1 GS−/− cell lines that had been grown for period of approximately 3 months. The viability (smooth line on the top of the graph) and viable cell density (jagged line) of these cell lines is shown for a 30 day period following the initial 3 month period, where cells were grown in L-glutamine-supplemented medium, splitting the cells every 2-3 days. L-glutamine was withdrawn at the time indicated by the arrow.

Described herein are compositions and methods for partial or complete inactivation of a GS gene. Also disclosed are methods of making and using these compositions (reagents), for example to inactivate a GS gene in a target cell. Inactivation of GS, alone or in combination with other genes such as DHFR and FUT8 in a target cell can be used to produce cell lines for expression of recombinant proteins, for example monoclonal antibodies that elicit enhanced antibody-dependent cellular cytotoxicity (ADCC).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (IQ of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970; WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a' mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more-preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art.

Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528 and 2008/0131962, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. An exogeneous molecule can also be the same type of molecule as an endogenous molecule but derived from a different species than the cell is derived from. For example, a human nucleic acid sequenced may be introduced into a cell line originally derived from a mouse or hamster.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also refer to a nucleic acid from a different species, for example, a human gene inserted into a hamster genome.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, shRNAs, micro RNAs (miRNAs) ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be complete (knock-out) or partial (e.g., a hypomorph in which a gene exhibits less than normal expression levels or a product of a mutant gene that shows partial reduction in the activity it influences).

"Eucaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

The term "antibody" as used herein includes antibodies obtained from both polyclonal and monoclonal preparations, as well as, the following: hybrid (chimeric) antibody molecules (see, for example, Winter et al., Nature (1991) 349: 293-299; and U.S. Pat. No. 4,816,567); F(ab')$_2$ and F(ab) fragments; Fv molecules (non-covalent heterodimers, see, for example, Inbar et al., Proc Natl Acad Sci USA (1972) 69:2659-2662; and Ehrlich et al., Biochem (1980) 19:4091-4096); single-chain Fv molecules (sFv) (see, for example, Huston et al., Proc Natl Acad Sci USA (1988) 85:5879-5883); dimeric and trimeric antibody fragment constructs; minibodies (see, e.g., Pack et al., Biochem (1992) 31:1579-1584; Cumber et al., J Immunology (1992) 149B: 120-126); humanized antibody molecules (see, for example, Riechmann et al., Nature (1988) 332:323-327; Verhoeyan et al., Science (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

Zinc Finger Nucleases

Described herein are zinc finger nucleases (ZFNs) that can be used for inactivation of a GS gene. ZFNs comprise a zinc finger protein (ZFP) and a nuclease (cleavage) domain.

A. Zinc Finger Proteins

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Examples of additional linker structures are found in U.S. Provisional Application No. 61/130,099, filed May 28, 2008 and entitled Compositions For Linking DNA-Binding Domains And Cleavage Domains.

Table 1 describes a number of zinc finger binding domains that have been engineered to bind to nucleotide sequences in the GS gene. See, also, FIG. 1 and FIG. 3. Each row describes a separate zinc finger DNA-binding domain. The DNA target sequence for each domain is shown in the first column and the second through fifth columns show the amino acid sequence of the recognition region (amino acids −1 through +6, with respect to the start of the helix) of each of the zinc fingers (F1 through F4, F5 or F6) in the protein. Nucleotides shown in uppercase denote triplets that are directly targeted by a zinc finger and nucleotides shown in lower case denotes bases that are not directly targeted by a zinc finger (for example due to longer linkers between fingers which can result in "skipping" a base). Also provided in the first column is an identification number for the proteins.

TABLE 1

Zinc finger nucleases targeted to GS

| ZFN name Target sequence | F1 | F2 | F3 | F4 | F5 | F6 |
|---|---|---|---|---|---|---|
| ZFN 9075 gaATGGTGCAGGCTgc (SEQ ID NO: 1) | QSSDLSR (SEQ ID NO: 2) | RSDNLRE (SEQ ID NO: 3) | RSDTLSN (SEQ ID NO: 4) | RKDVRIT (SEQ ID NO: 5) | N/A | N/A |
| ZFN 9372 gtTCCCAGGAATGGG CTTGGgg (SEQ ID NO: 6) | RSDHLST (SEQ ID NO: 7) | QSSDLRR (SEQ ID NO: 8) | RSDHLSG (SEQ ID NO: 9) | QSANRTT (SEQ ID NO: 10) | RSDNLSQ (SEQ ID NO: 11) | ASNDRKK (SEQ ID NO: 12) |
| ZFN 8361 ctGGGTTGATGGTActg gagaaggactg (SEQ ID NO: 13) | QSGALAR (SEQ ID NO: 14) | RSDALTQ (SEQ ID NO: 15) | RSDSLSA (SEQ ID NO: 16) | RSAHLSR (SEQ ID NO: 17) | N/A | N/A |
| ZFN 8365 taTACATGGCTTGGact ttctcaccctg (SEQ ID NO: 18) | RSDHLST (SEQ ID NO: 7) | QSSDLRR (SEQ ID NO: 8) | RSDSLSV (SEQ ID NO: 19) | DNANRTK (SEQ ID NO: 20) | N/A | N/A |
| ZFN 9076 gaATGGTGCAGGCTgc cataccaacttt (SEQ ID NO: 21) | QSSDLSR (SEQ ID NO: 2) | RSDNLRE (SEQ ID NO: 3) | RSSALTR (SEQ ID NO: 22) | RSDALTQ (SEQ ID NO: 15) | N/A | N/A |
| ZFN 9179 ggAATGGTgCAGGCTg ccataccaactt (SEQ ID NO: 23) | QSSDLSR (SEQ ID NO: 2) | RSDNLRE (SEQ ID NO: 3) | QSSHLTR (SEQ ID NO: 24) | TSSNRKT (SEQ ID NO: 25) | N/A | N/A |
| ZFN 7858 gaATGGTGCAGGCTgc (SEQ ID NO: 1) | QSSDLSR (SEQ ID NO: 2) | RSDNLRE (SEQ ID NO: 3) | RSDSLLR (SEQ ID NO: 26) | RSDALTQ (SEQ ID NO: 15) | N/A | N/A |
| ZFN 7889 gtTCCCAGGAATGGgc (SEQ ID NO: 27) | RSDHLSQ (SEQ ID NO: 9) | QSANRTT (SEQ ID NO: 10) | RSDNLSQ (SEQ ID NO: 11) | ASNDRKK (SEQ ID NO: 12) | N/A | N/A |
| ZFN 9373 gtTCCCAGGAATGGgC TTGGGgtcaaag (SEQ ID NO: 28) | RSDHLSQ (SEQ ID NO: 9) | RNADRIT (SEQ ID NO: 29) | RSDHLSG (SEQ ID NO: 9) | QSANRTT (SEQ ID NO: 10) | RSDNLSQ (SEQ ID NO: 11) | ASNDRKK (SEQ ID NO: 12) |

As described below, in certain embodiments, a four-, five-, or six-finger binding domain as shown in Table 1 is fused to a cleavage half-domain, such as, for example, the cleavage domain of a Type IIs restriction endonuclease such as FokI. One or more pairs of such zinc finger/nuclease half-domain fusions are used for targeted cleavage, as disclosed, for example, in U.S. Patent Publication Nos. 20050064474 and 20070218528.

For targeted cleavage, the near edges of the binding sites can separated by 5 or more nucleotide pairs, and each of the fusion proteins can bind to an opposite strand of the DNA target. All pairwise combinations of the proteins shown in Table 1 can be used for targeted cleavage of a GS gene. Following the present disclosure, ZFNs can be targeted to any sequence in a GS gene.

B. Cleavage Domains

The ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endo-nucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., Si Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (O) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". As described in the examples a pair of ZFNs in which one ZFN comprises the "E490K:I538K" cleavage domain and other comprises "Q486E:I499L" cleavage domain is also referred to as a "EL/KK" ZFN pair. The engineered cleavage half-domains described herein are obligate heterodimer mutants in which aberrant cleavage is minimized or abolished when one or more pairs of nucleases containing these cleavage half-domains are used for cleavage. See, e.g., U.S. Patent Publication No. 20080131962, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication Nos. 20050064474 (Example 5) and 20070134796 (Example 38).

C. Additional Methods for Targeted Cleavage in GS

Any nuclease having a target site in a GS gene can be used in the methods disclosed herein. For example, homing endonucleases and meganucleases have very long recognition sequences, some of which are likely to be present, on a statistical basis, once in a human-sized genome. Any such nuclease having a unique target site in a GS gene can be used instead of, or in addition to, a zinc finger nuclease, for targeted cleavage in a GS gene.

Exemplary homing endonucleases include I-SceI, I-CeuI, PI-PspI, PI-Sce, I-SceIV, I-CsmI, I-PanI, I-SceI, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66. Thus, engineered homing endonucleases and/or meganucelases which are designed to specifically bind a desired target locus, such as GS, may also be used.

Delivery

The ZFNs described herein may be delivered to a target cell by any suitable means. Suitable cells include but not limited to eukaryotic and prokaryotic cells and/or cell lines. Non-limiting examples of such cells or cell lines include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces.*

Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more of the ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more ZFN encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids encoding engineered ZFPs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-March) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.) and Copernicus Therapeutics Inc., (see for example U.S. Pat. No. 6,008,336).

Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V72, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pichia* and *Schizosaccharomyces.* Progeny, variants and derivatives of these cell lines can also be used.

Applications

The disclosed methods and compositions can be used for inactivation of a GS genomic sequence. As noted above, inactivation includes partial or complete repression of GS gene expression in a cell. Inactivation of a GS gene can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript.

Thus, the methods and compositions described herein allow for the generation of GS-deficient cell lines for use in recombinant protein production, for example α1-antitrypsin and/or monoclonal antibody production. Additional genes, such as FUT8 may also be inactivated as cells in which FUT8 is inactivated produce antibodies that exhibit greater effector function, particularly in the induction of ADCC.

EXAMPLES

Example 1

Design and Construction of ZFNs

A. Glutamine Synthetase (GS) ZFNs
As the full sequence of the CHO genome is not available, the CHO GS gene was cloned and sequenced to generate the target DNA sequences for ZFN designs. The complete CHO GS sequence is shown in FIG. 13, which also designates introns and exons.

Figure 4A:
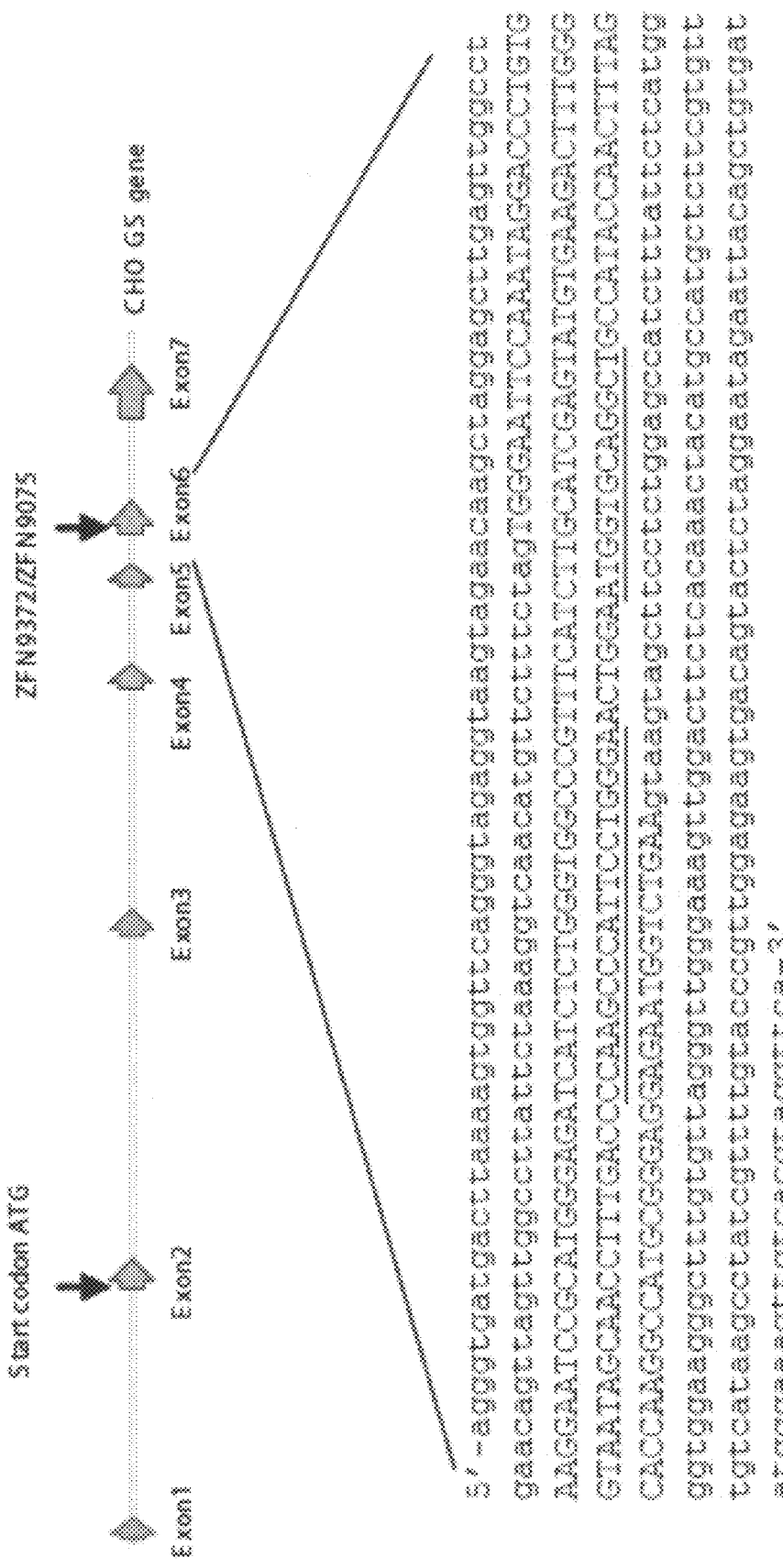
FIG. 4A is a schematic representation of the functional intron-containing glutamine synthetase gene in CHO. cells. It contains 7 exons, the start codon ATG is located in exon 2, and the target sequence of ZFN pair ZFN9372/ZFN9075, located in exon 6, is also indicated. The nucleotide sequence (SEQ ID NO: 88) of the region of interest around exon 6 is shown. Capital letters indicate exon 6 sequences, small letters indicate intron sequences. The target sequences of ZFN9372 and ZFN9075 are underlined.

ZFN target sites in exon 6 of the CHO GS gene were selected because this region encodes amino acids critical for the catalytic function of the GS protein based on available crystal structures (see, e.g., Almassy et al. (1986) *Nature* 323:304-309; Gill et al. (2002) *Biochem.* 41:9863-9872; Liaw et al. (1994) *Biochem.* 33:675-681) and, as such, ZFN-mediated mutation of this site was expected to result in loss of functional GS activity. Partial sequence for CHO GS exon 6 is shown below. Capital letters indicate exon sequence; small letters indicate intron sequence; and ZFN target sites 9372/9075 (Table 1, FIG. 1A and FIG. 4A) are underlined:

(SEQ ID NO: 30)
5'-atggcactattctgttccttttcctccctctgaagacttggcacat ggggactttggttaacaagggtgatgacttaaaagtggttcagggtagag gtaagtagaacaagctaggagcttgagttggcctgaacagttagttggcc ttattctaaaggtcaacatgttctttctagTGGGAATTCCAAATAGGACC

CTGTGAAGGAATCCGCATGGGAGATCATCTCTGGGTGGCCCGTTTCATCT

TGCATCGAGTATGTGAAGACTTTGGGGTAATAGCAACCTTTGAC<u>CCAAG</u>

<u>CCCATTCCTGGGA</u>ACTGG<u>AATGGTGCAGGCT</u>GCCATACCAACTTTAGCAC

CAAGGCCATGCGGGAGGAGAATGGTCTGAAgtaagtagcttcctctggag ccatctttattctcatggggtggaagggctttgtgttagggttgggaaag ttggacttctcacaaactacatgccatgctcttcgtgtttgtcataagcc tatcgttttgtacccgttggagaagtgacagtactctaggaatagaatta cagctgtgatatgggaaagttgtcacgtaggttcaagcatttaaaggtct ttagtaagaactaaatacacataCaagcaagtgggtgacttaattcttac tgatgggaagaggccagtgatgggggtcttcccatccaaaagataattgg tattacatgttgaggactggtctgaagcacttgagacataggtcacaagg cagacacagcctgcatcaagtatttattggtttcttatggaactcatgcc tgctcctgcccttgaaggacag-3'

Binding sites for ZFN9372 and ZFN9075 are shown in FIG. 4B, while FIG. 4C depicts the target and finger designs of these ZFNs.

In addition, ZFNs targeted to sites in exon 2 were also designed. Partial sequence for CHO exon 2 is shown below. Capital letters indicate exon sequence; small letters indicate intron sequence; and ZFN target sites 8365/8361 (Table 1, and FIG. 1A) are underlined.

(SEQ ID NO: 31)
5'-ggctggcagatctccgagttcgaggctgacctggtctgaatagcaag gaaattaaggggtgaggcgtatgtctgttaaagcaagaataaaaggcaaa ggaacactccacagtcaattattcaagtcttgatggcagtaatgtagttg tattgggtggattaagacattctaataatgaattttttttgtcttttttgtt ccctcttttcagctttctcaaaattaatggatattaaaaatccccttagc cgggcgttggtggcacacacctttaatcccagcactcgggaggcagaggc aggcagatctctgtgagttcgaggccagcctggtctccagattgagtgcc -continued

```
aggataggctccaaagctacacagaaaccgtgtctcgaaaaacaaaacaa
aaaaataaaaaaaaaaatcccttaactagcccaacctacaagggatgatc
tttgtctaactatgaactttaaacctcttgaaagcagagtgaataatgca
cttcaataatgttgacttccaaaggagagaccaccacaccgttccctgtg
cctcttacgcaattcctgcaggggaccccttcagagtagatgttaatga
aatgacttttgtctctcCAGAGCACCTTCCACCATGGCCACCTCAGCAAG
TTCCCACTTGAACAAAAACATCAAGCAAATGTACTTGTGCCTGCCCCAGG
GTGAGAAAGTCCAAGCCATGTATATCTGGGTTGATGGTACTGGAGAAGGA
CTGCGCTGCAAAACCCGCACCCTGGACTGTGAGCCCAAGTGTGTAGAAGg
tgagcatgggcaggagcaggacatgtgcctggaagtgggcaagcagcctg
agatttgaccttccttctgttttgtttgcaaagtctttcaaaagcaggtc
tcttcaggcctcagtcagtcaccgtaagctgccgagtagtctggaggca
tagaaaacaatggaggcctttatttagatggaatcttgtgtgtgctggta
cactgaagaaaatattgggtcatatttgtagggggtgggaggttggagt
attgctaacctagccaaccccaggaacctagtttgaaagacctgtaacta
gaatatgctatcaagtttatagagcagtggttctcaacctttcaaatgct
ttacacttgaatacaactcctcatgttctggtgattaccccatcccaac
cattgctaacttcttaactgaaatttcactactgctacgaatcataatgt
atctgtgttttggatggtcttaggtgaccctgtgaaagggttgtgaga
ccatcctcaaagggggttgtgacctacaggttgagaccccttttgagtgctg
tgtttattagtatttatacagtggaattctgggtgcaaagcacatgctcc
aaagtagtttctctgggactggccatttgttttcgatggggatcttttaa
aacttgcaaaggaaccaaaaaaaaaaaaatgcagaaaaaaggaggtgggg
gagtgcacgcctttaatcccagtacttgggaggcagaggcaggcggatct
ctgtgagtttgagaccagcctggtctacaagagctagttccaggacagcc
tccaaagccacagagaaaccctgtctcaaaacaaacaaacaaacaaaaaa
attaaaaaaaaaaaaaactttcaaaggagacctgttttattttagttgtg
gcctttgttttggtaggaagggcagctagtttaggatgagtttttattat
tctaagatgttgccgtttg-3'
```

ZFNs targeting the CHO GS sequence (for example as shown in Table 1), were assembled into mammalian expression vectors as described in U.S. patent application Ser. No. 12/218,035 and tested by transient transfection into CHO cells.

B. DHFR ZFNs

ZFNs targeted to DHFR were designed and produced as described in U.S. Patent Publication No 2008/0015164. For experiments described herein, DHFR ZFN pairs designated 9461/7844 and 9476/9477 (individual ZFNs shown in Table 2) were used.

TABLE 2

Exemplary zinc finger nucleases targeted to DHFR

| ZFN name Target sequence | F1 | F2 | F3 | F4 |
|---|---|---|---|---|
| ZFN 7844 ccAATGCTCAGGTAct (SEQ ID NO: 32) | QSGALAR (SEQ ID NO: 14) | RSDNLRE (SEQ ID NO: 3) | QSSDLSR (SEQ ID NO: 2) | TSSNRKT (SEQ ID NO: 25) |
| ZFN 9461 agGGAAGGTCTCCGtt (SEQ ID NO: 33) | RSDTLSE (SEQ ID NO: 34) | NNRDRTK (SEQ ID NO: 35) | RSDHLSA (SEQ ID NO: 36) | QSGHLSR (SEQ ID NO: 37) |
| ZFN 9476 caTGGGTAGCCGCTga (SEQ ID NO: 38) | QSSDLSR (SEQ ID NO: 2) | DRSDLSR (SEQ ID NO: 39) | QSGALAR (SEQ ID NO: 14) | RSDHLTT (SEQ ID NO: 40) |
| ZFN 9477 agTCCGGGGGGTGGtg (SEQ ID NO: 41) | RSDHLST (SEQ ID NO: 7) | RSAHLSR (SEQ ID NO: 17) | RSDHLSR (SEQ ID NO: 42) | DSSDRKK (SEQ ID NO: 43) |

C. FUT8 ZFNs

ZFNs targeted to FUT8 were designed and produced as described in U.S. Ser. No. 12/218,035. For experiments described herein, FUT8 ZFNs designated 12176 and 12172 and shown in Table 3 were used.

TABLE 3

Exemplary zinc finger nucleases targeted to FUT8

| ZFN name Target sequence | F1 | F2 | F3 | F4 | F5 | F6 |
|---|---|---|---|---|---|---|
| ZFN 12172 AAGGAGGCAAAGA CAAAG (SEQ ID NO: 44) | RSDNLSV (SEQ ID NO: 45) | QNATRIN (SEQ ID NO: 46) | RSDHLSQ (SEQ ID NO: 9) | QSATRTK (SEQ ID NO: 47) | RSDNLSR (SEQ ID NO: 48) | RNDNRKT (SEQ ID NO: 49) |
| ZFN 12176 AAGAAGGGTCATC AG (SEQ ID NO: 50) | RSDNLRE (SEQ ID NO: 3) | NNTQLIE (SEQ ID NO: 51) | TSSILSR (SEQ ID NO: 52) | RSDNLSA (SEQ ID NO: 53) | RKDTRIT (SEQ ID NO: 54) | N/A |
| ZFN 12170 taAAGGAGGCAAAG ACAAAGt (SEQ ID NO: 56) | RSDNLSV (SEQ ID NO: 45) | QNATRIN (SEQ ID NO: 46) | RSDNLST (SEQ ID NO: 57) | QSATRTK (SEQ ID NO: 47) | RSDNLSR (SEQ ID NO: 48) | RNDNRKT (SEQ ID NO: 49) |

Plasmids comprising sequences encoding the above ZFNs were constructed essentially as described in Urnov et al. (2005) *Nature* 435(7042):646-651 via fusion to wild-type FokI cleavage domains or obligate heterodimer FokI cleavage domains described in U.S. Patent Publication No. 2008/0131962 and Miller et al. (2007) *Nature Biotech.* 25:778-785.

Example 2

GS-ZFN Modification of Endogenous GS

To determine whether GS-targeted ZFNs modified the endogenous GS locus as expected, CEL-1 mismatch assays were performed essentially as per the manufacturer's instructions (Trangenomic SURVEYOR™). Briefly, the appropriate ZFN plasmid pairs were transfected into CHO K-I cells growing adherently in serum-containing medium or CHO-S cells growing in suspension in serum-free chemically defined medium.

CHO K-I cells were obtained from the American Type Culture Collection and grown as recommended in F-12 medium (Invitrogen) supplemented with 10% qualified fetal calf serum (FCS, Hyclone). CHO-S cells were purchased from Invitrogen (Carlsbad, Calif.) and were grown and maintained as suspension cultures in chemically-defined protein-free and animal component-free CD-CHO medium supplemented with 8 mM L-glutamine and HT supplement as necessary (100 µM sodium hypoxanthine and 16 µM thymidine) (all from Invitrogen, Carlsbad, Calif.) in a humidity-controlled shaker incubator (ATR, inc., Laurel, Md.) at 125 rpm with 5% $CO_2$ at 37° C.

Adherent cells were disassociated from plasticware using TrypLE Select™ protease (Invitrogen). For transfection, one million CHO K-I cells were mixed with 1 µg each zinc finger nuclease and 100 µL Amaxa Solution T. Cells were transfected in an Amaxa Nucleofector II™ using program U-23 and recovered into 1.4 mL warm F-12 medium+10% FCS.

Genomic DNA was extracted from the ZFN-treated cells using the Qiagen DNeasy™ kit (Qiagen, Inc.), the target locus amplified by PCR using the appropriate primers for the region of the GS locus targeted by the ZFNs, the PCR products were subjected to a melting/annealing step resulting in the formation of distorted duplex DNA through random re-annealing of mutant and wild-type DNA. CEL-I enzyme (Surveyor™ mutation detection kit, Transgenomic, Inc.) was then added to specifically cleave the DNA duplexes at the sites of mismatches. The CEL-I cleaved samples were resolved on a 10% TBE polyacrylamide gel, stained with ethidium bromide, and the DNA bands were quantified using densitometry. The frequency of NHEJ was calculated as described essentially in Miller et al. (2007), supra.

As shown in FIGS. 1A and 1B, GS ZFNs modified the endogenous GS locus. In particular, the ZFN pair including ZFN 9372 and ZFN 9075 resulted in modification of 26% (with wild-type cleavage domains) and 24% (with engineered obligate heterodimer forming cleavage domains) of chromosomes in CHO-KI cells and 25% of chromosomes in CHO-S cells (FIG. 1B). Similarly, ZFN pair including ZFN 8361 and 8365 (targeted to exon 2) resulted in modification of 7% of chromosomes.

Figure 5:
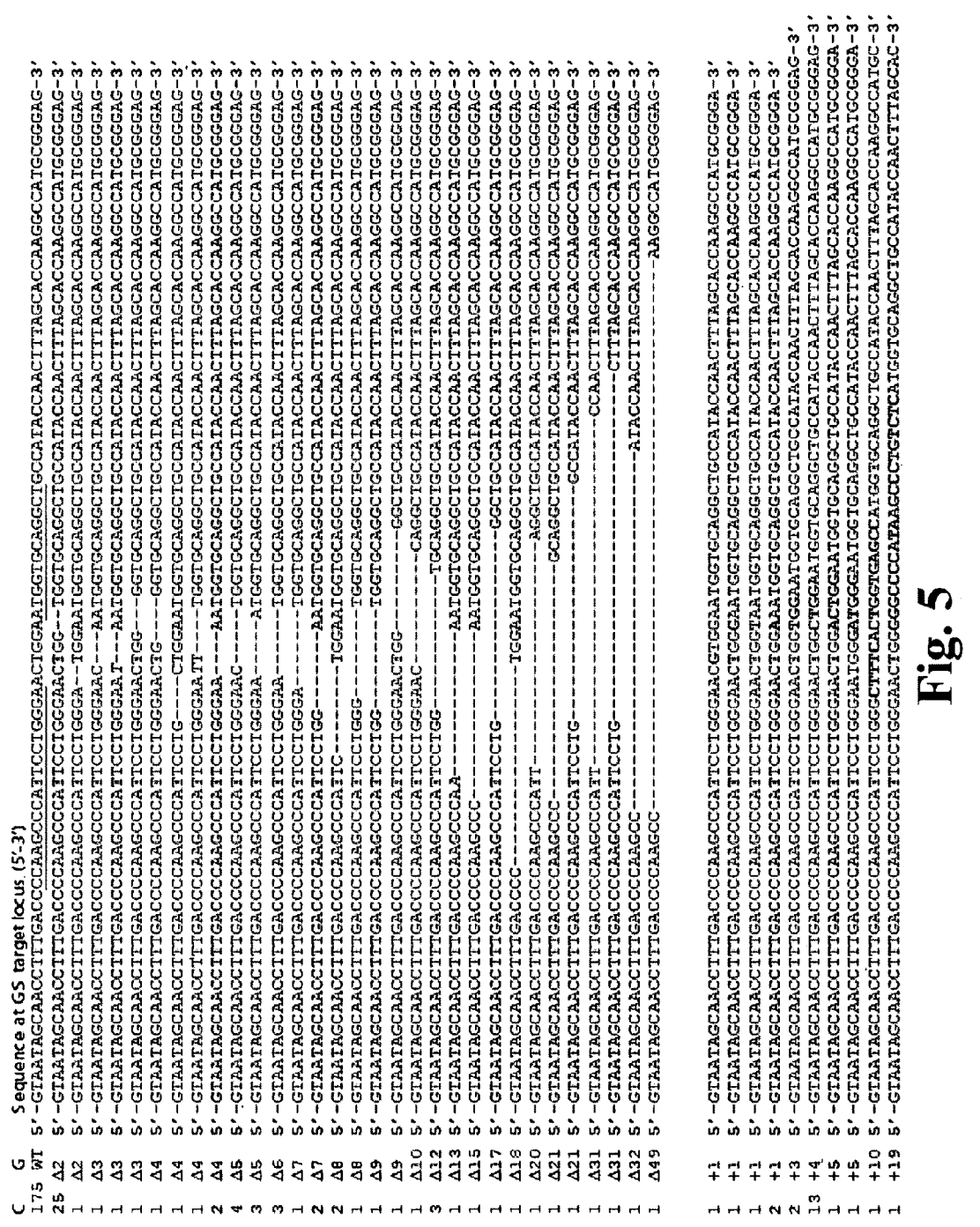

In agreement with the results of the Surveyor™ Nuclease Assay (FIG. 1A), direct sequencing confirmed 34% (91/266) of the alleles harbored mutations at the ZFN target site typical of NHEJ-mediated DNA repair (see, e.g., Weterings et al. (2004) *DNA repair (Amst)* 3:1425-1435). Importantly, 81% of the sequenced mutations resulted in a reading frame shift (FIG. 5).

Example 3

Generation of GS-Negative Cell Lines

To generate CHO cell lines lacking GS, single-cell derived lines were isolated by limiting dilution from both the CHO-K1 and CHO-S transfected pools described in Example 2. Sequencing of the ZFN target region revealed that 17 of 54 CHO-S derived cell lines (31%) had at least one disrupted GS gene, 8 of 54 (15%) were homozygous for a mutant allele, 2 were compound heterozygous, and the remaining 7 were heterozygous (with one wild-type allele). For CHO-K1-derived cell lines, sequencing analysis identified 18 of 50 (36%) had at least one disrupted GS allele, with 5 (10%) homozygous for a given mutation. See, also, FIG. 1C showing the genotypes of the homozygous mutant lines.

All homozygous mutant lines harbor GS mutations that result in a shift in the open reading frame or an in-frame deletion of critical amino acids (e.g. lines B4, KA2, and KA4), and were therefore expected to produce no active GS enzyme. As predicted, none of the homozygous mutant cell lines grew in the absence of exogenous L-glutamine, in contrast to wild-type CHO cells (FIG. 1C).

Figure 6:
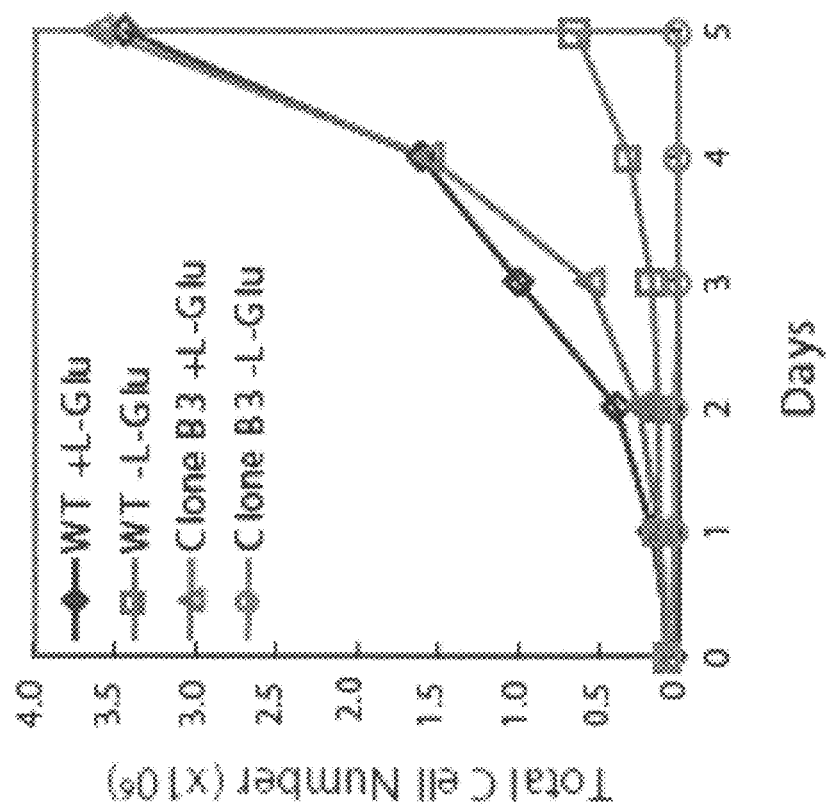
FIG. 6 is a graph depicting L-glutamine-dependent growth of a homozygous GS−/− cell line (Clone B3). In the presence of L-glutamine, CHO-S GS−/− clone B3 (triangle) grows as well as wild-type CHO-S (diamond). In the absence of exogenous L-glutamine, the Clone B3 (circle) stopped growing and all cells died within 4 days, whereas the wild-type CHO cells (square) continued to grow at a reduced rate.

Western blot analysis using an anti-GS monoclonal antibody (BD Biosciences) confirmed that all cell lines with frame shifts or large deletions expressed no detectable GS protein (for example, clone B3, FIG. 1D). Lines harboring small in-frame deletions (B4 and KA2) did express GS proteins that were detectable by Western blot but, consistent with the elimination of amino acids critical for GS catalytic activity, did not support the growth of the cells in the absence of L-glutamine (FIG. 1C). Growth of cell line B3 was also shown to be dependent on glutamine supplementation (see FIG. 6).

To further validate their $GS^{-/-}$ phenotype, three of the CHO-K1-derived clones were adapted for growth in suspension in a chemically-defined serum-free medium over a 3 month period. Growth and viability of the cells was then monitored intensively for a further 4 weeks (FIG. 1E).

The ZFN-generated $GS^{-/-}$ lines grew normally in serum-free suspension. cultures in the presence of L-glutamine (24-27 hour doubling time similar to the industry standard CHOK1 SV grown under similar conditions). Subsequent removal of L-glutamine resulted in immediate cessation of cell growth and a rapid loss of viability (see arrows in FIG. 1E). Transient transfection of a human IgG antibody expression construct confirmed all three $GS^{-/-}$ lines supported comparable transgene expression levels to those obtained with the CHOK1SV line.

Taken together, these data confirm the successful generation of genetically and phenotypically validated GS knockout CHO cell lines.

Example 4

Generation of GS-DHFR Double Knockout Cell Lines

To create a double-knockout cell line, ZFNs targeted to the DHFR gene were used on the background of the CHO-S $GS^{-/-}$ cell line B3. ZFN-mediated knockout of DHFR using the strategy described for GS above is described in U.S. Patent Publication No. 2008/0015164:

In this Example, two pairs of ZFNs targeting two distinct regions of the DHFR gene were delivered simultaneously with the goal of eliminating the intervening genomic fragment through the repair of the cleaved chromosomal ends via NHEJ. Deletion of a ZFN-specified intergenic sequence was expected to result in a larger and better defined mutation that eliminates the potential for a smaller in-frame mutation to recover protein expression e.g. FIG. 1D (Left Panel labeled "B4").

Figure 7B:
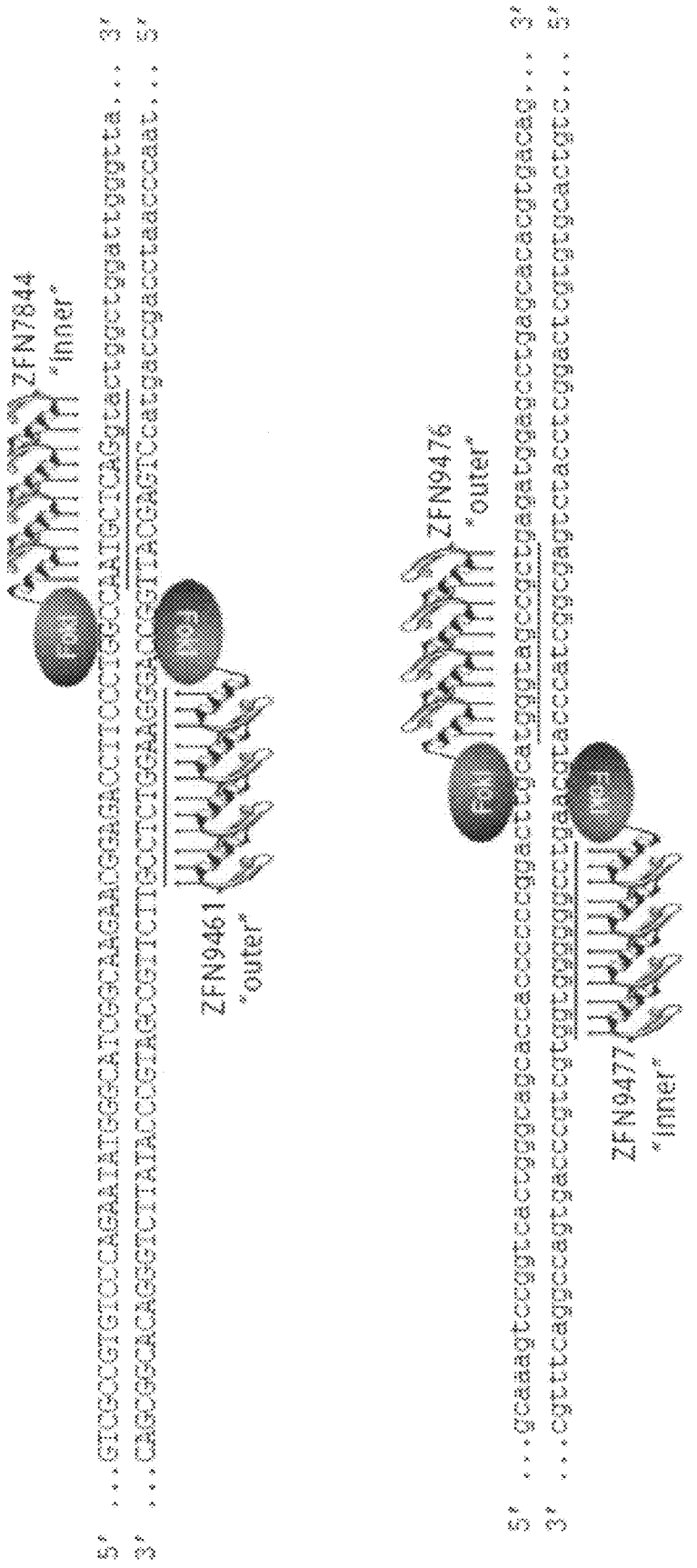
FIG. 7B (SEQ ID NOS: 134-137, respectively) is a schematic representation of the ZFNs targeting DHFR when the ZFNs are bound to their double-stranded target sequences (underlined). The two ZFNs labeled "inner" target sequences are internal to the region to be deleted, while the two ZFNs labeled "outer" target sequences are outside of the expected deletion junction.

In addition to the previously described ZFN pair 9461/7844 that target exon 1 of the CHO DHFR gene (U.S. Patent Publication No. 2008/0015164), a second ZFN pair was generated which targets a site ~240 bp away in the intron immediately following exon 1 (FIG. 2A and FIG. 7A).

Transient transfection was performed as described in Example 3 and transfection with either the ZFN9461/ZFN7844 pair targeting exon 1, or the ZFN9476/ZFN9477 (See FIGS. 7B and 7C) pair targeting the intronic site alone resulted in allelic mutation frequencies at the endogenous DHFR locus of 15% and 18%, respectively in the $GS^{-/-}$ cell line B3 (FIG. 2B). Co-transfection of both ZFN pairs into the $GS^{-/-}$ cell line B3 resulted in the appearance of a shorter PCR amplification product consistent with the expected ~240 bp deletion of the sequence between the ZFN binding sites (FIG. 2C). The frequency of this deletion event was estimated at ~8% of all alleles and was observed only when both pairs of ZFNs were introduced into the cells (FIG. 2C).

Figure 8:
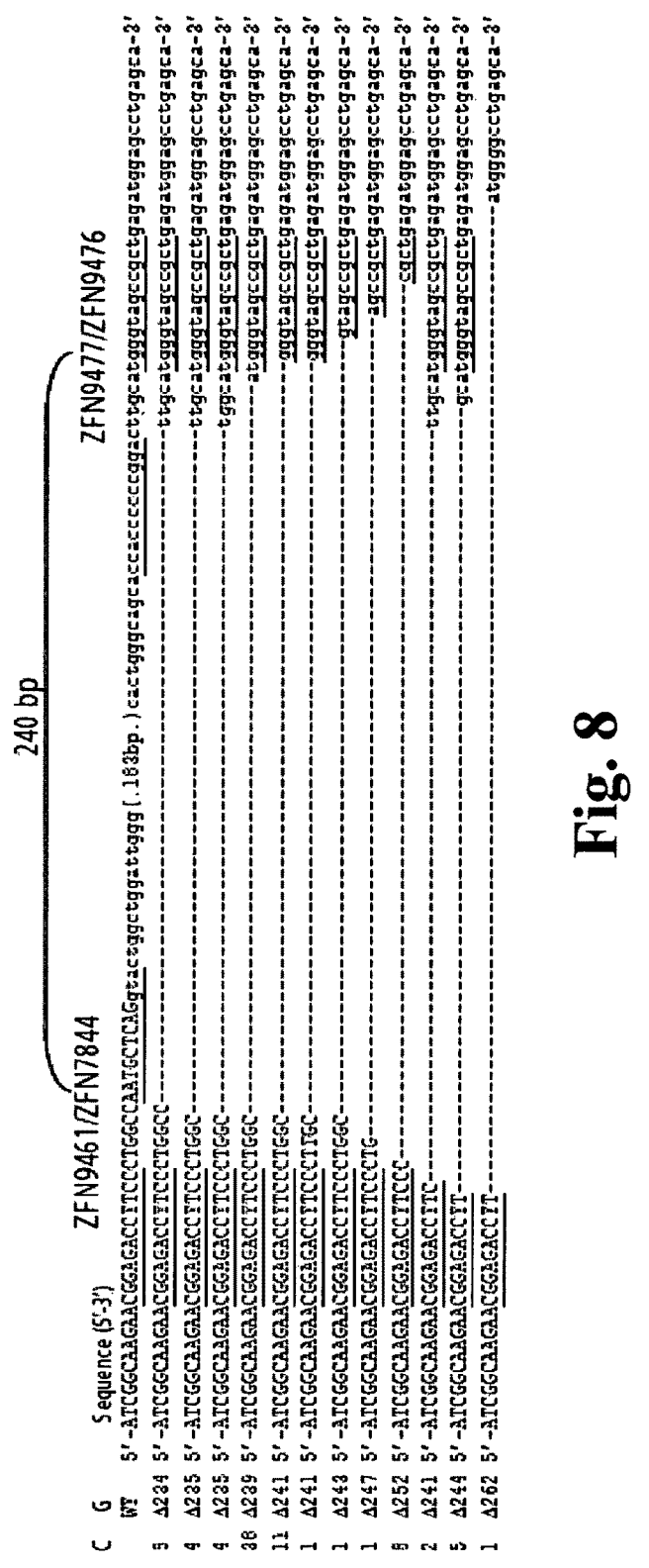

Cloning and sequencing of the presumptive deletion PCR fragment revealed the expected excision of the sequence between the ZFN target sites (FIG. 8). The observed minor variations in the sequence at the junction of the rejoined chromosomal ends are consistent with the expected small insertions and deletions characteristic of the NHEJ repair process.

Figures 2D, 2E:
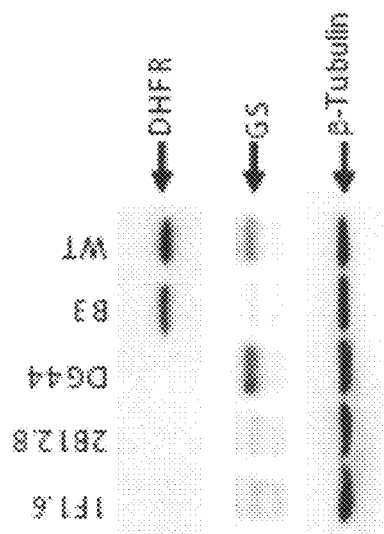
FIG. 2D (SEQ ID NOS: 74-81, respectively) depicts results of DHFR genotyping analysis of single-cell lines. For homozygous clones, the common sequence for both alleles is shown. For compound heterozygous clones the sequence of each unique allele is shown.
FIG. 2E depicts Western blot analysis with the indicated antibodies (DHFR, GS and β-tubulin) of whole cell lysates from the cell lines indicated above each lane. Cell lines 1F1.6 and 2B12.8 (DHFR/GS knockout) were analyzed while the parental GS−/− cell line B3, wild-type CHO cells (WT), and the DHFR-deficient CHO cell line DG44 (see Urlab et al. (1983) Cell 33:405-412) served as controls.

Single-cell derived lines were isolated from the ZFN-treated pool in FIG. 2C Lane 7 by limiting dilution. PCR-amplification and sequencing revealed 9% (18 of 200) of the cell lines possessed the expected ~240-bp deletion. Four of these cell lines (2% of all lines screened, 22% of all lines containing the deletion) were found to harbor a biallelic mutation in the DHFR gene (FIG. 2D). Cell line 2B12.8 is homozygous for a 244-bp deletion of the intervening region between the exon1 and intron 1 ZFN cleavage sites. The remainder of the lines had just one allele with the 240-bp deletion while the other presented classical smaller NHEJ driven mutations at the exonic and/or intronic ZFN target sites. For example, cell line 1F1.6 contained a ~240-bp deletion in one allele (consistent with a dual ZFN cleavage and deletion event), but the other allele contained a 4-bp deletion in exon 1 resulting in a frame shift.

Figure 2F:
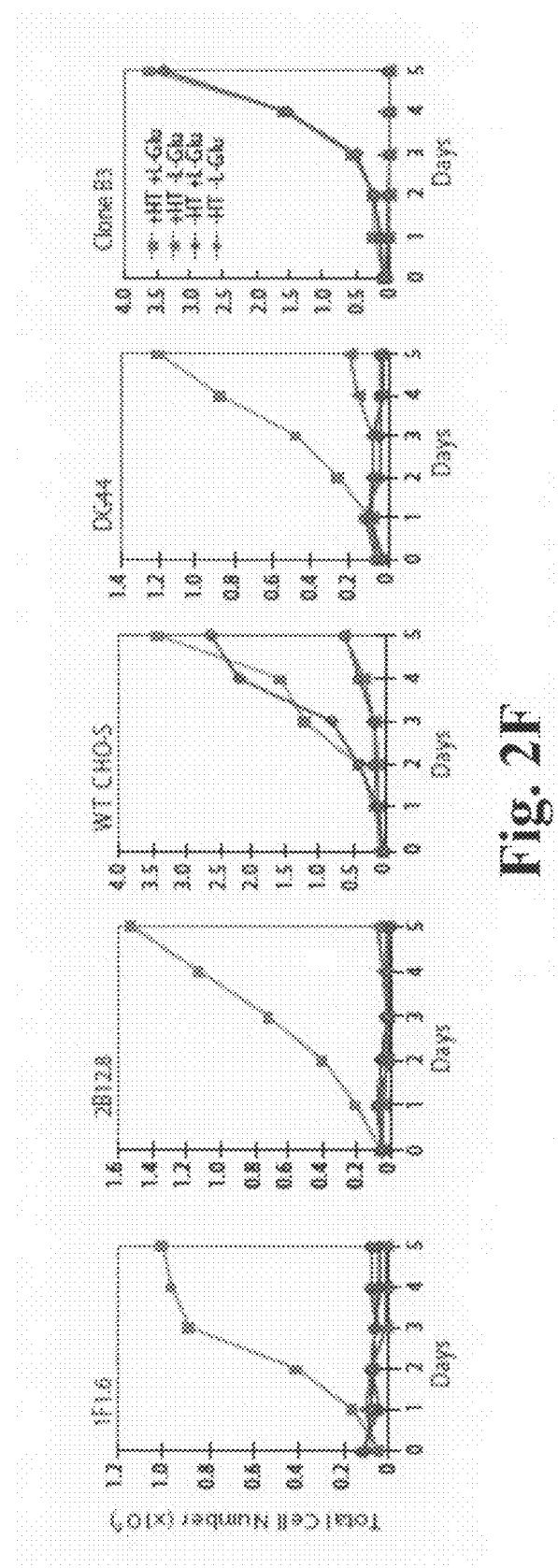
FIG. 2F depicts growth of the 1F1.6 and 2B12.8 cell lines and the dependence of these lines on exogenously provided hypoxanthine, thymidine and glutamine.

Cell lines 1F1.6 and 2B12.8 had genotypes consistent with complete gene knockout and thus were selected for further characterization. Western blot analysis revealed no full-length DHFR or GS protein in either of these single-cell derived lines (FIG. 2E). Furthermore, neither line was stainable with fluorescein-labeled methotrexate which binds to the active site of the DHFR protein, in contrast to the parental $GS^{-/-}$ line B3 or wild-type CHO cells. Most importantly, growth of the 1F1.6 and 2B12.8 cell lines was dependent upon the addition of exogenous hypoxanthine and thymidine (HT) and L-glutamine to the culture medium. In contrast, the parental $GS^{-/-}$ line B3 required L-glutamine but not HT, while the DHFR-negative CHO cell line DG44 ($GS^{WT}$) required only HT but not L-glutamine and the wild-type CHO-S required neither supplement for growth (FIG. 2F).

The dependence on exogenous HT and L-glutamine confirms the functional loss of both GS and DHFR activity in cell lines 1F1.6 and 2B12.8.

Thus, taken together these data demonstrate the successful generation of genetically and phenotypically validated $GS^{-/-}/DHFR^{-/-}$ double knockout CHO cell lines.

Example 5

Generation of GS-DHFR-FUT8 Triple Knockout Cell Lines

A triple knockout of GS, DHFR and FUT8 was also generated using the $GS^{-/-}$ $DHFR^{-/-}$ CHO cell line IF1.6. As described in U.S. Ser. No. 12/218,035, aberrant glycosylation resulting from the use of non-human cells e.g. CHO in the expression of protein therapeutics can alter the potency, half-life and even the immunogenicity of the protein product. Thus methods for humanizing the glycosylation of proteins in non-human expression systems are highly desirable. The CHO FUT8 gene is such a target encoding an α1,6-fucosyltransferase that catalyzes the transfer of fucose from GDP-fucose to the core GlcNAc of N-linked oligosaccharides. Point mutations of amino acid residues in the highly conserved Fut motif II encoded in exon 10 result in the inactivation of the FUT8 enzyme.

Figures 9A, 9B:
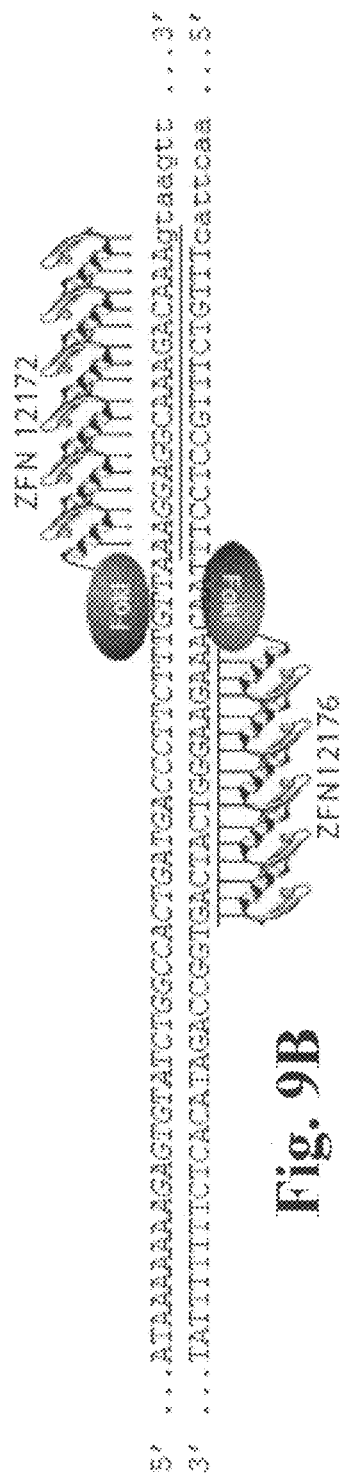
FIG. 9A (SEQ ID NO: 151) depicts a schematic of the ZFN binding sites within exon 10 of the FUT8 gene as well as the nucleotide sequence of the target region within exon 10. Capital letters indicate exon 10 sequences, small letters indicate intronic sequences. The target sequences of ZFN12176 and ZFN12172 are underlined. The nucleotides comprising the fucosyltransferase motif II are shown in italics.
FIG. 9B is a schematic representation of ZFN12176 (SEQ ID NO: 153) and ZFN12172 (SEQ ID NO: 152) binding to their double-stranded target sequence (underlined).

Thus, we cloned and sequenced the region spanning FUT8 exon 10 and flanking introns from CHO-K1 genome, and designed ZFNs to target exon 10 (U.S. patent application Ser. No. 12/218,035; FIG. 3A and FIG. 9). Transient delivery of ZFN12172/ZFN12176 into cell line 1F1.6 resulted in modification of 7.5% of the FUT8 alleles (FIG. 3B), and single-cell derived lines were obtained by limiting dilution from this pool.

*C. griseus* FUT8 was not detectable using commercially available antibodies, so we further assayed α1,6-fucosyltransferase activity using a FACS-based fluorescent Lens culinaris agglutin (F-LCA) binding assay, as described in Yamane-Ohnuki et al. (2004) *Biotechnol Bioeng* 87:614-622. LCA selectively binds to cells that present core fucosylated oligosaccharides on their cell surface. Cells lacking core fucosylation due to a complete loss of FUT8 activity do not bind to LCA. Screening of the ZFN-generated cell lines for their ability to bind F-LCA showed no F-LCA binding in 2% of the line (4 of 200) indicating a complete absence of FUT8 enzymatic activity (FIG. 3C).

Sequencing of PCR amplicons of genomic DNA confirmed that both clones possess biallelic compound heterozygous mutations at the FUT8 target locus (FIG. 3D), which encode a shift in reading frame in this functionally critical region. Thus the genotype of both cell lines is consistent with the lack of F-LCA binding observed (FIG. 3C) and demonstrates the ZFN-driven genetic and functional knockout of FUT8 in cell lines 35F2 and 14C1. Both of the FUT8$^{-/-}$ clones also stably maintained their GS$^{-/-}$ and DHFR$^{-/-}$ genotypes and phenotypes, throughout the multiple rounds of ZFN transfection and single-cell cloning. Indeed, the generation of a triple knockout cell line was well-tolerated as measured by growth rate studies in serum-containing medium supplemented with HT and L-glutamine which gave mean population doubling times of 21.8 and 21.6 hours for clones 35F2 and 14C1, respectively. Taken together these data demonstrate the successful generation of single, double and triple gene knockouts in CHO cells using engineered ZFNs.

Example 6

Generation of GR-CCR5-PPP1R12C Triple Knockout Cell Lines

A triple knockout cell line was also generated by concurrent administration of inactivating ZFNs. In particular, K562 cell lines in which CCR5, glucocorticoid receptor (GR) and PPP1R12C (also known as the adeno-associated virus integration site or "AAVS1") were inactivated were also generated by simultaneous application of ZFNs targeted to these loci.

ZFNs targeted to CCR5, GR and AAVS1 were generated as described in U.S. Patent Publication Nos. 20080159996 (CCR5); 20080188000 (GR) and U.S. application Ser. No. 12/150,103 (PPP1R12C/AAVS1). Schematics showing the ZFN binding sites in portions of these genes are shown in FIG. 10A. The CCR5 gene contains 3 exons, the coding sequence (CDS) is located within exon 3, and the CCR5 ZFN target sequence is located in the CDS as indicated. The GR gene contains 9 exons, and the GR ZFN target sequence is located in Exon3. The AAVS1 ZFN target sequence is located in the middle of the AAVS1 region.

Plasmids encoding pairs of ZFNs linked to either the wild-type, ZFN-Fok I(wt) or an obligate heterodimer EL/KK variant, ZFN-Fok I(EL/KK) of the catalytic domain of Fok I were transiently co-transfected into K562 cells, and the modification frequency at CCR5 (left), GR (middle), AAVS1 (right) loci was determined by the Surveyor™ Nuclease Assay 10 days after transfection, respectively. As shown in FIG. 10B, the target genes were subject to NHEJ following ZFN treatment.

Single-cell derived cell lines of these triple-knockout cells were also evaluated by PCR and sequencing of genomic DNA described above. In particular, the lane 8 samples in FIG. 10B, treated with CCR5 ZFN-Fok I(EL/KK)+GR ZFN-Fok I(EL/KK)+AAVS1 ZFN-Fok I(EL/KK) were examined. The PCR primers were designed to specifically amplify unmodified wild-type (wt) sequences but not sequences with deletions.

Results are shown below in the following Table 4. All clones containing wt sequences (wt or heterozygous) had visible PCR bands at predicted sizes, whereas knock-out (KO) clones had no visible PCR bands. Among 144 single cell clones screened by CCR5 PCR, 5 clones contain CCR5 KO. Nine clones were identified as GR KO by GR PCR. Two of the clones contain both CCR5 KO and GR KO. All 12 clones, which are KO clones based on either CCR5 PCR or GR PCR, were screened by AAVS1 PCR. Among the 144 clones screened, one CCR5 single KO clone was identified, seven GR single KO clones were identified, whereas no attempt was tried to identify AAVS1 single KO clones. One CCR5/GR dual KO clone was identified. Two CCR5/AAVS1 dual KO clones were identified. No GR/AAVS1 dual KO clone was identified among the 144 clones, though it is very likely that a GR/AAVS1 dual KO clone might have been identified if more clones were screened. One CCR5/GR/AAVS1 triple KO clone (B17) was identified.

TABLE 4

Evaluation of single cell clones of putative triple knockout cells

|  | CCR5 | GR | AAVS1 |
| --- | --- | --- | --- |
| Total Clones screened | 144 | 144 | 12* |
| Total KO clones | 5 | 9 | 3 |
| Single KO clone | 1 | 7 | N/A |
| CCR5/GR dual KO clone | 1 | 1 | N/A |
| CCR5/AAVS1 dual KO clone | 2 | N/A | 2 |
| GR/AAVS1 dual KO clone | N/A | 0 | 0 |
| CCR5/GR/AAVS1 triple KO clone | 1 | 1 | 1 |

*12 clones that were identified as CCR5 or GR KO clones

Exemplary sequencing data of cells from triple knockout clone B17 is shown in FIG. 10C. The ZFN target sequences are underlined. '–' indicate deletions, bold letters indicate insertions.

Example 7

GS-Targeted ZFNs are Active in Multiple Species and Cell Types

GS-specific ZFNs as described herein (designed to human CHO cell GS sequence) were also evaluated in mouse cells. As shown in FIGS. 11A and 11B, ZFN target sites in GS were well conserved across species.

ZFN pairs 8361/8365 (targeted to exon 2) and 9075/9372 (targeted to exon 6) were evaluated for their ability to cleave GS in human K562 and mouse Neuro2a cells as described in Example 2 above.

As shown in FIG. 12, ZFNs designed to CHO GS sequences were functional in other human cell types and in other species.

Figure 14B:
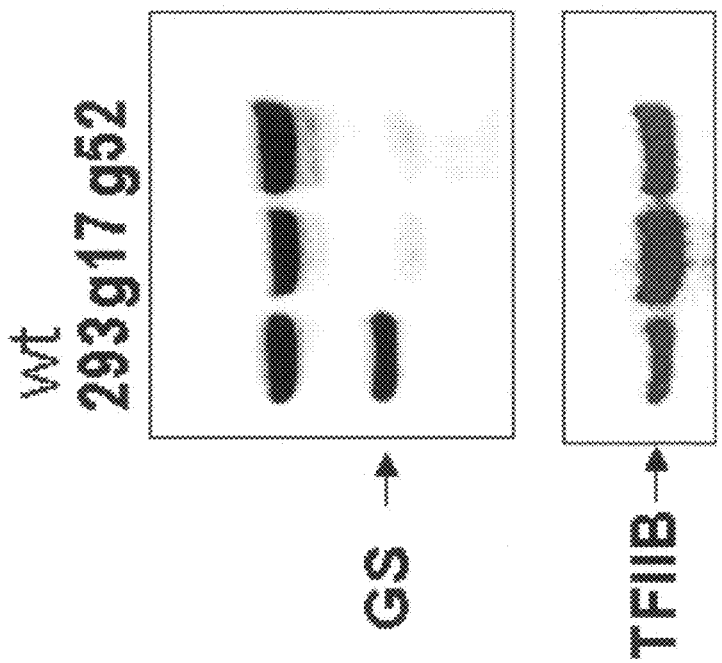
FIG. 14B shows that 2 clones, g17 and g52, derived from a pool of cells treated with the GS-specific ZFNs, do not express GS as assayed by Western blot.
Figure 14A:
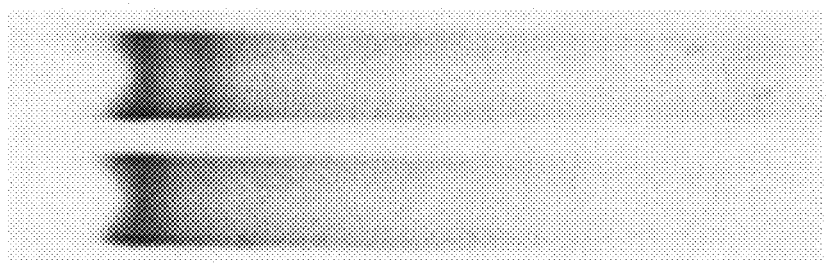
FIG. 14A depicts the percent of NHEJ activity in cells treated with GS-specific ZFNs (labeled GS) in comparison with cells transfected with a GFP donor molecule (labeled GFP).

GS-specific ZFNs (ZFN 9075 and ZFN 9372) were also tested in human embryonic kidney HEK293 cells as describe in Example 2. As shown in FIG. 14A, the CEL-I enzyme (Surveyor™ mutation detection kit, Transgenomic, Inc.) indicated an NHEJ occurance rate of 21%.

Figure 14C:
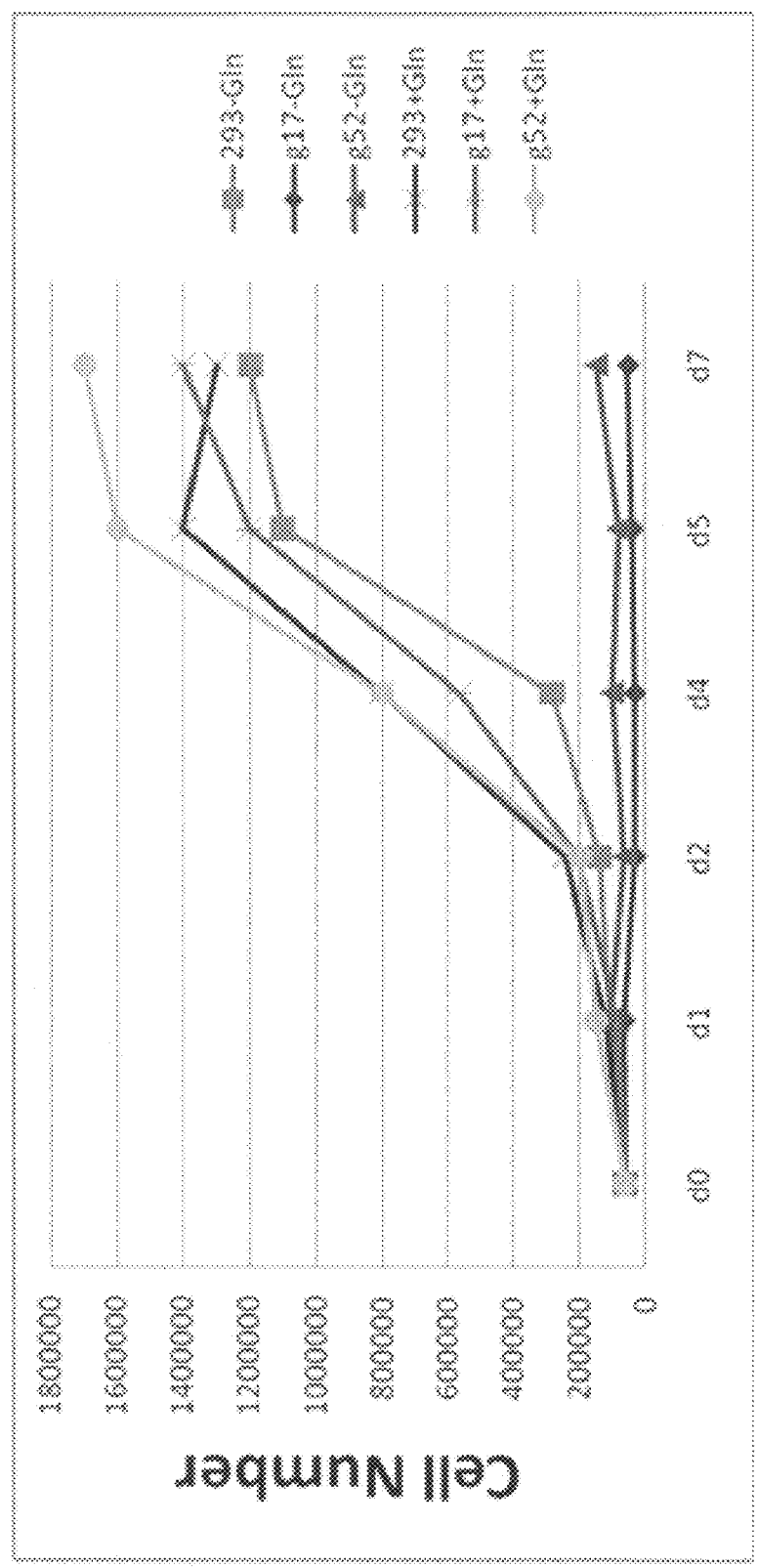
FIG. 14C is a graph showing growth over 7 days of the GS knock out clones and demonstrates the requirement for glutamine supplementation for growth.

GS knockout cell lines were made in a HEK293 cell background using the same approach as in CHO cells using the same GS ZFNs (see Example 3). Two knockout clones, clone g17 and g52, were further characterized. Clone g52 is homozygous for an 11 bp-deletion at the GS locus. Clone 17 has a 169 bp-deletion at one GS allele, and a 4 bp-insertion at the other allele. As shown in FIG. 14B, neither clone expresses GS protein as determined by western blotting. Importantly, both clones required exogenously supplemented L-glutamine for growth (see FIG. 14C).

Thus, ZFNs can be employed to rapidly knock out multiple genes in a single mammalian cell line by sequential or simultaneous inactivation of the target genes. The results presented here are not dependent on the cell line or the choice of ZFNs. The frequency of ZFN-driven biallelic knockout events at each individual gene (>1%), combined with the lack of dependence on selection markers results in the ability to rapidly "stack" such genetic lesions and generate complex multi-gene knockout cell lines previously considered impractical. The high efficiency of gene knock out following only transient ZFN expression and the ability to stack multiple traits in eukaryotic cells makes it feasible to perform custom genetic engineering of essentially any cell type.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger DNA-binding domain comprising four, five or six zinc finger recognition regions designated F1 to F4, F1-F5 or F1 to F-6 as shown in a single row of Table 1.

2. A fusion protein comprising a zinc finger DNA-binding domain according to claim 1 and at least one cleavage domain or at least one cleavage half-domain.

3. The fusion protein of claim 2, wherein the cleavage half-domain is a wild-type FokI cleavage half-domain.

4. The fusion protein of claim 2, wherein the cleavage half-domain is an engineered FokI cleavage half-domain.

5. A polynucleotide encoding the zinc finger DNA-binding domain according to claim 1.

6. An isolated cell comprising a protein according to claim 1.

7. A cell line in which glutamine synthetase (GS) is partially or fully inactivated by a fusion protein according to claim 2.

8. A method of inactivating an endogenous cellular GS gene in a cell, the method comprising:
   introducing, into a cell, a first nucleic acid encoding a first polypeptide, wherein the first polypeptide comprises a fusion protein according to claim 2:
   such that the polypeptide is expressed in the cell, whereby the polypeptide binds to its target site and cleaves the GS gene.

9. The method of claim 8, further comprising introducing a nucleic acid encoding a second polypeptide, wherein the second polypeptide comprises:

(i) a zinc finger DNA-binding domain that is engineered to bind to a second target site in the GS gene; and (ii) a cleavage domain; such that the second polypeptide is expressed in the cell, whereby the first and second polypeptides bind to their respective target sites and cleave the GS gene.

10. The method of claim 9, wherein the first and second polypeptides are encoded by the same nucleic acid.

11. The method of claim 10, wherein the first and second polypeptides are encoded by different nucleic acids.

12. The method of claim 8, further comprising inactivating a DHFR gene in the cell.

13. The method of claim 10, further comprising inactivating a FUT8 gene in the cell.

14. A method of producing a recombinant protein of interest in a host cell, the method comprising the steps of:
   (a) providing a host cell comprising an endogenous GS gene;
   (b) inactivating the endogenous GS gene of the host cell by the method of claim 8; and
   (c) introducing an expression vector comprising a transgene, the transgene comprising a sequence encoding a protein of interest into the host cell, thereby producing the recombinant protein.

15. The method of claim 14, wherein the protein of interest comprises α1-antitrypsin.

16. The method of claim 14, wherein the protein of interest is a monoclonal antibody.

17. A cell line in which a GS gene is partially or fully inactivated, wherein the cell line is produced by (a) inactivating the GS gene in a cell according to the method of claim 8; and
(b) culturing the cell under conditions suitable for generating a cell line in which the GS gene is partially or fully inactivated.

18. The cell line of claim 15, wherein the cell is a mammalian cell selected from the group consisting of a COS cell, a CHO cell, a VERO cell, a MDCK cell, a WI38 cell, a V79 cell, a B14AF28-G3 cell, a BHK cell, a HaK cell, a NS0 cell, a SP2/0-Ag14 cell, a HeLa cell, an HEK293 cell, and a perC6 cell.

* * * * *

(12) INTER PARTES REEXAMINATION CERTIFICATE (891st)
United States Patent
Liu et al.

(10) Number: US 8,153,399 C1
(45) Certificate Issued: Jun. 12, 2014

(54) METHODS AND COMPOSITIONS FOR INACTIVATING GLUTAMINE SYNTHETASE GENE EXPRESSION

(75) Inventors: Pei-Qi Liu, Richmond, CA (US); Jeffrey C. Miller, San Leandro, CA (US)

(73) Assignee: Sangamo Biosciences, Inc., Richmond, CA (US)

Reexamination Request:
No. 95/002,065, Aug. 3, 2012

Reexamination Certificate for:
Patent No.: 8,153,399
Issued: Apr. 10, 2012
Appl. No.: 12/589,884
Filed: Oct. 29, 2009

Related U.S. Application Data

(60) Provisional application No. 61/197,600, filed on Oct. 29, 2008.

(51) Int. Cl.
*C12P 21/06* (2006.01)
*C12N 1/20* (2006.01)
*C12Q 1/68* (2006.01)
*C12Q 1/48* (2006.01)
*C12N 9/22* (2006.01)
*C12N 9/00* (2006.01)

(52) U.S. Cl.
CPC .. *C12N 9/22* (2013.01); *C12N 9/93* (2013.01); *C12Y 603/01002* (2013.01); *C12N 2510/00* (2013.01)
USPC ........... 435/69.1; 435/252.3; 435/6.1; 435/15

(58) Field of Classification Search
None
See application file for complete search history.

(56) References Cited

To view the complete listing of prior art documents cited during the proceeding for Reexamination Control Number 95/002,065, please refer to the USPTO's public Patent Application Information Retrieval (PAIR) system under the Display References tab.

*Primary Examiner* — Shri Ponnaluri

(57) ABSTRACT

Disclosed herein are methods and compositions for inactivating a glutamine synthetase (GS) gene, using fusion proteins comprising a zinc finger protein and a cleavage domain or cleavage half-domain. Polynucleotides encoding said fusion proteins are also provided, as are cells comprising said polynucleotides and fusion proteins.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 18 are determined to be patentable as amended.

Claims 2-17, dependent on an amended claim, are determined to be patentable.

1. A zinc finger DNA-binding domain comprising four[, five] or six zinc finger recognition regions designated *and ordered* F1 to F4[, F1-F5] or F1 to F6 as shown in a single row of Table 1, *wherein the zinc finger DNA-binding domain binds to a target site specified in the first column of the single row of Table 1, and further wherein the target site is in an endogenous cellular glutamine synthetase (GS) gene*.

18. The cell line of claim [15] *17*, wherein the cell is a mammalian cell selected from the group consisting of a COS cell, a CHO cell, a VERO cell, a MDCK cell, a WI38 cell, a V79 cell, a B14AF28-G3 cell, a BHK cell, a HaK cell, a NS0cell, a SP2/0-Ag14 cell, a HeLa cell, an HEK293 cell, and a perC6 cell.

* * * * *